(12) United States Patent
Kahn et al.

(10) Patent No.: US 11,519,008 B2
(45) Date of Patent: Dec. 6, 2022

(54) EXOSOME DELIVERY SYSTEM

(71) Applicant: Joslin Diabetes Center, Boston, MA (US)

(72) Inventors: C. Ronald Kahn, Falls Church, VA (US); Thomas Thomou, Boston, MA (US)

(73) Assignee: Joslin Diabetes Center, Boston, MA (US)

(*) Notice: Subject to any disclaimer, the term of this patent is extended or adjusted under 35 U.S.C. 154(b) by 349 days.

(21) Appl. No.: 16/410,311

(22) Filed: May 13, 2019

(65) Prior Publication Data

US 2019/0338314 A1    Nov. 7, 2019

Related U.S. Application Data

(63) Continuation of application No. PCT/US2017/061324, filed on Nov. 13, 2017.

(60) Provisional application No. 62/421,817, filed on Nov. 14, 2016.

(51) Int. Cl.
| | |
|---|---|
| *C12N 15/88* | (2006.01) |
| *A61K 48/00* | (2006.01) |
| *C12N 9/22* | (2006.01) |
| *C12N 15/11* | (2006.01) |
| *C12N 15/113* | (2010.01) |
| *C12N 15/62* | (2006.01) |

(52) U.S. Cl.
CPC .......... *C12N 15/88* (2013.01); *A61K 48/0033* (2013.01); *C12N 9/22* (2013.01); *C12N 15/11* (2013.01); *C12N 15/1136* (2013.01); *C12N 15/62* (2013.01); *C07K 2319/03* (2013.01); *C07K 2319/33* (2013.01); *C12N 2310/122* (2013.01); *C12N 2310/141* (2013.01); *C12N 2310/20* (2017.05); *C12N 2310/531* (2013.01); *C12N 2320/32* (2013.01); *C12N 2330/51* (2013.01); *C12N 2800/80* (2013.01)

(58) Field of Classification Search
CPC .......... C12N 15/88; C12N 9/22; C12N 15/11; C12N 15/1136; C12N 15/62; C12N 2310/20; C12N 2310/122; C12N 2310/141; C12N 2310/531; C12N 2320/32; C12N 2330/51; C12N 2800/80; C12N 2330/10; C12N 15/111; C12N 15/113; C12N 2810/00; A61K 48/0033; C07K 2319/03; C07K 2319/33

See application file for complete search history.

(56) References Cited

U.S. PATENT DOCUMENTS

| | | |
|---|---|---|
| 2001/0000075 A1 | 3/2001 | Pan |
| 2010/0233251 A1 | 9/2010 | Andrian et al. |
| 2011/0123629 A1 | 5/2011 | Pitcovski et al. |
| 2013/0195899 A1* | 8/2013 | Ichim ................ A61K 39/0008 424/184.1 |
| 2014/0350085 A1 | 11/2014 | Lin et al. |
| 2015/0017127 A1 | 1/2015 | O'Shea et al. |
| 2015/0216892 A1* | 8/2015 | Thibonnier ............. A61K 9/48 424/489 |
| 2016/0067355 A1 | 3/2016 | Seow et al. |
| 2016/0153005 A1* | 6/2016 | Zhang ................. C12N 15/86 800/21 |

FOREIGN PATENT DOCUMENTS

| | | | |
|---|---|---|---|
| WO | 1996038728 A1 | 12/1996 | |
| WO | 2015002956 A1 | 1/2015 | |
| WO | WO-2015002956 A1 * | 1/2015 | ............. C12N 15/88 |
| WO | 2016174250 A1 | 11/2016 | |
| WO | WO-2016174250 A1 * | 11/2016 | ........... C12N 15/111 |
| WO | WO-2016201220 A1 * | 12/2016 | ............. G01N 33/92 |
| WO | WO-2017194499 A1 * | 11/2017 | ........... C12Q 1/6883 |

OTHER PUBLICATIONS

Rajeev et al. ChemBioChem 2015, 16, 903-908. (Year: 2015).*
Geldenhuys et al. "Drug Delivery and Nanoformulations for the Cardiovascular System". Research & reviews. Drug delivery. Feb. 2017;1 (1):32.
Hartman et al. "Delta/Notch-Like EGF-Related Receptor (ONER) is Expressed in Hair Cells and Neurons in the Developing and Adult Mouse Inner Ear" Journal of the Association for Research in Otolaryngology. Jun. 1, 2010; 11 (2):187-201.
International Search Report cited in PCT/US2017/061324 dated Jan. 22, 2018.
Mahon et al. "Na+/H+ Exchanger Regulatory Factor 2 Directs Parathyroid Hormone 1 Receptor Signalling". Nature. Jun. 20, 2002;417(6891):858-61.
Ohno et al. "Focus on Extracellular Vesicles: Development of Extracellular Vesicle-Based Therapeutic Systems". International journal of molecular sciences. Feb. 6, 2016;17(2):172.
Strong et al. "Concise Review: The Obesity Cancer Paradigm:Exploration of the Interactions and Crosstalk with Adipose" Stem cells, Feb. 1, 2015:33(2):318-26.
Gesta et al., "Evidence for a role of developmental genes in theorigin of obesity and body fat distribution" PNAS 103(17):6676-6681 (2006).
Obregon "Adipose tissues and thyroid hormones" Frontiers in Physiology 5:Article 479 (2014).
Sengenès et al. "Preadipocytes in the human subcutaneous adipose tissue display distinct features from the adult mesenchymal and hematopoietic stem cells" Journal of Cellular Physiology 205(1):114-122 (2005).

(Continued)

*Primary Examiner* — Janet L Epps-Smith
(74) *Attorney, Agent, or Firm* — McNeill Baur PLLC

(57) ABSTRACT

This disclosure relates to the field of exosome delivery systems. In particular, compositions comprising adipose-derived exosomes that may be used as a delivery system are encompassed. The exosome delivery system can be used to deliver exogenous cargo such as miRNA and other inhibitory RNAs, as well as proteins, to target cells in a subject.

16 Claims, 34 Drawing Sheets

Specification includes a Sequence Listing.

(56) References Cited

OTHER PUBLICATIONS

Tchkonia et al., "Identification of depot-specific human fat cell progenitors through distinct expression profiles and developmental gene patterns" Am J Physiol Endocrinol Metab 292:E298-E307 (2007).

Sharp et al., "Human BAT possesses molecular signatures that resemble beige/brite cells" PLoS One e49452 (2012).

Sidossis et al., "Brown and beige fat in humans: thermogenic adipocytes that control energy and glucose homeostasis" J Clin Invest 125(2):478-486 (2015).

Wu et al., "Beige adipocytes are a distinct type of thermogenic fat cell in mouse and human" Cell 150(2):366-376 (2012).

* cited by examiner

Protocol 1

Protocol 2

| Features | Controls | HIV Lipodystrophy |
|---|---|---|
| N | 4 | 4 |
| Age | 52 ± 2 | 53 ± 3 |
| BMI | 27 ± 1 | 26 ± 1 |
| Weight | 75 ± 4 | 67 ± 7 |
| CD4 cell count | N/A | 414 ± 142 |
| Duration HIV (yrs) | N/A | 18 ± 1.9 |
| Serum chol. (mg/dL) | 185 ± 8 | 180 ± 15 |

| Features | Controls | Lipo dystrophy |
|---|---|---|
| N | 4 | 4 |
| Age | 52 ± 2 | 13 ± 4 |
| BMI | 27 ± 1 | 17.7 ± 2.1 |
| Serum cholesterol (mg/dL) | 185 ± 8 | 233 ± 20 |

Figure 6A:
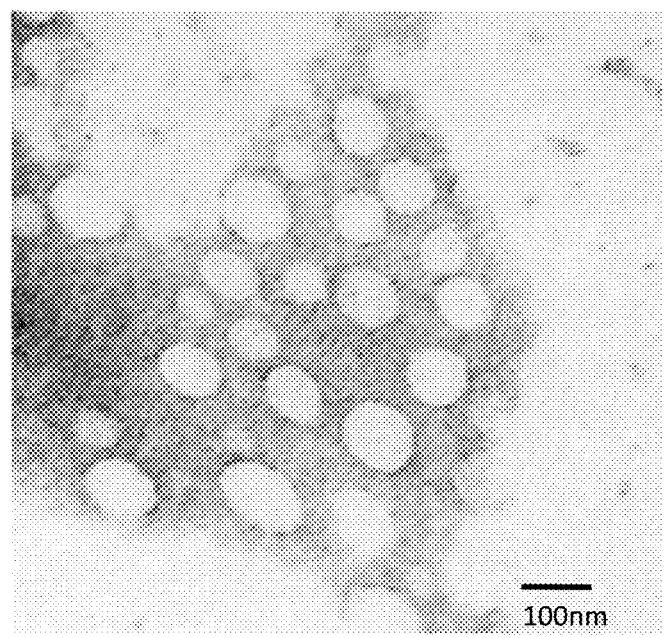
Figure 6B:
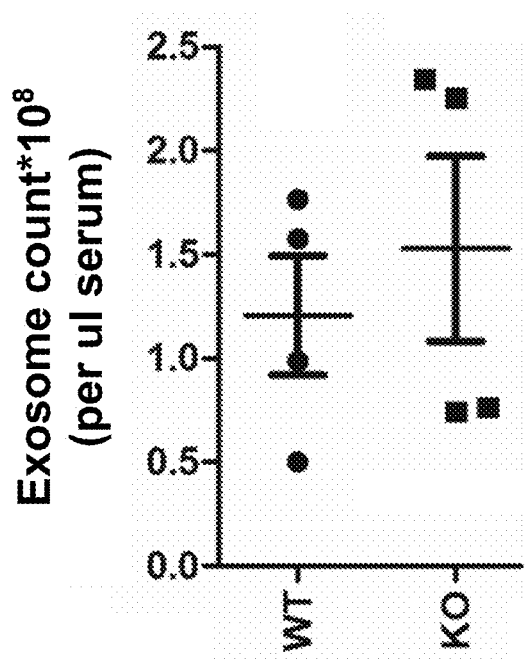
Figure 6C:
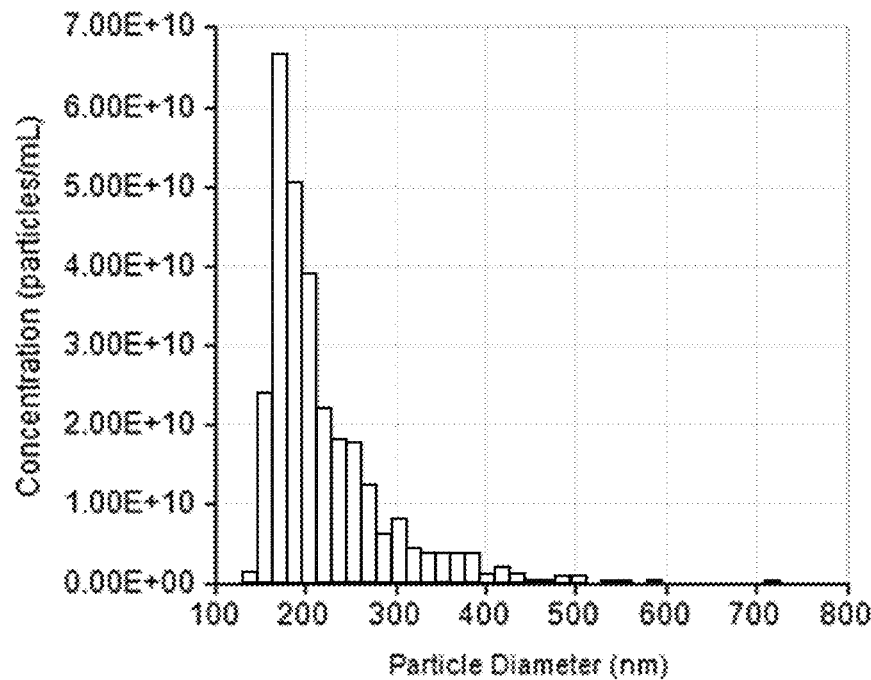
Figure 6C:
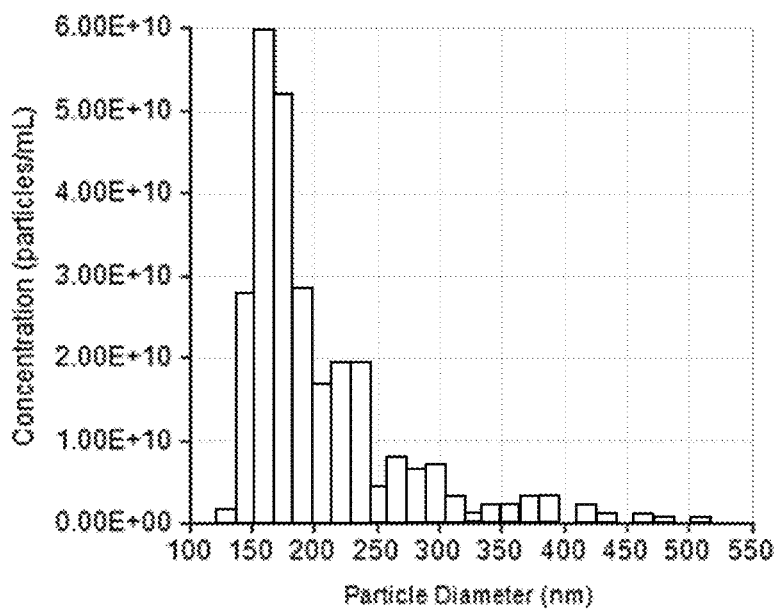

*Fig. 6H*

|  | WT | KO | | | |
|---|---|---|---|---|---|
|  |  | SAL | EPI | ING | BAT |
| INSULIN (pg/ml) | 136 ± 53 | 451 ± 169 | 631 ± 264 | 589 ± 283 | 332 ± 62 |
| IL-6 (pg/ml) | 11.3 ± 2.6 | 7.8 ± 2.3 | 6.9 ± 0.6 | 5.8 ± 1.6 | 6.7 ± 1.1 |
| LEPTIN (pg/ml) | 4764 ± 1678 | 3573 ± 929 | 4750 ± 2091 | 4578 ± 1087 | 4080 ± 743 |
| ADIPONECTIN (pg/ml) | 0.74 ± 0.18 | 0.3 ± 0.08 | 0.33 ± 0.11 | 0.61 ± 0.14 | 0.48 ± 0.04 |

EXOSOME DELIVERY SYSTEM

This application is a Continuation application of PCT/US2017/061324, which was filed on Nov. 13, 2017, which claims the benefit of priority to U.S. Provisional Application No. 62/421,817, which was filed on Nov. 14, 2016, both of which are incorporated by reference in their entirety.

The instant application contains a Sequence Listing which has been submitted electronically in ASCII format and is hereby incorporated by reference in its entirety. Said ASCII copy, created on May 10, 2019, is named 2018-05-10_01123-0006-00US_Seq_List_ST25.txt and is 10,081 bytes in size.

This study was supported by grants from the NIH R01 DK082659 and R01 DK033201.

miRNAs are a class of non-coding RNAs of 19-22 nucleotides that function as negative regulators of translation and are involved in many cellular processes[1,2,3]. In addition to tissues, many miRNAs can be found in the circulation[4], a large fraction of which are in exosomes[5], i.e., 50-200 nm vesicles which are released from cellular multivesicular bodies[6]. Increased levels of specific miRNAs have been associated with a variety of diseases, including cancer[7], diabetes[3,8,9] obesity[10], and cardiovascular disease[11]. Intracellular miRNAs play an important role in the differentiation and function of many cells, including different adipose tissue depots[12].

However, delivery of miRNAs and other small RNAs, such as shRNAs or RNAi's, as therapeutics is a critical step that needs to be overcome to transition miRNA and other RNA based therapeutics into clinical applications. Although miRNAs have been characterized to be found in exosomes, the use of exosomes as delivery systems has been limited. Most existing approaches for delivery of miRNA depend on the creation of delivery systems using artificial lipid vesicles. Lipid vesicles have the disadvantage of being of limited effectiveness and uncertain or uncontrollable fate in the body.

The present application relates to the field of exosome delivery systems. In particular, the inventors have shown that exosomes derived from fat (e.g., adipose tissue) are efficient delivery systems for regulatory miRNAs as well as other small RNAs, such as shRNAs or RNAi's. This approach can be used for both ex vivo derived exosomes and in vivo derived exosomes.

SUMMARY

The compositions and methods provided herein involve fat-derived exosomes carrying small nucleic acids, such as, for example, miRNA. The delivery system can be used to deliver any miRNA or small inhibitory RNAs (siRNA) to any particular tissue by attachment of a targeting moiety to the exosome. In some embodiments, the exosomes are derived from fat and do not comprise an exogenous (i.e., non-native to the fat derived exosome) targeting moiety. In some embodiments, the exosomes are derived from fat and comprise an exogenous targeting moiety.

In some embodiments, a delivery system comprises an exosome derived from adipose tissue, a targeting moiety that is not naturally expressed on the adipose-tissue derived exosome, and a recombinant nucleic acid ranging in size from about 50 to about several thousand nucleotides. In some embodiments, the nucleic acid is not naturally found within an exosome.

In some embodiments, the adipose tissue is brown adipose tissue. In some embodiments, the adipose tissue is white adipose tissue. In some embodiments, the adipose tissue is beige adipose tissue. In some embodiments, the adipose tissue is a combination of one or more of brown, white, and beige adipose tissue.

In some embodiments, the nucleic acid is DNA or RNA. In some embodiments, the nucleic acid is RNA. In some embodiments, the nucleic acid is a micro RNA (miRNA). In some embodiments, the nucleic acid is a small interfering RNA (siRNA). In some embodiments, the nucleic acid is a short hairpin RNA (shRNA). In some embodiments, the nucleic acid is a small nucleolar RNA (snoRNA). In some embodiments, the nucleic acid is less than 50, 100, 500, 1000, 2000, or 3000 nucleic acids. In some embodiments, the nucleic acid is less than 200, 100, 50, 40, 30, 20, 15, or 10 nucleic acids.

In some embodiments, the nucleic acid is long noncoding RNA (LncRNA). In some embodiments, the LNCRNA is longer than 200 nucleotides. In some embodiments, the LNCRNA is less than 300, 400, 500, 600, 700, 800, 900, 1000, 2000, or 3000 nucleotides.

In some embodiments, the exosome is derived from a human. In some embodiments, the targeting moiety functions to move the exosome from one location to another location within a subject. In some embodiments, the targeting moiety functions to regulate uptake of the exosome by tissues within a subject.

In some embodiments, the delivery system further comprises a recombinant protein(s) expressed within an exosome. In some embodiments, the recombinant protein(s) is part of the CRISPR-Cas ribonucleoprotein complex.

In some embodiments, the targeting moiety is conjugated to the exosome. In some embodiments, the targeting moiety is conjugated to the exosome by expressing the targeting moiety as a fusion protein together with an exosomal transmembrane protein.

In some embodiments, the targeting moiety is a ligand that binds to membrane receptors at the target. In some embodiments, the targeting moiety is one or more of Asialoglycoprotein Receptor (ASGPR), Toll-Like Receptor 4 ligand (TLR-4 ligand), Notch, CGS-21680, Parathyroid hormone receptor 1 (PTHR1), and Fractalkine receptor (CX3CR1).

In some embodiments, antibodies or portions of antibodies are used to target the RNA to a desired location. In some embodiments, antibodies bind to specific cell surface proteins.

In some embodiments, the targeting moiety is an epitope naturally present in an exosome representing a specific cell surface protein from the cell releasing the exosome.

In some embodiments, the targeting moiety is Asialoglycoprotein Receptor (ASGPR), and wherein ASGPR targets the exosome to N-acetylgalactosamine (Gal-N—Ac). In some embodiments, Gal-N—Ac is in the liver.

In some embodiments, the targeting moiety is Toll-Like Receptor 4 ligand (TLR-4 ligand), and wherein TLR-4 ligand targets the exosome to Toll-Like Receptor 4 receptor (TLR-4 receptor). In some embodiments, TLR-4 receptor is in the liver.

In some embodiments, the targeting moiety is Notch, and wherein Notch targets the exosome to Delta/Notch-like EGF-related receptor (DNER). In some embodiments, DNER is in the brain.

In some embodiments, the targeting moiety is CGS-21680, and wherein CGS-21680 targets the exosome to Adenosine A2A receptor. In some embodiments, Adenosine A2A receptor is in the brain or heart.

In some embodiments, the targeting moiety is Parathyroid hormone receptor 1 (PTHR1), and wherein PTHR1 targets the exosome to Parathyroid Hormone 1 (PTH-1). In some embodiments, PTH-1 is in the kidney, lung, or placenta.

In some embodiments, the targeting moiety is Fractalkine receptor (CX3CR1), and wherein CX3CR1 targets the exosome to Neurotactin (CX3CL1). In some embodiments, CX3CL1 is in the peripheral neurons or kidney.

In some embodiments, a method for producing an adipose-derived exosome delivery system is encompassed, comprising isolating adipose tissue from a subject; isolating adipocytes or preadipocytes from the adipose tissue; and contacting the isolated adipocytes or preadipocytes with a nucleic acid vector comprising nucleic acids capable of expressing one or more nucleic acid, thereby producing an adipose-derived exosome delivery system. In some embodiments, this nucleic acid is miRNA, siRNA, shRNA, snoRNA, or LncRNA.

In some embodiments, the method further comprises contacting the isolated adipocytes or preadipocytes with a nucleic acid vector comprising nucleic acids encoding a targeting moiety.

In some embodiments, the subject is human.

In some embodiments, the targeting moiety is expressed on the surface of the exosome. In some embodiments, the targeting moiety is expressed within the membrane of the exosome. In some embodiments, the targeting moiety is expressed within the membrane of the exosome.

In some embodiments, the nucleic acids encoding the targeting moiety comprise a fusion protein, wherein the fusion protein comprises an exosomal transmembrane protein and a targeting moiety.

FIGURE LEGENDS

Description of the Sequences

FIGS. 1A, 1B, 1C, 1D, 1E, 1F, and 1G show that fat tissue is a major source of circulating exosomal miRNAs in both mice and humans. (a) Schematic showing creation of ADicerKO mice by crossing floxed Dicer (Dicer$^{lox-lox}$) with mice carrying an adiponectin promoter-Cre transgene. (b) Immunoelectron microscopy of the tetraspanins CD63 and CD9 in exosomes isolated from murine sera. (c) Heatmap showing Z-scores of exosomal miRNA expression measurements from serum of ADicerKO (KO) and Lox (WT) control mice (n=4 per group). (d) Waterfall plot representing the relative abundance on a $log_2$ scale of serum exosomal miRNAs that were statistically different between the ADicerKO and the Lox control mice (n=4 per group, p<0.05). (e) Heatmap showing Z-scores of exosomal miRNA measurements in serum of humans with HIV lipodystrophy (HIV), generalized lipodystrophy (CGL) and normal controls (n=4 per group). (f) Waterfall plots representing the relative abundance on a $log_2$ scale of fold-change differences of exosomal miRNAs that were differentially expressed between human HIV lipodystrophy, human generalized lipodystrophy and normal subjects (n=4 per group, p<0.05). (g) Venn diagrams representing significantly up-regulated and down-regulated miRNAs in HIV lipodystrophy and human generalized lipodystrophy compared to controls (n=4 per group, p<0.05).

FIGS. 2A, 2B, 2C, 2D, and 2E show fat depot contributions to circulating exosomal miRNAs using a transplantation approach. (a) Schematic of the fat tissue transplantation experiment using WT donor inguinal (Ing), epididymal (Epi) and brown adipose tissue (BAT) which was transplanted into inguinal region in ADicerKO recipient mice. Mice were followed for a total of 14 days after transplantation. Fat pads from WT donors were assessed for miRNA signatures, and serum exosomal miRNA from ADicerKO transplanted mice was subjected to miRNA profiling at the time of sacrifice. (b) Heatmap showing Z-scores of miRNA expression in inguinal (Ing), epididymal (Epi), and brown adipose tissue (BAT) from WT donor mice (n=4 per group, miRNA expression normalized by global average values for each sample; see methods). The Venn diagram represents number of miRNAs whose expression exceeded U6 snRNA in inguinal (Ing), epididymal (Epi), and brown adipose tissue (BAT) from WT donor mice (n=4 per group). (c) Heatmap exhibiting Z-scores of serum exosomal miRNA measurements in ADicerKO and wild type (WT) C57Bl/6 mice (both receiving sham surgery) and in ADicerKO mice transplanted with Ing, Epi, and BAT fat from WT mice (n=4 per group). The Venn diagram represents miRNAs reconstituted significantly and by at least 50% of the way to WT miRNA values in inguinal (Ing), epididymal (Epi), and brown adipose tissue (BAT) from ADicerKO transplant groups (n=4 per group, p<0.05). (d) Glucose tolerance test of wild-type C57Bl/6 mice and ADicerKO (both 12 days after sham surgery). Mice were fasted for 16 hrs and injected intraperitoneally with 20% glucose at 2 g/kg dose (n=3 per group, p=0.0001, WT vs KO at 0 min; p=0.013, WT vs KO at 15 min; p=0.0001, WT vs KO at 90 min, two-tailed t-test; error bars represent standard deviation from the mean). (e) Area under the curve (AUC) graph of the glucose tolerance test of the ADicerKO (sham surgery), wild type C57Bl/6 mice (sham surgery) and in ADicerKO transplanted with Ing, Epi, and BAT fat from WT mice; each mouse received two fat pads from the donor (n=3 per group, p=0.0002, WT vs KO, p=0.033 KO vs KO+BAT, two-tailed t-test). Error bars represent SEM.

FIGS. 3A, 3B, 3C, 3D, 3E, and 3F show that fat depot derived exosomal miRNA mediate regulation of fibroblast growth factor 21 (FGF21) and transcription in liver. (a) Enzyme-linked immunoassay of FGF21 in serum of ADicerKO mice and Lox control littermates (n=4 per group, p=0.028, two-tailed Mann-Whitney U test). (b) Quantitative PCR of hepatic FGF21 mRNA abundance in Lox and ADicerKO mice (n=4 per group, p=0.028, two-tailed Mann-Whitney U test). (c) Enzyme-linked immunoassay of FGF21 in serum of ADicerKO (sham surgery), WT C57Bl/6 mice (sham surgery) and of ADicerKO transplanted with Ing, Epi, or BAT fat (n=3 per group, p=0.019, Cont vs KO+BAT, two-tailed t-test). (d) qPCR of hepatic FGF21 mRNA abundance in ADicerKO (sham surgery), wild type C57Bl/6 mice (sham surgery), and ADicerKO transplanted with Ing, Epi, and BAT fat (n=3 per group, p=0.046, Cont vs KO+BAT, two-tailed t-test). (e) Hepatic FGF21 3'UTR luciferase activity after incubation of AML-12 hepatic cells with exosomes derived from either Lox control mice (exoWT), ADicerKO mice (exoKO), 10 nM free miR-99b (miR-99b free) or with exosomes derived from ADicerKO mice electroporated with miR-99b (exoKO+miR-99b) (n=3 per group, p=0.008, WT vs. KO, p=0.008, KO vs. KO+99b, two-tailed t-test) (f) Hepatic FGF21 3'UTR luciferase activity after incubation of AML-12 hepatic cells with exosomes derived from either ADicerKO, Lox control littermates (WT), or exosomes isolated from ADicerKO mice and electroporated to introduce miR-99a, miR-99b, miR-100 or miR-466i (original concentration 10 nM of miRNA mimic). Electroporated exosomes were resuspended in a total volume of 500 ul PBS per mimic and added to the target cells. (n=3 per group, p=0.0007, exoWT vs. exoKO, p=0.002, exoKO vs. exoKO+ 99b, two-tailed t-test). Indicated t-test comparisons were the only ones performed.

FIGS. 4A, 4B, 4C, 4D, 4E, 4F, 4G, and 4H show in vivo regulation of FGF21 via exosomal delivery of at least one regulator miRNA, miR-99b. (a) Lox mice (WT), ADicerKO mice (KO), and ADicerKO injected i.v. with wild type exosomes (KO+exoWT) transduced with pacAd5-Luc-FGF21-3'UTR luciferase reporter and subjected to IVIS analysis. (b) Total flux measurements of luminescence obtained via IVIS analysis from ADicerKO (KO), Lox mice (WT), or ADicerKO mice injected i.v. with wild type exosomes (KO+exoWT) transduced with pacAd5-Luc-FGF21-3'UTR luciferase reporter (n=3 per group, p=0.039, Kruskal Wallis ANOVA, significant comparison WT vs KO, Dunn's post hoc test). (c) qPCR of hepatic FGF21 mRNA abundance in Lox mice (WT), ADicerKO (KO) and ADicerKO injected i.v. with wild type exosomes (KO+exoWT) (n=3 per group, p=0.039, Kruskal Wallis ANOVA, significant comparison WT vs KO, Dunn's post hoc test). (d) Enzyme-linked immunoassay of FGF21 in serum of Lox mice (WT), ADicerKO (KO) or ADicerKO injected i.v. with wild type exosomes (KO+exoWT) (n=3 per group, p=0.027, Kruskal Wallis ANOVA, significant comparison WT vs KO, Dunn's post hoc test) (e) Lox mice injected i.v. with ADicerKO exosomes (WT+exoKO) and ADicerKO mice injected i.v. with either ADicerKO exosomes (KO+exoKO) or ADicerKO exosomes electroporated with miR-99b (KO+exomiR99b) and subjected to IVIS analysis. (f) Total flux measurements of luminescence obtained via IVIS analysis from Lox mice injected i.v. with ADicerKO exosomes (WT+exoKO) and ADicerKO mice injected i.v. with either ADicerKO exosomes (KO+exoKO) or ADicerKO exosomes electroporated with miR-99b (KO+exomiR99b). (n=3 per group, p=0.079, Kruskal Wallis ANOVA, Dunn's post hoc test). (g) qPCR of hepatic FGF21 mRNA abundance in Lox mice injected i.v. with ADicerKO exosomes (WT+exoKO) and ADicerKO mice injected i.v. with either ADicerKO exosomes (KO+exoKO) or ADicerKO exosomes electroporated with miR-99b (KO+exomiR99b). (n=3 per group, p=0.039, Kruskal Wallis ANOVA, significant comparison WT+exoKO vs KO+exoKO, Dunn's post hoc test). (h) Enzyme-linked immunoassay of FGF21 in serum of Lox mice injected i.v. with ADicerKO exosomes (WT+exoKO) and ADicerKO mice injected i.v. with either ADicerKO exosomes (KO+exoKO) or ADicerKO exosomes electroporated with miR-99b (KO+exomiR99b). (n=3 per group, p=0.027, Kruskal Wallis ANOVA, significant comparison WT+exoKO vs KO+exoKO, Dunn's post hoc test). Error bars represent SEM.

FIGS. 5A, 5B, 5C, 5D, 5E, 5F, and 5G show that BAT-derived exosomes expressing human-specific miRNA miR-302f target their reporter in liver of mice in vivo. (a) Protocol 1. C57Bl/6 mice were injected with an adenovirus bearing pre-miR-302f or an adenovirus bearing LacZ as control directly into BAT. This miRNA is human specific and does not have a mouse homolog. 8 days later, the same mice were injected i.v. with an adenovirus bearing the 3'-UTR of this miR-302f in-frame with the Luciferase gene, thereby allowing expression of this human reporter in the liver of the mouse. Only if there is a communication between the BAT produced miRNA and the liver would suppression of the 302f reporter be observed. IVIS analysis was performed after 5 days. (b) C57Bl/6 mice injected i.v. with an adenovirus bearing the 3'-UTR of miR-302f in frame with the luciferase gene after BAT specific injection of Ad-pre-hsa-miR-302f, or Ad-LacZ and subjected to IVIS analysis (n=4 per group). (c) Total flux measurements of luminescence obtained via IVIS analysis from C57Bl/6 mice transduced with pacAd5-hsa_miR-302f 3'-UTR luciferase reporter after BAT specific injection of Ad-pre-hsa_miR-302f, or Ad-LacZ. (n=4 per group, p=0.028, Mann-Whitney U test). (d) Protocol 2. To assess exosomal contribution of miR-302f suppression into the liver, two separate cohorts of C57Bl/6 mice were generated: one cohort with the adenovirus bearing pre-miR-302f or LacZ as control directly into BAT (donor cohort) and a second cohort transduced in the liver with the adenovirus containing the 3'-UTR of this miR-302f (acceptor cohort). Serum was obtained from the donor cohort on days 3 and 6 and at a terminal bleed on day 8, exosomes were isolated and injected i.v. into the acceptor mice. IVIS analysis was performed on the acceptor mice. (e) C57Bl/6 mice transduced with pacAd5-hsa_miR-302f 3'-UTR luciferase reporter after serum exosome i.v. injections from Ad-pre-hsa_miR-302f or Ad-LacZ BAT injected mice and subjected to IVIS analysis (n=4 per group). (f) Total flux measurement of luminescence obtained from IVIS analysis from C57Bl/6 mice transduced with pacAd5-hsa_miR-302f 3'-UTR luciferase reporter serum exosome i.v. injections from Ad-pre-hsa_miR-302f or Ad-LacZ BAT injected mice (n=4 per group, p=0.028, two-tailed Mann-Whitney U test). Error bars represent SEM (g) Model of mechanism by which adipose tissue derived exosomal miR-NAs in the circulation might regulate target mRNAs in various tissues.

FIGS. 6A, 6B, 6C, 6D, 6E, 6F, 6G, 6H, 6I, and 6J show characterization of samples from ADicerKO mice and human patients with lipodystrophies. (a) Electron microscopy of exosomes isolated from ADicerKO serum by differential centrifugation. (b) EXOCET ELISA assay (BioCat, Cat #EXOCET96A-1-SBI) measuring cholestererylester transfer protein (CETP) protein in exosome samples, corresponding to isolated exosome number from serum of ADicerKO (KO) or littermate mice (Lox). (c) qNano assay (IZON) measuring exosome numbers and size based on Tunable Resistive Pulse Sensing technology from exosome preparations from ADicerKO or Lox mice. (d) Principle Component Analysis of exosomal miRNA levels in ADicerKO (KO) and Lox (WT), n=4 per group. (e) Heatmap showing Z-scores of miRNA expression measurements from whole serum ADicerKO (KO) or littermate wild type mice (WT) and exosomal miRNAs from ADicerKO (KO) or littermate wild type mice (WT) (n=4 per group). (f) Heatmap showing Z-scores of miRNA expression measurements of exosomal miRNAs from culture supernatant of Dicer$^{fl/fl}$ preadipocytes transduced with Ad-GFP (GFP) or Ad-CRE (CRE) (n=3 per group). (g) Heatmap showing Z-scores of miRNA expression measurements of exosomal miRNAs from serum of 4-week old ADicerKO (ADicerKO) and Lox (Control) mice (n=3 per group). (h) Demographic information of human patients with HIV lipodystrophy (HIV), congenital generalized lipodystrophy (CGL) or normal subjects. (i) EXOCET ELISA assay measuring CETP protein as a measure of exosome number from isolated from human sera of individuals with HIV Lipodystrophy, congenital generalized lipodystrophy (CGL) and control subjects (n=4 per group). (j) Principle Component Analysis of exosomal miRNA expression in HIV Lipodystrophy, CGL, and control subjects, n=4 per group. Error bars represent SEM.

FIGS. 7A, 7B, 7C, 7D, and 7E show characterization of effects of adipose tissue transplants on circulating exosomal miRNAs and physiological responses in the recipient. (a) Principle Component Analysis of miRNA expression in mouse fat depots: epididymal (Epi), inguinal (Ing), and brown adipose tissue (BAT), n=4 per group. (b) Weights of the transplanted epididymal (Epi), inguinal (Ing), and brown adipose tissue (BAT) at time of transplantation into ADicerKO mice and at time of sacrifice, n=3-4. (c) Weights of ADicerKO mice undergoing sham surgery (Sal) or with transplanted epididymal (Epi), inguinal (Ing), or brown adipose tissue (BAT) and Lox (WT) mice. (d) Principle component analysis of variance of serum exosomal miRNA levels in ADicerKO after sham surgery or transplantation with inguinal fat, with epididymal fat or BAT, and Lox controls, n=4 per group. (e) Circulating insulin, interleukin 6 (IL-6), leptin, and adipokine levels in WT, ADicerKO, or transplanted ADicerKO mice (n=3-4 per group, two-tailed t-test, p<0.05). Error bars represent SEM.

FIGS. 8A, 8B, 8C, 8D, and 8E show profiles of selected miRNAs. (a) FGF21 mRNA levels as assessed by qPCR in liver (LIV), BAT, inguinal (Ing), epididymal (Epi), pancreas (Panc), kidney (Kidn), and quadriceps muscle (Quad) of ADicerKO (black bars) or Lox (white bars) (n=4 per group, p=0.0286, two-tailed Mann Whitney U test). (b) Relative abundance (log 2FC) as assessed by qPCR of miR-99a, miR-99b, and miR-100 in exosomes from ADicerKO undergoing fat transplantation surgery compared to sham, n=4 per group. (c) FGF21 3'UTR luciferase activity in murine liver cells (AML-12) following introduction of miR-99a, miR-99b, miR-100 or miR-466i (10 nM of miRNA mimic) by direct electroporation (n=3 per group, p=0.003, two-tailed t-test). (d) FGF21 mRNA abundance in murine liver cells (AML-12) following transduction with miRNA mimics of miR-99a, miR-99b, miR-100 or miR-466i (10 nM) (n=3 per group, p=0.037, two tailed t-test). (e) Hepatic FGF21 mRNA levels by qPCR followed by 48 hrs incubation of AML-12 hepatic cells with exosomes derived from ADicerKO or Lox littermates (WT) mice or with ADicerKO-isolated exosomes electroporated with 10 nM of miR-99a, miR-99b, miR-100 or miR-466i (n=3 per group, p=0.0001, two-tailed t-test). Error bars represent SEM.

Figure 9A:
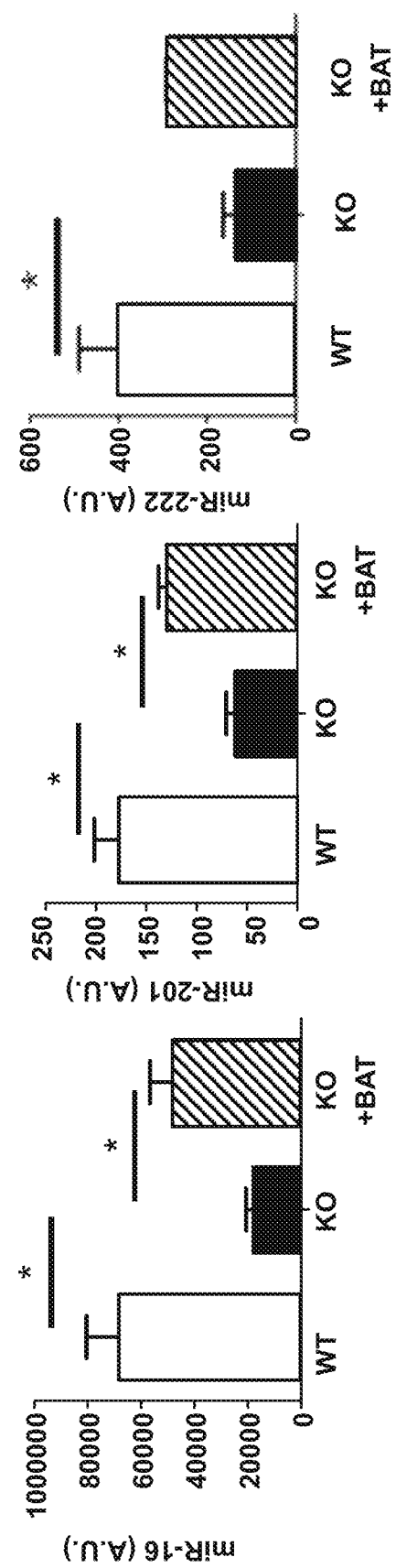
Figure 9B:
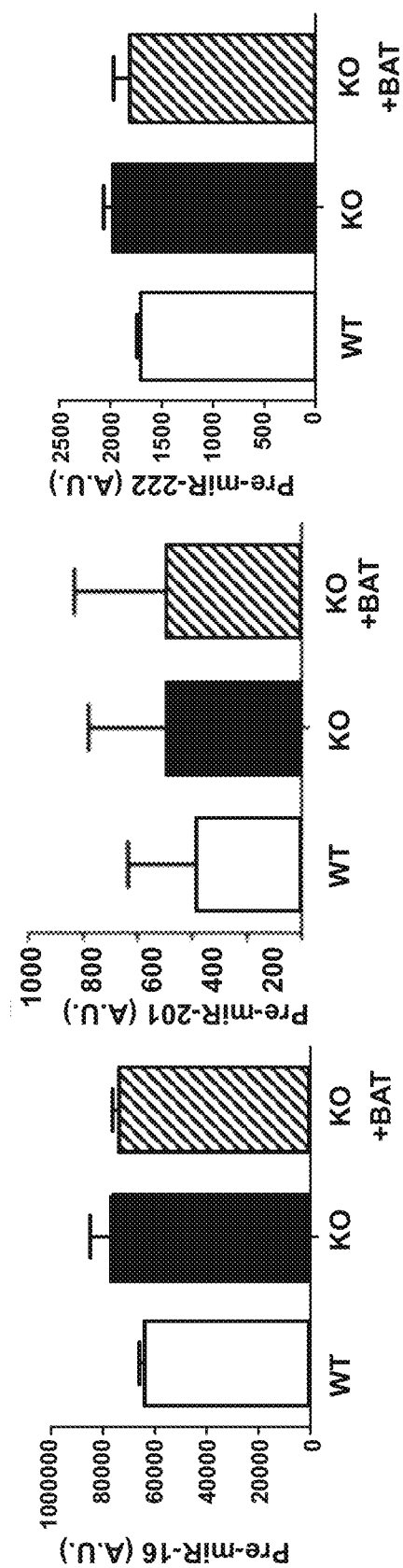
Figure 9C:
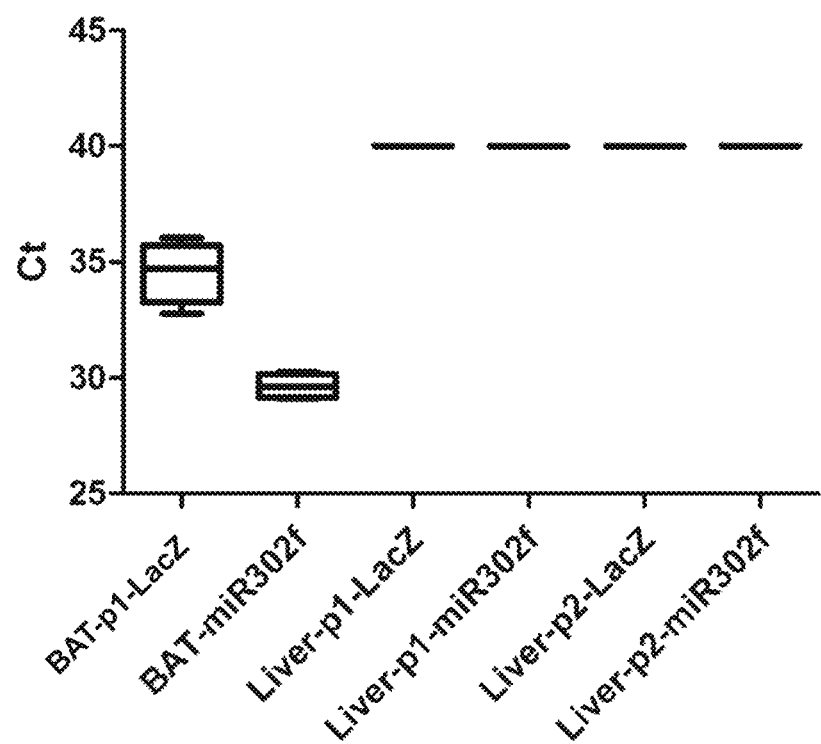

FIGS. 9A, 9B, and 9C show (a) qPCR of mature miR-16, miR-201, and miR-222 in liver of Lox mice (WT), ADicerKO mice (KO), and ADicerKO transplanted with BAT (KO+BAT) (n=3 per group, p=0.02 for miR-16, p=0.002 for miR-201, and p=0.028 for miR-222; one-way Analysis of variance. Significant comparisons were identified by Tukey's multiple comparisons test). (b) qPCR of pre-miR-16, pre-miR-201, and pre-miR-222 abundance in liver of Lox mice (WT), ADicerKO mice (KO), and ADicerKO transplanted with BAT (KO+BAT) (n=3 per group, p<0.05, one-way analysis of variance). (c) CT values of qPCR of Adenoviral DNA isolated from BAT-p1 and liver-p1 (experimental protocol 1) and liver-p2 (experimental protocol 2) detecting Adenoviral LacZ or pre-miR-302f (n=4 per group). Error bars represent SEM.

DESCRIPTION OF THE SEQUENCES

Table 10 provides a listing of certain sequences referenced herein.

TABLE 10

Description of the Sequences

| Description | Sequences | SEQ ID NO |
|---|---|---|
| Ad-pre-hsa_miR-302f | gatttaaatcggactgaattcctgggttccttggggaggaggggggccggggg cccggactcctgggtcctggcacccaccccgtagaaccgaccttgcggggcct tcgccgcacacaagctcgtgtctgtgggtccgtgtcgggggctcaccatcgc ggctgggacctccccggccctccccacccctcgag | 1 |
| Ad-LacZ | accatgattacggattcactggccgtcgttttacaacgtcgtgactgggaaa accctggcgttacccaacttaatcgccttgcagcacatcccccttcgccag ctggcgtaatagcgaagaggcccgcaccgatcgcccttcccaacagttgcgc agcctgaatggcgaatggcgctttgcctggtttccggcaccagaagcggtgc cggaaagctggctggagtgcgatcttcctgaggccgatactgtcgtcgtccc ctcaaactggcagatgcacggttacgatgcgcccatctacaccaacgtaacc tatcccattacggtcaatccgccgtttgttcccacggagaatccgacgggtt gttactcgctcacatttaatgttgatgaaagctggctacaggaaggccagac gcgaattattttgatggcgttaactcggcgtttcatctgtggtgcaacggg cgctgggtcggttacggccaggacagtcgtttgccgtctgaatttgacctga gcgcatttttacgcgccggagaaaaccgcctcgcggtgatggtgctgcgttg gagtgacggcagttatctggaagatcaggatatgtggcggatgagcggcatt ttccgtgacgtctcgttgctgcataaaccgactacacaaatcagcgatttcc atgttgccactcgctttaatgatgatttcagccgcgctgtactggaggctga agttcagatgtgcggcgagttgcgtgactacctacgggtaacagtttcttta tggcagggtgaaacgcaggtcgccagcggcaccgcgcctttcggcggtgaaa ttatcgatgagcgtggtggttatgccgatcgcgtcacactacgtctgaacgt cgaaaacccgaaactgtggagcgccgaaatcccgaatctctatcgtgcggtg gttgaactgcacaccgccgacggcacgctgattgaagcagaagctgcgatg tcggtttccgcgaggtgcggattgaaaatggtctgtgctgctgaacggcaag ccgttgctgattcgaggcgttaaccgtcacgagcatcatcctctgcatggtc aggtcatggatgagcagacgatggtgcaggatatcctgctgatgaagcagaa caactttaacgccgtgcgctgttcgcattatccgaaccatccgctgtggtac acgctgtgcgaccgctacggcctgtatgtggtggatgaagccaatattgaaa cccacggcatggtgccaatgaatcgtctgaccgatgatccgcgctggctacc ggcgatgagcgaacgcgtaacgcgaatggtgcagcgcgatcgtaatcacccg agtgtgatcatctgtcgctggggaatgaatcaggccacggcgctaatcacg acgcgctgtatcgctggatcaaatctgtcgatccttcccgcccggtgcagta tgaaggcggcggagccgacaccacggccaccgatattatttgcccgatgtac gcgcgcgtggatgaagaccagcccttcccggctgtgccgaaatggtccatca aaaaatggctttcgctacctggagagacgcgcccgctgatcctttgcgaata cgccacgcgatgggtaacagtcttggcggtttcgctaaatactggcaggcg | 2 |

TABLE 10-continued

Description of the Sequences

| Description | Sequences | SEQ ID NO |
|---|---|---|
| | tttcgtcagtatccccgtttacagggcggcttcgtctgggactgggtggatc<br>agtcgctgattaaatatgatgaaaacggcaacccgtggtcggcttacggcgg<br>tgattttggcgatacgccgaacgatcgccagttctgtatgaacggtctggtc<br>tttgccgaccgcacgccgcatccagcgctgacggaagcaaaacaccagcagc<br>agttttccagttccgtttatccgggcaaaccatcgaagtgaccagcgaata<br>cctgttccgtcatagcgataacgagctcctgcactggatggtggcgctggat<br>ggtaagccgctggcaagcggtgaagtgcctctggatgtcgctccacaaggta<br>aacagttgattgaactgctgaactaccgcagccggagagcgccgggcaactc<br>tggctcacagtacgcgtagtgcaaccgaacgcgaccgcatggtcagaagccg<br>ggcacatcagcgcctggcagcagtggcgtctggcggaaaacctcagtgtgac<br>gctccccgccgcgtcccacgccatcccgcatctgaccaccagcgaaatggat<br>ttttgcatcgagctgggtaataagcgttggcaatttaaccgccagtcaggct<br>ttctttcacagatgtggattggcgataaaaaacaactgctgacgccgctgcg<br>cgatcagttcacccgtgcaccgctggataacgacattggcgtaagtgaagcg<br>acccgcattgaccctaacgcctgggtcgaacgctggaaggcggcgggccatt<br>accaggccgaagcagcgttgttgcagtgcacggcagatacacttgctgatgc<br>ggtgctgattacgaccgctcacgcgtggcagcatcaggggaaaaccttattt<br>atcagccgaaaacctaccggattgatggtagtggtcaaatggcgattaccg<br>ttgatgttgaagtggcgagcgatacaccgcatccggcgcggattggcctgaa<br>ctgccagctggcgcaggtagcagagcgggtaaactggctcggattagggccg<br>caagaaaactatcccgaccgccttactgccgcctgttttgaccgctgggatc<br>tgccattgtcagacatgtatacccgtacgtcttcccgagcgaaaacggtct<br>gcgctgcgggacgcgcgaattgaattatgggcccacaccagtggcgcggcgac<br>ttccagttcaacatcagccgctacagtcaacagcaactgatggaaaccagcc<br>atcgccatctgctgcacgcggaagaaggcacatggctgaatatcgacggttt<br>ccatatggggattggtggcgacgactcctggagcccgtcagtatcggcggaa<br>ttccagctgagcgccggtcgctaccattaccagtttctggtgtcaaaaataa<br>taacggctgccgt | |
| Ad-Luc-miR-<br>302f-3'UTR | gatttaaatcatggaagacgccaaaaacataaagaaaggcccggcgccattc<br>tatccgctggaagatggaaccgctggagagcaactgcataaggctatgaaga<br>gatacgcccctggttcctggaacaattgcttttacagatgcacatatcgaggt<br>ggacatcacttacgctgagtacttcgaaatgtccgttcggttggcagaagct<br>atgaaacgatatgggctgaatacaaatcacagaatcgtcgtatgcagtgaaa<br>actctcttcaattctttatgccggtgttgggcgcgttatttatcggagttgc<br>agttgcgcccgcgaacgacatttataatgaacgtgaattgctcaacagtatg<br>ggcatttcgcagcctaccgtggtgttcgtttccaaaaaggggttgcaaaaaa<br>ttttgaacgtgcaaaaaaagctcccaatcatccaaaaaattattatcatgga<br>ttctaaaacggattaccagggatttcagtcgatgtacacgttcgtcacatct<br>catctacctcccggttttaatgaatacgattttgtgccagagtccttcgata<br>gggacaagacaattgcactgatcatgaactcctctggatctactggtctgcc<br>taaaggtgtcgctctgcctcatagaactgcctgcgtgagattctcgcatgcc<br>agagatcctattttggcaatcaaatcattccggatactgcgattttaagtg<br>ttgttccattccatcacggttttggaatgtttactacactcggatatttgat<br>atgtggatttcgagtcgtcttaatgtatagatttgaagaagagctgtttctg<br>aggagccttcaggattacaagattcaaagtgcgctgctggtgccaaccctat<br>tctccttcttcgccaaaagcactctgattgacaaatacgatttatctaattt<br>acacgaaattgcttctggtggcgctcccctctctaaggaagtcggggaagcg<br>gttgccaagaggttccatctgccaggtatcaggcaaggatatgggctcactg<br>agactacatcagctattctgattacacccgagggggatgataaaccgggcgc<br>ggtcggtaaagttgttccattttttgaagcgaaggttgtggatctggatacc<br>gggaaaacgctgggcgttaatcaaagaggcgaactgtgtgtgagaggtccta<br>tgattatgtccggttatgtaaacaatccggaagcgaccaacgccttgattga<br>caaggatggatggctacattctggagacatagcttactgggacgaagacgaa<br>cacttcttcatcgttgaccgcctgaagtctctgattaagtacaaaggctatc<br>aggtggctcccgctgaattggaatccatcttgctccaacaccccaacatctt<br>cgacgcaggtgtcgcaggtcttcccgacgatgacgccggtgaacttcccgcc<br>gccgttgttgttttggagcacggaaagacgatgacggaaaaagagatcgtgg<br>attacgtcgccagtcaagtaacaaccgcgaaaaagtgcgcggaggagttgt<br>gtttgtggacgaagtaccgaaaggtcttaccggaaaactcgacgcaagaaaa<br>atcagagagatcctcataaaggccaagaagggcggaaagatcgccgtgtaat<br>tctaaaacatggaagcaattaatcgaaacatggaagcaattagagggcccta<br>ttctatagtgtcacctaaatgctagagctcgctgatcagcctcgactgtgcc<br>ttctagttgccagccatctgttgtttgcccctcccccgtgccttccttgacc<br>ctggaaggtgccactcccactgtcctttcctaataaaatgaggaaattgcat<br>cgcattgtctgagtaggtgtcattctattctggggggtggggtggggcagga<br>cagcaaggggggaggattgggaagacaatagcaggcatgctggggatgcggtg<br>ggctctatggctcgag | 3 |
| Ad-Luc-<br>FGF21-3'UTR | atggaagacgccaaaaacataaagaaaggcccggcgccattctatccgctgg<br>aagatggaaccgctggagagcaactgcataaggctatgaagagatacgccct<br>ggttcctggaacaattgcttttacagatgcacatatcgaggtggacatcact<br>tacgctgagtacttcgaaatgtccgttcggttggcagaagctatgaaacgat<br>atgggctgaatacaaatcacagaatcgtcgtatgcagtgaaaactctcttca | 4 |

TABLE 10-continued

Description of the Sequences

| Description | Sequences | SEQ ID NO |
|---|---|---|
| | attctttatgccggtgttgggcgcgttatttatcggagttgcagttgcgccc gcgaacgacatttataatgaacgtgaattgctcaacagtatgggcatttcgc agcctaccgtggtgttcgtttccaaaaaggggttgcaaaaaattttgaacgt gcaaaaaaagctcccaatcatccaaaaaattattatcatggattctaaaacg gattaccagggatttcagtcgatgtacacgttcgtcacatctcatctacctc ccggttttaatgaatacgattttgtgccagagtccttcgatagggacaagac aattgcactgatcatgaactcctctggatctactggtctgcctaaaggtgtc gctctgcctcatagaactgcctgcgtgagattctcgcatgccagagatccta tttttggcaatcaaatcattccggatactgcgattttaagtgttgttccatt ccatcacggttttggaatgtttactacactcggatatttgatatgtggattt cgagtcgtcttaatgtatagatttgaagaagagctgtttctgaggagccttc aggattacaagattcaaagtgcgctgctggtgccaaccctattctccttctt cgccaaaagcactctgattgacaaatacgatttatctaatttacacgaaatt gcttctggtggcgctcccctctctaaggaagtcggggaagcggttgccaaga ggttccatctgccaggtatcaggcaaggatatgggctcactgagactacatc agctattctgattacacccgaggggatgataaaccgggcgcggtcggtaaa gttgttccatttttgaagcgaaggttgtggatctggataccgggaaaacgc tgggcgttaatcaaagaggcgaactgtgtgtgagaggtcctatgattatgtc cggttatgtaaacaatccggaagcgaccaacgccttgattgacaaggatgga tggctacattctggagacatagcttactgggacgaagacgaacacttcttca tcgttgaccgcctgaagtctctgattaagtacaaaggctatcaggtggctcc cgctgaattggaatccatcttgctccaacaccccaacatcttcgacgcaggt gtcgcaggtcttcccgacgatgacgccggtgaacttcccgccgccgttgttg ttttggagcacggaaagacgatgacggaaaaagagatcgtggattacgtcgc cagtcaagtaacaaccgcgaaaaagttgcgcggaggagttgtgtttgtggac gaagtaccgaaaggtcttaccggaaaactcgacgcaagaaaaatcagagaga tcctcataaaggccaagaagggcggaaagatcgccgtgtaattctactcttc ctgaatctagggctgtttcttttgggtttccacttatttattacgggtatt tatcttatttatttattttagtttttttttcttacttggaataataaagagt ctg | |

DETAILED DESCRIPTION

We herein describe that fat-derived exosomes carrying miRNA target the liver in vivo and can affect hepatic gene expression. Exogenous miRNA expressed in brown adipose tissue (BAT) regulates mRNA expression in liver. Fat-derived exosomes may therefore be a delivery systems suitable for small RNAs as well as small proteins. Furthermore, in order to add to the specificity and to possibly eliminate uptake from other tissues altogether, fat-derived exosomes can be modified by adding a dual ligand system which may be tethered to the exosomal membrane.

Definitions

"Adipose tissue" as used herein is equivalent to "fat" and may be used interchangeably. Adipose tissue refers to any tissue that is composed mainly of adipocytes. Adipose tissue includes white fat, beige fat, and brown fat.

"Exosomes" as used herein are membrane-surrounded, cell-derived vesicles that are present in many biological fluids, including blood, urine, and cultured medium of cell cultures. Exosomes may also be referred to as secreted vesicles.

"Lipodystrophy" as used herein refers to abnormal or degenerative conditions of the body's adipose tissue. As such, lipoatrophy (or loss of fat) is included in the definition of a lipodystrophy. Lipodystrophy may be congenital or may be secondary to a precipitating condition, such as human immunodeficiency (HIV) lipodystrophy.

"miRNA" as used herein refers to small non-coding RNA molecules that are evolutionary conserved. miRNAs are naturally occurring in an organism. Alternatively, a miRNA may be designed artificially and not be present in any organism. An miRNA may be chemically modified to improve stability. A miRNA may affect RNA silencing and post-transcriptional regulation of gene expression.

"Protein" as used herein, is a protein, polypeptide, or peptide. As such, a "protein" as used in this application may refer to only a portion of a full-length protein that is the product of a gene.

I. Compositions a. Exosomes

In some embodiments, the invention comprises exosomes comprising miRNA. In some embodiments, the exosomes further comprise a targeting moiety, wherein the targeting moiety is not native to the exosome.

In some embodiments, the exosomes are isolated from human or animal subjects. In some embodiments, the exosomes are produced by cells in vitro. In some embodiments, the isolated exosomes are formed inside the cell in compartments known as multivesicular endosomes (MVE) or multivesicular body (MVB). In some embodiments, exosomes are released from a cell without a trigger or signal. In some embodiments, exosomes are released from a cell based on a signal, such as binding of a cell-surface receptor. Exosomes may be harvested from a human or animal subject and engineered ex vivo to comprise on or more miRNA and/or one or more non-native targeting moiety.

In some embodiments, exosomes are approximately 30 to 100 nm, 20 to 90 nm, 30 to 80 nm, 40 to 70 nm, or 50 to 60 nm. In some embodiments, exosomes are approximately 30, 40, 50, 60, 70, 80, 90, 100, 110, 120, 130, 140, 150, or 200 nm in size.

In some embodiments, the exosome isolated from an in vivo or in vitro cell source is modified to increase or decrease its size, to comprises one or more targeting moieties, or to comprise one or more miRNA.

Sometimes, exosomes are internalized by the same cell from which they originated. In some embodiments, exosomes interact with cells that are not the cell from which they originated. In some embodiments, exosomes are internalized by a cell that is different than the one from which they originated. In some embodiments, exosomes are vesicles for transfer of materials between cells. In some embodiments, exosomes are vesicles for transfer of materials between tissues or organs based on movement through the blood. In some embodiments, exosomes secreted by fat can travel through the blood and be taken up by the liver.

In some embodiments, exosomes play active roles in intercellular communication. In some embodiments, exosomes enable cell-cell crosstalk. In some embodiments, exosomes contain membrane-bound molecules essential for cell-to-cell signaling. In some embodiments, exosomes contain functional immune agents.

1. Fat-Derived Exosomes

In some embodiments, the exosome compositions of the invention are derived from adipose tissue. In some embodiments, exosomes secreted from fat or adipose tissue may be termed fat-derived exosomes. In some embodiments, this adipose tissue can be inguinal, epididymal, or brown adipose tissue (BAT). In some embodiments, this adipose tissue can be brown fat, beige fat, or white fat.

In some embodiments, an exosome is derived from BAT tissue. In some embodiments, BAT is characterized by numerous small lipid droplets and a higher concentration of mitochondria compared with white fat. In some embodiments, BAT occurs in high concentrations in certain anatomical locations, such as between the shoulder blades, surrounding the kidneys, the neck and supraclavicular area, and along the spinal cord. In some embodiments, BAT occurs in the upper chest and neck, especially paravertebrally.

In some embodiments, exosomes derived from fat are taken up by the liver.

In some embodiments, circulating exosomal miRNAs are used for diagnosing disorders affecting fat mass and metabolism. In some embodiments, the disorders affecting fat mass and metabolism are obesity, cachexia, diabetes, and insulin resistance.

b. Targeting Moieties

"Targeting moieties" are molecules that have specific binding or affinity for a particular molecular target. In some embodiments, a targeting moiety is conjugated to an exosome, wherein the targeting moiety acts as a guide for that exosome to travel to an organ, tissue, or cell that comprises the molecular target. In some embodiments, targeting moieties and/or molecular target may be proteins. In some embodiments, molecular targets may be proteins, such receptors expressed on the cell surface of tissues or organs. In some embodiments, targeting moieties may be a full-length or fragment of a ligand for a cell surface receptor. In some embodiments, the targeting moiety is not native to the exosome, i.e., the targeting moiety is not found on the exosome in nature and is added to the exosome.

In some embodiments, the targeting moiety is expressed on the surface of the exosome. In some embodiments, the targeting moiety is a transmembrane protein. In some embodiments, the targeting moiety is internally expressed and becomes expressed on the surface of the exosome after a targeting event.

An exosome which has been conjugated to a targeting moiety may be referred to herein as a "conjugated exosome."

In some embodiments, conjugated exosomes are taken up by cells in a target tissue based on a specific interaction of the targeting moiety with a molecular target in the target tissue.

In some embodiments, the molecular target is chosen based on its pattern of tissue expression. In some embodiments, the molecular target has high expression in some tissues, with substantially lower expression in other tissues. In some embodiments, the molecular target has high expression in only one tissue. In some embodiments, the molecular target is chosen to direct an exosome to a specific target tissue(s). In some embodiments, this specific target tissue is liver, brain, muscle, bone, heart, brain, kidney, lung, placenta, peripheral neurons, kidney or tumors of a variety of types.

In some embodiments, the molecular target has widespread expression. In some embodiments, the molecular target is expressed in more than one target tissue. In some embodiments, the molecular target is used to produce widespread delivery of exosomes to a variety or organs and tissues.

TABLE 9

Example of Exosomal Targeting Moieties, Target Tissues, and Engineered Exosomal Priming

| Target Tissue of Exosomes | Molecular Target in Target Tissue | Targeting Moiety Conjugated to Exosome | Exosomal Priming |
|---|---|---|---|
| Liver (normal) | N-acetylgalactosamine (Gal-N-Ac) surface protein in liver | Asialoglycoprotein Receptor (ASGPR) conjugated to myristoylated TyA sequence to ensure sorting into exosomes | miR-122, miR-19a, miR-19b, miR-192,and miR-128-3p and administer them into patients with |
| Liver (overrepresented in liver in conditions of non-alcoholic fatty liver disease-NAFLD) | Toll-Like Receptor 4 (TLR-4) | Toll-Like Receptor 4 ligand (TLR-4 ligand) conjugated to myristoylated TyA sequence to ensure sorting into exosomes | non alcoholic fatty liver disease. |
| Liver (hepatocellular carcinoma) | Alpha Fetoprotein (AFP) | Alpha Fetoprotein Receptor (Recaf) conjugated to myristoylated TyA | inhibitors of miRNAs (antagomirs) for miR-16, miR- |

TABLE 9-continued

Example of Exosomal Targeting Moieties, Target Tissues, and Engineered Exosomal Priming

| Target Tissue of Exosomes | Molecular Target in Target Tissue | Targeting Moiety Conjugated to Exosome | Exosomal Priming |
|---|---|---|---|
| | | sequence to ensure sorting into exosomes | 34a, miR-122, RNAi against Cyclin G1 and PAK4 |
| Brain (normal) | DNER (Delta/Notch-like EGF-related receptor) | Notch Receptor conjugated to myristoylated TyA sequence to ensure sorting into exosomes | miR-155 targeting α-synuclein, or RNAi against α-synuclein |
| Brain (overrepresented in brain in conditions of neurodegenerative diseases) | Adenosine A2A receptor | CGS-21680 Receptor analogue conjugated to myristoylated TyA sequence to ensure sorting into exosomes | |
| Kidney (normal) | Parathyroid Hormone 1 (PTH-1) | Parathyroid hormone receptor 1 (PTHR1) conjugated to myristoylated TyA sequence to ensure sorting into exosomes | miR-17 targeting PKD-2 in patients with polycystic kidney disease |
| Kidney (overrepresented in kidney in conditions of glomerulonephritis) | Neurotactin (CX3CL1) | Fractalkine receptor (CX3CR1) conjugated to myristoylated TyA sequence to ensure sorting into exosomes | |

Additional targeting moieties and molecular targets are known to those skilled in the art, and the present invention is not limited by the specific choice of targeting moiety(ies) and target(s).

In some embodiments, the targeting moiety is a ligand that binds to membrane receptors at the target. In some embodiments, the targeting moiety is one or more of Asialoglycoprotein Receptor (ASGPR), Toll-Like Receptor 4 ligand (TLR-4 ligand), Notch, CGS-21680, Parathyroid hormone receptor 1 (PTHR1), and Fractalkine receptor (CX3CR1).

In some embodiments, antibody targeting is comprised. In some embodiments, antibodies bind to specific cell surface proteins.

In some embodiments, the GalNAc ligand and the TLR4 ligand are proceeded by a TyA myristoylated peptide to target these proteins into the MVB and to the produced exosomes.

In some embodiments, the targeting moiety(ies) are expressed on the surface of the exosome by expressing a targeting moiety as a fusion protein together with an exosomal transmembrane protein, as described in WO2013084001. In some embodiments, the fusion protein is incorporated into the exosome as it is formed based on the known association of the exosomal transmembrane protein with exosomes.

In some embodiments, more than one targeting moiety is used.

In some embodiments, exosomes are used that lack targeting moieties.

c. Contents of Exosomes

Exosomes can act as messenger molecules that transport materials from one tissue to another. In some embodiments, naturally-occurring exosomes comprise proteins, lipids, and genetic material. In some embodiments, the genetic material is RNA or DNA. In some embodiments, exosomes contain cytoplasm and cytoplasmic contents of the cell from which they were secreted.

In some embodiments, exosomes are used to deliver exogenous cargo. In some embodiments, exosomes are used as a delivery system. In some embodiments, exosomes are used as a delivery system for therapeutic agents.

In some embodiments, the cargo delivered by exosomes is a nucleic acid. In some embodiments, the nucleic acid may comprise one or more chemical modifications that improve the stability of the nucleic acid. In some embodiments, the nucleic acid is a small interfering RNA (siRNA), short hairpin (shRNA), or micro RNA (miRNA). In some embodiments, the nucleic acid is miRNA. In some embodiments, the nucleic acid is long noncoding RNA (LNCRNA). In some embodiments, the LNCRNA is longer than 200 nucleotides. In some embodiments, the RNA is less than 200, 300, 400, 500, 600, 700, 800, 900, 1000, 2000, or 3000 nucleotides.

In some embodiments, the miRNA comprises a native sequence that is present in the subject organism. In some embodiments, the miRNA does not comprise a native sequence. In some embodiments, the miRNA is non-natural.

In some embodiments, the miRNA is non-naturally prepared ex vivo. In some embodiments, the miRNA alters gene function.

In some embodiments, exosomes are loaded in vitro. In some embodiments, exosomes are loaded by electroporation in vitro. In some embodiments, electroporation loads exosomes with non-natural RNA interference or proteins.

In some embodiments, fat-derived exosomes facilitate delivery of targeting moieties to diseased tissues in order to knockdown critical genes in disease pathology or pathogenesis. In some embodiments, fat-derived exosomes knockdown fibrosis genes in the diseased liver. In some embodiments, fat-derived exosomes knockdown genes contributing to the growth of cancers or tumor cells.

In some embodiments, exosomes are loaded with clustered regularly interspaced short palindromic repeats (CRISPR) and CRISPR associated proteins (Cas). In some embodiments, the Cas is Cas9. In some embodiments, the exosome is loaded with RNA and CRISPR-Cas9 proteins as part of a ribonucleoprotein complex. In some embodiments, the CRISPR-Cas9 ribonucleoprotein complex can regulate gene editing. In some embodiments, the CRISPR-Cas9 ribonuclear complex comprises a guide RNA sequence that targets a specific location in the subject's genome. In some embodiments, the guide RNA of the CRISPR-Cas9 targets specific cells and specific genomic regions.

In some embodiments, designer exosomes, also known as custom engineered exosomes, are comprised. In some embodiments, designer exosomes comprise exosomes with custom RNA cargo. In some embodiments, exosomes are transfected, a process that may be termed "exofection". In some embodiments, a commercially available exofection system is used, for example the Exo-Fect (SBI) or XMIR (BioCat) systems.

In some embodiments, designer exosomes are developed using commercially systems to package a protein of interest. In some embodiments, designer exosomes are generated using the XPack™ exosome protein engineering system (SBI). In some embodiments, a specific peptide sequence targets a protein of interest to the interior exosomal membrane allowing the fusion protein to be packaged into exosomes.

II. Methods and Uses a. Preparation of Fat-Derived Exosomes

In some embodiments, autologous exosomes are prepared. "Autologous exosomes" refers to exosomes that are prepared from the same subject who would receive the exosomes after ex vivo manipulation.

In some embodiments, exosomes are prepared from adipose tissue. In some embodiments, exosomes are prepared from BAT or WAT. In some embodiments, BAT or WAT adipocytes and precursors can be isolated from surgical or needle biopsies and used in vitro following transfection with a miRNA expressing vector. In some embodiments, the isolated exosomes are readministered or the adipocytes or preadipocytes transplanted back into patients for in vivo administration.

b. Use of Fat-Derived Exosomes as Treatments

In some embodiments, heterologous exosomes are prepared. "Heterologous exosomes" refer to exosomes that are prepared from a different individual than the subject who receives the exosomes after ex vivo manipulation.

In some embodiments, the subject who receives heterologous exosomes is a subject with a disease, disorder, or condition. In some embodiments, administration of heterologous exosomes is a treatment for a disease, disorder, or condition.

In some embodiments, administration of heterologous exosomes is a treatment for a lipodystrophy. In some embodiments, administration of heterologous exosomes is a treatment for HIV lipodystrophy or CGL.

In some embodiments, administration of heterologous exosomes alters the miRNA profile of subjects with a lipodystrophy. In some embodiments, administration of heterologous exosomes alters the miRNA profile of subjects with HIV lipodystrophy or CGL.

In some embodiments, administration of heterologous exosomes is used as a treatment for a metabolic disorder. In some embodiments, the metabolic disorder is fatty liver disease.

c. Packaging of miRNA into Fat-Derived Exosomes miRNAs and other related RNAs, including mRNAs, may be packaged into fat-derived exosomes in a number of ways. In some embodiments, commercially available motifs can be used to package miRNA into exosomes, such as XMotif (System Biosciences).

In some embodiments, exosomes are loading with miRNA and other related RNAs, including mRNAs using electroporation. In some embodiments, a Biorad Gene Pulser (Biorad, Hercules, Calif.) or similar system is used for electroporation of exosomes.

d. Delivery of miRNA to a Subject by an Exosome Delivery System

In some embodiments, fat-derived exosomes can be delivered by intravenous, intraperitoneal, or subcutaneous injection. In some embodiments, the fat-derived exosomes are delivered parenterally, orally, buccally, transdermally, via sonophoresis, or via inhalation. In some embodiments, the parenteral administration is subcutaneous, intramuscular, intrasternal, or intravenous injection.

In some embodiments, fat-derived exosomes can be used for delivery of miRNA. In some embodiments, fat-derived exosomes can be used as an exosome delivery system.

In some embodiments, fat-derived exosomes can be used as an exosome delivery system to the liver. In some embodiments, fat-derived exosomes are taken up by the liver. In some embodiments, fat-derived exosomes are taken up preferentially by the liver compared to uptake by other organs. In some embodiments, the majority of fat-derived exosomes that are administered are taken up by the liver. In some embodiments, fat-derived exosomes are taken up by the liver, but may be taken up by additional organs or tissues, including tumor tissues.

In some embodiments, delivery of miRNA by an exosome delivery system is of use in treating a disease or condition. In some embodiments, the miRNA affects the expression and/or function of a protein. In some embodiments, the change in expression and/or function of a protein can be measured be any of wide range of assays known to those skilled in the art, such as changes in mRNA levels, changes in protein levels, changes in serum or plasma protein protein concentrations, changes in protein function, changes in cellular function, changes in tissue function, or changes in diagnostic tests performed in a whole subject.

In some embodiments, delivery of mir99b by an exosome delivery system can decrease expression of fibroblast growth factor 21 (FGF21).

In some embodiments, changes in expression of FGF21 following administration of mir99b by an exosomal delivery system can improve profiles of glucose and lipid metabolism, insulin sensitivity, obesity, glucose homeostasis, type 1 or type 2 diabetes, dyslipidemia, non-alcoholic fatty liver disease. FGF21 has been shown to have a broad range of effects on metabolism.

e. Target Tissue Specific Effects After Administration of Conjugated Exosomes

In some embodiments, choosing a molecular target and conjugating a corresponding targeting moiety to exosomes leads to tissue-specific delivery of exosomes. In some embodiments, choosing a molecular target and conjugating a corresponding targeting moiety to exosomes leads to relatively high uptake of conjugated exosomes by a target tissue(s), with lower uptake by other tissues. In some embodiments, choosing a molecular target and conjugating a corresponding targeting moiety to exosomes leads to exosomes being taken up at a lower rate by non-target tissues versus target tissues.

In some embodiments, administration of conjugated exosomes causes effects specifically in the target tissue. In some embodiments, administration of conjugated exosomes causes effects that are higher in the target tissue compared to other tissues. In some embodiments, administration of conjugated exosomes does not elicit an effect in non-target tissues.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

EXAMPLES

The following examples are provided to illustrate certain disclosed embodiments and are not to be construed as limiting the scope of this disclosure in any way.

Example 1—Identification of Adipose Tissue as a Major Source of Circulating Exosomal miRNAs To better understand the role of miRNAs in fat, mice were generated specifically lacking Dicer in adipose tissue using Cre-lox mediated gene recombination (FIG. 1a)[13]. These ADicerKO mice exhibited a generalized defect in miRNA processing in adipose tissue, which resulted in a marked reduction of WAT, whitening of BAT, insulin resistance with hyperinsulinemia, and altered circulating lipids[14].

To determine to what extent adipose tissue contributes to circulating miRNAs, exosomes were isolated from sera of ADicerKO and control mice by differential ultracentrifugation[15]. These vesicles were 80-200 nm in diameter[16] (FIG. 6a) and stained for the exosomal markers CD63 and CD9 (FIG. 1b)[17,18]; the number of exosomes isolated from ADicerKO and control mice was comparable (FIGS. 6b and 6c). qPCR profiling of the serum exosomes for 709 known murine miRNAs revealed 653 detectable miRNAs (defined as CT<34). Compared to control, ADicerKO mice exhibited significant alterations in 422 (65.7%) circulating miRNAs. Of these, only 3 miRNAs had a significant increase, while 419 had significant decreases (FIGS. 1c-d, 6d and Table 1) with 88% reduced by >4-fold, suggesting that adipose tissue is a major source of circulating exosomal miRNAs.

Figure 6D:
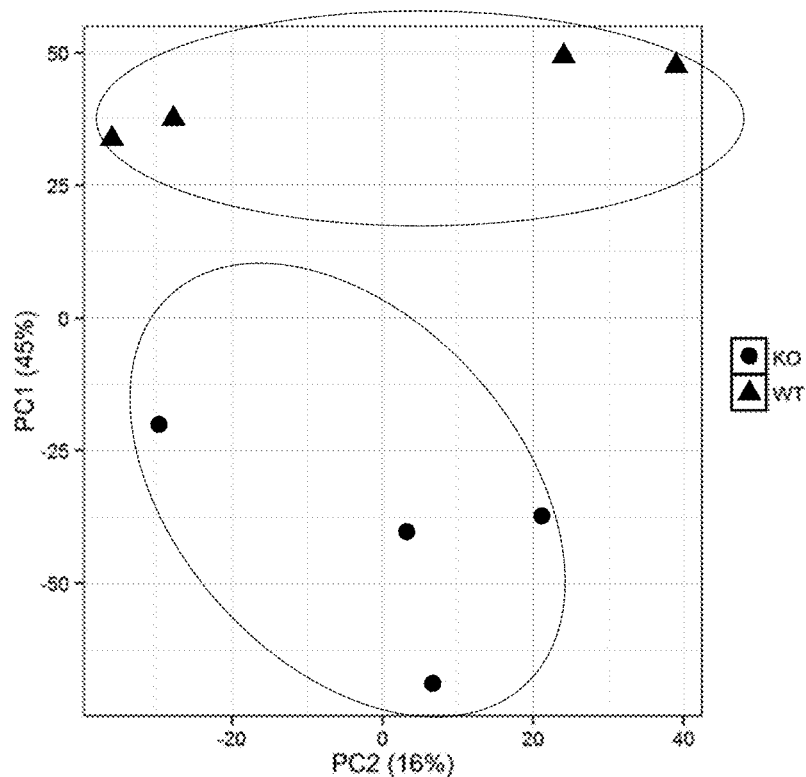

FIG. 6d shows principal component analysis (PCA) of data from ADicerKO and wild-type mice for data decomposition of exosomal miRNA qPCR experiments. These data indicate that different trends were seen for KO and wild-type mice. The axes represent the fraction of total detected miRNAs in the component indicated.

Figure 6E:
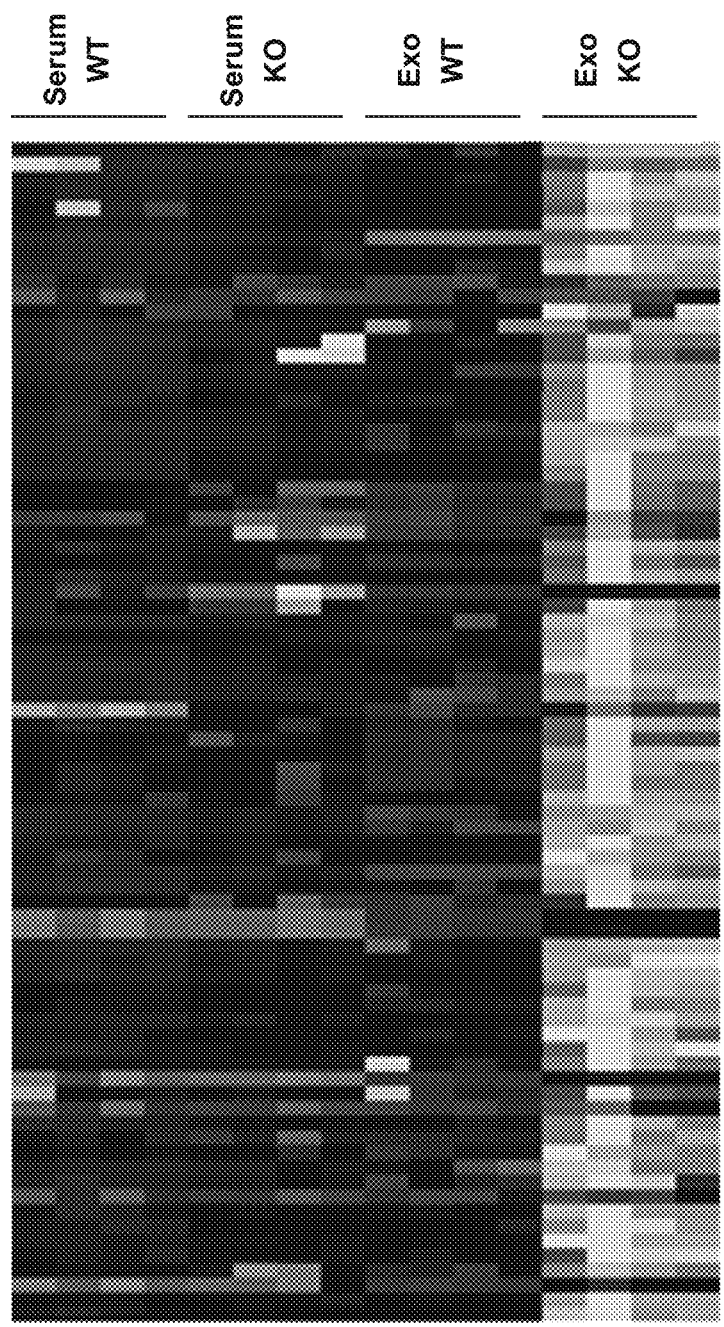

Consistent with this, among these most reduced miRNAs (Table 1), many have been previously identified as highly expressed in fat, including miR-221, miR-201, miR-222 and miR-16[9,19,20]. This phenomenon is cell autonomous and could be reproduced in vitro. Thus, brown preadipocytes isolated from Dicer-floxed animals and recombined by transduction with Ad-Cre exhibited marked reductions in almost all of the exosomal miRNAs released in culture supernatants when compared to control Ad-GFP transduced cells (FIG. 6e).

TABLE 1

Exosomal miRNA significantly decreased in sera of ADicerKO mice compared to control mice.

| miRNA | WTvsKO p-value | WTvsKO logFC | WTvsKO FC | WTvsKO FDR |
|---|---|---|---|---|
| mmu-miR-743b-3p | 0.021 | −4.353 | −20.428 | 0.042 |
| mmu-miR-2146 | 0.046 | −1.803 | −3.488 | 0.078 |
| mmu-miR-2138 | 0.043 | −1.393 | −2.625 | 0.074 |
| mmu-miR-760 | 0.040 | 1.155 | 2.227 | 0.071 |
| mmu-miR-1962 | 0.042 | 1.193 | 2.285 | 0.073 |
| mmu-miR-1945 | 0.030 | 1.233 | 2.350 | 0.056 |
| mmu-let-7g* | 0.049 | 1.238 | 2.358 | 0.083 |
| mmu-miR-16 | 0.024 | 1.283 | 2.433 | 0.047 |
| mmu-miR-434-5p | 0.029 | 1.303 | 2.467 | 0.055 |
| mmu-miR-376a* | 0.027 | 1.348 | 2.545 | 0.051 |
| mmu-miR-1190 | 0.027 | 1.383 | 2.607 | 0.052 |
| mmu-miR-1895 | 0.024 | 1.388 | 2.616 | 0.047 |
| mmu-miR-547 | 0.040 | 1.473 | 2.775 | 0.071 |
| mmu-miR-466j | 0.045 | 1.488 | 2.804 | 0.078 |
| mmu-miR-485* | 0.034 | 1.500 | 2.828 | 0.063 |
| mmu-miR-145 | 0.013 | 1.543 | 2.913 | 0.029 |
| mmu-miR-543 | 0.011 | 1.615 | 3.063 | 0.027 |
| mmu-miR-1199 | 0.019 | 1.615 | 3.063 | 0.039 |
| mmu-miR-378* | 0.011 | 1.625 | 3.084 | 0.027 |
| mmu-miR-342-3p | 0.008 | 1.648 | 3.133 | 0.022 |
| mmu-miR-181c | 0.010 | 1.648 | 3.133 | 0.026 |
| mmu-miR-710 | 0.050 | 1.655 | 3.149 | 0.084 |
| mmu-miR-17* | 0.026 | 1.658 | 3.155 | 0.050 |
| mmu-miR-190 | 0.010 | 1.665 | 3.171 | 0.026 |
| mmu-miR-24-2* | 0.039 | 1.668 | 3.177 | 0.070 |
| mmu-miR-1971 | 0.036 | 1.680 | 3.204 | 0.065 |
| mmu-miR-330 | 0.008 | 1.685 | 3.215 | 0.022 |
| mmu-miR-152 | 0.018 | 1.688 | 3.221 | 0.037 |
| mmu-miR-30a | 0.006 | 1.713 | 3.277 | 0.018 |
| mmu-miR-1967 | 0.018 | 1.718 | 3.289 | 0.038 |
| mmu-miR-1959 | 0.019 | 1.720 | 3.294 | 0.039 |
| mmu-miR-338-3p | 0.029 | 1.725 | 3.306 | 0.055 |
| mmu-miR-222 | 0.007 | 1.735 | 3.329 | 0.022 |
| mmu-miR-223 | 0.008 | 1.758 | 3.381 | 0.022 |
| mmu-miR-23a | 0.006 | 1.765 | 3.399 | 0.019 |
| mmu-miR-1907 | 0.025 | 1.768 | 3.405 | 0.049 |
| mmu-miR-351 | 0.004 | 1.805 | 3.494 | 0.015 |
| mmu-miR-291b-5p | 0.017 | 1.808 | 3.500 | 0.036 |
| mmu-miR-211 | 0.011 | 1.813 | 3.513 | 0.027 |
| mmu-miR-23b | 0.003 | 1.815 | 3.519 | 0.011 |
| mmu-miR-501-3p | 0.003 | 1.818 | 3.525 | 0.012 |
| mmu-miR-467b | 0.009 | 1.850 | 3.605 | 0.024 |
| mmu-miR-181d | 0.044 | 1.860 | 3.630 | 0.077 |
| mmu-miR-488 | 0.034 | 1.865 | 3.643 | 0.063 |
| mmu-miR-1947 | 0.010 | 1.883 | 3.687 | 0.025 |
| mmu-miR-15b | 0.003 | 1.885 | 3.694 | 0.012 |
| mmu-miR-574-3p | 0.009 | 1.890 | 3.706 | 0.024 |
| mmu-miR-683 | 0.020 | 1.905 | 3.745 | 0.040 |
| mmu-miR-200a* | 0.011 | 1.933 | 3.817 | 0.027 |
| mmu-miR-1955 | 0.029 | 1.958 | 3.884 | 0.055 |
| mmu-miR-1894-5p | 0.011 | 1.965 | 3.904 | 0.027 |
| mmu-miR-1981 | 0.017 | 1.980 | 3.945 | 0.037 |
| mmu-miR-423-3p | 0.005 | 1.993 | 3.979 | 0.016 |
| mmu-miR-92a | 0.005 | 2.005 | 4.014 | 0.017 |
| mmu-miR-10a | 0.007 | 2.005 | 4.014 | 0.021 |
| mmu-miR-25 | 0.003 | 2.010 | 4.028 | 0.011 |
| mmu-miR-713 | 0.007 | 2.013 | 4.035 | 0.020 |
| mmu-miR-30d | 0.001 | 2.028 | 4.077 | 0.007 |
| mmu-miR-7a* | 0.025 | 2.038 | 4.105 | 0.049 |
| mmu-miR-532-3p | 0.017 | 2.045 | 4.127 | 0.037 |

TABLE 1-continued

Exosomal miRNA significantly decreased in sera of ADicerKO mice compared to control mice.

| miRNA | WTvsKO p-value | WTvsKO logFC | WTvsKO FC | WTvsKO FDR |
|---|---|---|---|---|
| mmu-miR-467d* | 0.018 | 2.045 | 4.127 | 0.038 |
| mmu-miR-678 | 0.003 | 2.050 | 4.141 | 0.011 |
| mmu-miR-763 | 0.007 | 2.053 | 4.148 | 0.021 |
| mmu-miR-30c | 0.003 | 2.055 | 4.155 | 0.011 |
| mmu-miR-139-5p | 0.001 | 2.065 | 4.184 | 0.006 |
| mmu-miR-743b-5p | 0.015 | 2.073 | 4.206 | 0.034 |
| mmu-miR-700 | 0.010 | 2.075 | 4.213 | 0.026 |
| mmu-miR-34c | 0.003 | 2.095 | 4.272 | 0.012 |
| mmu-miR-221 | 0.035 | 2.108 | 4.309 | 0.064 |
| mmu-miR-666-5p | 0.004 | 2.113 | 4.324 | 0.013 |
| mmu-miR-143 | 0.005 | 2.123 | 4.354 | 0.018 |
| mmu-miR-106a | 0.001 | 2.143 | 4.415 | 0.007 |
| mmu-miR-329 | 0.004 | 2.148 | 4.431 | 0.014 |
| mmu-miR-599 | 0.005 | 2.158 | 4.461 | 0.018 |
| mmu-miR-299* | 0.002 | 2.178 | 4.524 | 0.009 |
| mmu-miR-466i | 0.002 | 2.185 | 4.547 | 0.010 |
| mmu-miR-489 | 0.002 | 2.190 | 4.563 | 0.010 |
| mmu-miR-1903 | 0.036 | 2.195 | 4.579 | 0.065 |
| mmu-miR-302c* | 0.011 | 2.200 | 4.595 | 0.027 |
| mmu-miR-19b | 0.001 | 2.205 | 4.611 | 0.007 |
| mmu-miR-378 | 0.001 | 2.210 | 4.627 | 0.007 |
| mmu-miR-466f | 0.024 | 2.213 | 4.635 | 0.047 |
| mmu-miR-1941-3p | 0.012 | 2.225 | 4.675 | 0.027 |
| mmu-miR-466f-3p | 0.002 | 2.235 | 4.708 | 0.009 |
| mmu-miR-330* | 0.019 | 2.235 | 4.708 | 0.039 |
| mmu-miR-877* | 0.007 | 2.250 | 4.757 | 0.022 |
| mmu-miR-218-2* | 0.042 | 2.253 | 4.765 | 0.073 |
| mmu-miR-216a | 0.011 | 2.258 | 4.782 | 0.027 |
| mmu-miR-669d | 0.009 | 2.260 | 4.790 | 0.024 |
| mmu-miR-33* | 0.012 | 2.260 | 4.790 | 0.028 |
| mmu-miR-691 | 0.009 | 2.268 | 4.815 | 0.024 |
| mmu-miR-467a* | 0.017 | 2.275 | 4.840 | 0.037 |
| mmu-miR-122 | 0.004 | 2.278 | 4.848 | 0.015 |
| mmu-miR-24 | 0.002 | 2.283 | 4.865 | 0.009 |
| mmu-miR-667 | 0.014 | 2.283 | 4.865 | 0.033 |
| mmu-miR-1934 | 0.008 | 2.288 | 4.882 | 0.023 |
| mmu-miR-93 | 0.001 | 2.290 | 4.891 | 0.006 |
| mmu-miR-770-5p | 0.023 | 2.300 | 4.925 | 0.045 |
| mmu-miR-669h-3p | 0.002 | 2.318 | 4.985 | 0.009 |
| mmu-miR-493 | 0.001 | 2.320 | 4.993 | 0.006 |
| mmu-miR-133b | 0.006 | 2.325 | 5.011 | 0.018 |
| mmu-miR-30b* | 0.017 | 2.330 | 5.028 | 0.036 |
| mmu-miR-200b | 0.031 | 2.335 | 5.046 | 0.058 |
| mmu-let-7a* | 0.006 | 2.338 | 5.054 | 0.019 |
| mmu-miR-669f | 0.008 | 2.338 | 5.054 | 0.022 |
| mmu-miR-193b | 0.001 | 2.348 | 5.089 | 0.007 |
| mmu-miR-130a | 0.001 | 2.355 | 5.116 | 0.006 |
| mmu-miR-764-5p | 0.008 | 2.358 | 5.125 | 0.023 |
| mmu-miR-30e | 0.001 | 2.360 | 5.134 | 0.006 |
| mmu-miR-484 | 0.001 | 2.373 | 5.178 | 0.007 |
| mmu-miR-15a* | 0.009 | 2.373 | 5.178 | 0.024 |
| mmu-miR-133a | 0.004 | 2.375 | 5.187 | 0.015 |
| mmu-miR-449c | 0.001 | 2.380 | 5.205 | 0.006 |
| mmu-miR-203 | 0.001 | 2.383 | 5.214 | 0.007 |
| mmu-miR-466f-5p | 0.004 | 2.390 | 5.242 | 0.014 |
| mmu-miR-666-3p | 0.013 | 2.395 | 5.260 | 0.030 |
| mmu-miR-1968 | 0.010 | 2.400 | 5.278 | 0.026 |
| mmu-miR-220 | 0.002 | 2.413 | 5.324 | 0.010 |
| mmu-miR-669n | 0.008 | 2.428 | 5.380 | 0.022 |
| mmu-miR-17 | 0.001 | 2.433 | 5.398 | 0.006 |
| mmu-miR-338-5p | 0.001 | 2.450 | 5.464 | 0.006 |
| mmu-miR-296-5p | 0.001 | 2.455 | 5.483 | 0.006 |
| mmu-miR-1982.1 | 0.017 | 2.470 | 5.540 | 0.036 |
| mmu-miR-30e* | 0.017 | 2.470 | 5.540 | 0.037 |
| mmu-miR-297a | 0.001 | 2.473 | 5.550 | 0.006 |
| mmu-miR-483* | 0.020 | 2.473 | 5.550 | 0.040 |
| mmu-miR-200c* | 0.003 | 2.483 | 5.589 | 0.011 |
| mmu-miR-546 | 0.000 | 2.485 | 5.598 | 0.005 |
| mmu-miR-327 | 0.002 | 2.488 | 5.608 | 0.009 |
| mmu-miR-721 | 0.044 | 2.488 | 5.608 | 0.077 |
| mmu-miR-20b | 0.000 | 2.490 | 5.618 | 0.005 |
| mmu-miR-27a | 0.001 | 2.490 | 5.618 | 0.005 |
| mmu-miR-126-3p | 0.001 | 2.500 | 5.657 | 0.006 |
| mmu-miR-335-3p | 0.001 | 2.505 | 5.676 | 0.006 |
| mmu-miR-22 | 0.001 | 2.523 | 5.746 | 0.005 |
| mmu-miR-692 | 0.001 | 2.523 | 5.746 | 0.007 |
| mmu-miR-205 | 0.000 | 2.528 | 5.766 | 0.005 |
| mmu-miR-10b | 0.001 | 2.530 | 5.776 | 0.005 |
| mmu-miR-339-3p | 0.001 | 2.565 | 5.918 | 0.007 |
| mmu-miR-15a | 0.001 | 2.573 | 5.948 | 0.006 |
| mmu-miR-126-5p | 0.009 | 2.573 | 5.948 | 0.024 |
| mmu-miR-124 | 0.001 | 2.575 | 5.959 | 0.005 |
| mmu-miR-1899 | 0.001 | 2.575 | 5.959 | 0.007 |
| mmu-miR-6691 | 0.010 | 2.580 | 5.979 | 0.025 |
| mmu-miR-1963 | 0.007 | 2.593 | 6.031 | 0.021 |
| mmu-miR-370 | 0.001 | 2.595 | 6.042 | 0.006 |
| mmu-miR-466e-3p | 0.021 | 2.610 | 6.105 | 0.042 |
| mmu-miR-452 | 0.001 | 2.615 | 6.126 | 0.006 |
| mmu-miR-705 | 0.001 | 2.615 | 6.126 | 0.007 |
| mmu-miR-466h | 0.006 | 2.623 | 6.158 | 0.019 |
| mmu-miR-540-3p | 0.000 | 2.630 | 6.190 | 0.004 |
| mmu-miR-19a | 0.001 | 2.633 | 6.201 | 0.007 |
| mmu-miR-99b | 0.008 | 2.640 | 6.233 | 0.023 |
| mmu-miR-451 | 0.000 | 2.645 | 6.255 | 0.004 |
| mmu-miR-346 | 0.001 | 2.650 | 6.277 | 0.005 |
| mmu-miR-544 | 0.006 | 2.695 | 6.476 | 0.019 |
| mmu-miR-375 | 0.000 | 2.698 | 6.487 | 0.004 |
| mmu-miR-494 | 0.001 | 2.703 | 6.509 | 0.007 |
| mmu-miR-345-5p | 0.000 | 2.715 | 6.566 | 0.004 |
| mmu-miR-29a | 0.001 | 2.715 | 6.566 | 0.006 |
| mmu-miR-1306 | 0.017 | 2.723 | 6.600 | 0.037 |
| mmu-miR-185 | 0.021 | 2.733 | 6.646 | 0.043 |
| mmu-miR-770-3p | 0.003 | 2.735 | 6.658 | 0.012 |
| mmu-miR-210 | 0.036 | 2.743 | 6.692 | 0.065 |
| mmu-miR-92b | 0.000 | 2.745 | 6.704 | 0.004 |
| mmu-miR-449a | 0.001 | 2.748 | 6.716 | 0.006 |
| mmu-miR-465b-5p | 0.009 | 2.750 | 6.727 | 0.024 |
| mmu-miR-129-5p | 0.000 | 2.753 | 6.739 | 0.004 |
| mmu-miR-206 | 0.004 | 2.763 | 6.786 | 0.013 |
| mmu-miR-463 | 0.018 | 2.763 | 6.786 | 0.038 |
| mmu-miR-582-3p | 0.001 | 2.770 | 6.821 | 0.006 |
| mmu-miR-155 | 0.003 | 2.770 | 6.821 | 0.011 |
| mmu-miR-381 | 0.003 | 2.770 | 6.821 | 0.012 |
| mmu-miR-297b-3p | 0.000 | 2.773 | 6.833 | 0.004 |
| mmu-miR-764-3p | 0.001 | 2.785 | 6.892 | 0.006 |
| mmu-miR-496 | 0.001 | 2.790 | 6.916 | 0.006 |
| mmu-miR-302d | 0.022 | 2.793 | 6.928 | 0.044 |
| mmu-miR-1964 | 0.001 | 2.795 | 6.940 | 0.006 |
| mmu-let-7f* | 0.006 | 2.800 | 6.964 | 0.019 |
| mmu-miR-429 | 0.001 | 2.803 | 6.976 | 0.006 |
| mmu-miR-377 | 0.026 | 2.805 | 6.989 | 0.050 |
| mmu-miR-290-5p | 0.014 | 2.810 | 7.013 | 0.032 |
| mmu-miR-21 | 0.001 | 2.818 | 7.049 | 0.006 |
| mmu-miR-487b | 0.001 | 2.828 | 7.098 | 0.006 |
| mmu-miR-184 | 0.003 | 2.828 | 7.098 | 0.012 |
| mmu-miR-21* | 0.002 | 2.835 | 7.135 | 0.009 |
| mmu-miR-685 | 0.000 | 2.838 | 7.148 | 0.005 |
| mmu-miR-654-3p | 0.009 | 2.838 | 7.148 | 0.023 |
| mmu-miR-449b | 0.000 | 2.848 | 7.198 | 0.005 |
| mmu-miR-669i | 0.019 | 2.848 | 7.198 | 0.039 |
| mmu-miR-28* | 0.010 | 2.860 | 7.260 | 0.025 |
| mmu-miR-505 | 0.000 | 2.865 | 7.285 | 0.005 |
| mmu-miR-151-3p | 0.000 | 2.868 | 7.298 | 0.005 |
| mmu-miR-30c-1* | 0.031 | 2.868 | 7.298 | 0.058 |
| mmu-let-7e | 0.003 | 2.873 | 7.323 | 0.012 |
| mmu-miR-1191 | 0.000 | 2.878 | 7.349 | 0.005 |
| mmu-miR-615-3p | 0.001 | 2.883 | 7.374 | 0.007 |
| mmu-miR-30b | 0.000 | 2.893 | 7.426 | 0.004 |
| mmu-miR-27b | 0.000 | 2.908 | 7.503 | 0.004 |
| mmu-miR-450a-3p | 0.005 | 2.918 | 7.555 | 0.017 |
| mmu-miR-1982* | 0.013 | 2.925 | 7.595 | 0.031 |
| mmu-miR-675-5p | 0.002 | 2.938 | 7.661 | 0.009 |
| mmu-let-7c | 0.002 | 2.938 | 7.661 | 0.010 |
| mmu-miR-669h-5p | 0.011 | 2.958 | 7.768 | 0.027 |
| mmu-miR-293* | 0.037 | 2.958 | 7.768 | 0.068 |
| mmu-miR-188-3p | 0.002 | 2.985 | 7.917 | 0.010 |
| mmu-miR-470 | 0.003 | 2.995 | 7.972 | 0.011 |
| mmu-miR-671-5p | 0.002 | 3.003 | 8.014 | 0.008 |

TABLE 1-continued

Exosomal miRNA significantly decreased in sera of ADicerKO mice compared to control mice.

| miRNA | WTvsKO p-value | WTvsKO logFC | WTvsKO FC | WTvsKO FDR |
|---|---|---|---|---|
| mmu-miR-468 | 0.006 | 3.010 | 8.056 | 0.018 |
| mmu-miR-501-5p | 0.018 | 3.010 | 8.056 | 0.038 |
| mmu-miR-201 | 0.000 | 3.013 | 8.070 | 0.004 |
| mmu-miR-20a | 0.000 | 3.020 | 8.112 | 0.004 |
| mmu-miR-207 | 0.000 | 3.020 | 8.112 | 0.004 |
| mmu-miR-197 | 0.004 | 3.023 | 8.126 | 0.015 |
| mmu-miR-432 | 0.001 | 3.028 | 8.154 | 0.007 |
| mmu-miR-696 | 0.000 | 3.035 | 8.196 | 0.004 |
| mmu-miR-686 | 0.000 | 3.040 | 8.225 | 0.004 |
| mmu-miR-31 | 0.000 | 3.043 | 8.239 | 0.004 |
| mmu-miR-698 | 0.002 | 3.055 | 8.311 | 0.008 |
| mmu-miR-668 | 0.000 | 3.075 | 8.427 | 0.004 |
| mmu-miR-26a | 0.001 | 3.088 | 8.500 | 0.006 |
| mmu-miR-31* | 0.030 | 3.098 | 8.559 | 0.057 |
| mmu-miR-215 | 0.040 | 3.103 | 8.589 | 0.071 |
| mmu-miR-92a* | 0.040 | 3.118 | 8.679 | 0.071 |
| mmu-miR-214 | 0.003 | 3.120 | 8.694 | 0.011 |
| mmu-let-7d | 0.001 | 3.140 | 8.815 | 0.006 |
| mmu-miR-466g | 0.000 | 3.143 | 8.831 | 0.005 |
| mmu-miR-107 | 0.045 | 3.148 | 8.861 | 0.077 |
| mmu-miR-29c | 0.000 | 3.150 | 8.877 | 0.004 |
| mmu-miR-18a | 0.010 | 3.155 | 8.907 | 0.026 |
| mmu-miR-99a | 0.000 | 3.160 | 8.938 | 0.003 |
| mmu-miR-455 | 0.003 | 3.175 | 9.032 | 0.012 |
| mmu-miR-665 | 0.000 | 3.198 | 9.174 | 0.005 |
| mmu-miR-431 | 0.015 | 3.203 | 9.206 | 0.033 |
| mmu-miR-326 | 0.002 | 3.208 | 9.237 | 0.008 |
| mmu-miR-34a | 0.001 | 3.210 | 9.254 | 0.005 |
| mmu-miR-350 | 0.000 | 3.213 | 9.270 | 0.003 |
| mmu-miR-295* | 0.018 | 3.213 | 9.270 | 0.038 |
| mmu-miR-467h | 0.007 | 3.215 | 9.286 | 0.022 |
| mmu-miR-367 | 0.023 | 3.220 | 9.318 | 0.045 |
| mmu-let-7b | 0.002 | 3.233 | 9.399 | 0.010 |
| mmu-miR-805 | 0.045 | 3.248 | 9.497 | 0.077 |
| mmu-miR-331-5p | 0.008 | 3.258 | 9.563 | 0.023 |
| mmu-miR-343 | 0.001 | 3.280 | 9.714 | 0.005 |
| mmu-miR-384-3p | 0.004 | 3.298 | 9.832 | 0.013 |
| mmu-miR-411 | 0.018 | 3.298 | 9.832 | 0.038 |
| mmu-miR-217 | 0.000 | 3.308 | 9.900 | 0.004 |
| mmu-miR-466d-3p | 0.001 | 3.308 | 9.900 | 0.007 |
| mmu-miR-1902 | 0.009 | 3.318 | 9.969 | 0.024 |
| mmu-miR-141* | 0.046 | 3.318 | 9.969 | 0.079 |
| mmu-miR-149 | 0.000 | 3.330 | 10.056 | 0.004 |
| mmu-miR-762 | 0.011 | 3.333 | 10.074 | 0.027 |
| mmu-miR-448 | 0.040 | 3.345 | 10.161 | 0.071 |
| mmu-miR-670 | 0.000 | 3.355 | 10.232 | 0.003 |
| mmu-miR-383 | 0.000 | 3.360 | 10.267 | 0.005 |
| mmu-miR-344 | 0.000 | 3.365 | 10.303 | 0.004 |
| mmu-miR-361 | 0.001 | 3.368 | 10.321 | 0.006 |
| mmu-miR-532-5p | 0.004 | 3.388 | 10.465 | 0.015 |
| mmu-miR-466b-3p | 0.007 | 3.403 | 10.574 | 0.021 |
| mmu-let-7i | 0.000 | 3.405 | 10.593 | 0.004 |
| mmu-miR-878-5p | 0.026 | 3.413 | 10.648 | 0.050 |
| mmu-miR-212 | 0.000 | 3.423 | 10.722 | 0.005 |
| mmu-miR-680 | 0.019 | 3.423 | 10.722 | 0.039 |
| mmu-miR-195 | 0.032 | 3.425 | 10.741 | 0.059 |
| mmu-miR-151-5p | 0.001 | 3.430 | 10.778 | 0.005 |
| mmu-miR-337-5p | 0.000 | 3.438 | 10.834 | 0.004 |
| mmu-miR-33 | 0.009 | 3.463 | 11.023 | 0.024 |
| mmu-miR-676 | 0.000 | 3.473 | 11.100 | 0.004 |
| mmu-miR-16* | 0.001 | 3.480 | 11.158 | 0.006 |
| mmu-miR-679 | 0.031 | 3.483 | 11.177 | 0.058 |
| mmu-miR-339-5p | 0.040 | 3.485 | 11.197 | 0.071 |
| mmu-miR-130b | 0.001 | 3.488 | 11.216 | 0.005 |
| mmu-miR-128 | 0.006 | 3.500 | 11.314 | 0.019 |
| mmu-miR-103 | 0.008 | 3.518 | 11.452 | 0.023 |
| mmu-miR-465c-5p | 0.003 | 3.525 | 11.511 | 0.012 |
| mmu-miR-26b | 0.038 | 3.540 | 11.632 | 0.069 |
| mmu-miR-342-5p | 0.050 | 3.540 | 11.632 | 0.083 |
| mmu-miR-490 | 0.013 | 3.543 | 11.652 | 0.031 |
| mmu-miR-186 | 0.001 | 3.545 | 11.672 | 0.005 |
| mmu-miR-702 | 0.000 | 3.550 | 11.713 | 0.004 |
| mmu-miR-467b* | 0.003 | 3.555 | 11.753 | 0.011 |
| mmu-miR-500 | 0.000 | 3.560 | 11.794 | 0.003 |
| mmu-miR-509-5p | 0.007 | 3.583 | 11.980 | 0.021 |
| mmu-miR-450b-3p | 0.044 | 3.585 | 12.000 | 0.077 |
| mmu-miR-1897-3p | 0.016 | 3.590 | 12.042 | 0.036 |
| mmu-miR-365 | 0.007 | 3.610 | 12.210 | 0.020 |
| mmu-miR-325 | 0.000 | 3.643 | 12.488 | 0.004 |
| mmu-miR-328 | 0.001 | 3.680 | 12.817 | 0.006 |
| mmu-miR-590-3p | 0.002 | 3.688 | 12.884 | 0.009 |
| mmu-miR-497 | 0.001 | 3.700 | 12.996 | 0.007 |
| mmu-miR-300 | 0.014 | 3.725 | 13.223 | 0.032 |
| mmu-miR-453 | 0.009 | 3.765 | 13.595 | 0.024 |
| mmu-miR-100 | 0.000 | 3.773 | 13.666 | 0.003 |
| mmu-miR-541 | 0.015 | 3.785 | 13.785 | 0.033 |
| mmu-miR-693-3p | 0.008 | 3.795 | 13.881 | 0.022 |
| mmu-miR-376c | 0.014 | 3.805 | 13.977 | 0.033 |
| mmu-miR-467f | 0.002 | 3.813 | 14.050 | 0.009 |
| mmu-miR-1198 | 0.002 | 3.823 | 14.148 | 0.009 |
| mmu-miR-382 | 0.000 | 3.835 | 14.271 | 0.004 |
| mmu-miR-18b | 0.001 | 3.838 | 14.296 | 0.006 |
| mmu-miR-423-5p | 0.000 | 3.875 | 14.672 | 0.005 |
| mmu-miR-1929 | 0.022 | 3.898 | 14.903 | 0.043 |
| mmu-miR-669j | 0.003 | 3.903 | 14.954 | 0.013 |
| mmu-miR-181a-1* | 0.038 | 3.935 | 15.295 | 0.069 |
| mmu-miR-465a-5p | 0.013 | 3.965 | 15.617 | 0.031 |
| mmu-miR-340-3p | 0.040 | 3.968 | 15.644 | 0.071 |
| mmu-miR-466b-5p | 0.024 | 3.993 | 15.917 | 0.048 |
| mmu-miR-101b | 0.011 | 4.005 | 16.056 | 0.027 |
| mmu-miR-140 | 0.000 | 4.008 | 16.083 | 0.003 |
| mmu-miR-299 | 0.000 | 4.015 | 16.167 | 0.005 |
| mmu-miR-96 | 0.016 | 4.028 | 16.308 | 0.036 |
| mmu-miR-134 | 0.000 | 4.048 | 16.536 | 0.005 |
| mmu-miR-471 | 0.004 | 4.048 | 16.536 | 0.015 |
| mmu-miR-434-3p | 0.000 | 4.080 | 16.912 | 0.004 |
| mmu-miR-302a | 0.010 | 4.095 | 17.089 | 0.025 |
| mmu-miR-297c | 0.001 | 4.108 | 17.238 | 0.005 |
| mmu-miR-142-5p | 0.006 | 4.133 | 17.539 | 0.020 |
| mmu-miR-384-5p | 0.009 | 4.150 | 17.753 | 0.024 |
| mmu-miR-29b | 0.014 | 4.168 | 17.970 | 0.032 |
| mmu-miR-467c | 0.045 | 4.198 | 18.347 | 0.077 |
| mmu-miR-374 | 0.008 | 4.200 | 18.379 | 0.023 |
| mmu-miR-693-5p | 0.025 | 4.225 | 18.700 | 0.049 |
| mmu-miR-188-5p | 0.000 | 4.233 | 18.798 | 0.003 |
| mmu-miR-147 | 0.005 | 4.263 | 19.193 | 0.017 |
| mmu-miR-28 | 0.004 | 4.268 | 19.260 | 0.015 |
| mmu-miR-682 | 0.031 | 4.283 | 19.461 | 0.058 |
| mmu-miR-485 | 0.001 | 4.285 | 19.495 | 0.006 |
| mmu-miR-200a | 0.009 | 4.288 | 19.528 | 0.024 |
| mmu-miR-291a-5p | 0.000 | 4.310 | 19.835 | 0.003 |
| mmu-miR-652 | 0.000 | 4.313 | 19.870 | 0.004 |
| mmu-miR-296-3p | 0.001 | 4.358 | 20.499 | 0.006 |
| mmu-miR-30c-2* | 0.008 | 4.385 | 20.894 | 0.022 |
| mmu-miR-199b | 0.008 | 4.423 | 21.444 | 0.023 |
| mmu-miR-101a* | 0.002 | 4.433 | 21.593 | 0.009 |
| mmu-miR-551b | 0.036 | 4.433 | 21.593 | 0.065 |
| mmu-miR-148b | 0.000 | 4.450 | 21.857 | 0.003 |
| mmu-miR-323-5p | 0.000 | 4.450 | 21.857 | 0.003 |
| mmu-miR-146a | 0.001 | 4.455 | 21.933 | 0.007 |
| mmu-miR-146b | 0.001 | 4.553 | 23.466 | 0.005 |
| mmu-miR-148a | 0.000 | 4.578 | 23.876 | 0.003 |
| mmu-miR-872 | 0.007 | 4.578 | 23.876 | 0.021 |
| mmu-miR-669g | 0.006 | 4.590 | 24.084 | 0.019 |
| mmu-miR-32 | 0.018 | 4.593 | 24.126 | 0.038 |
| mmu-miR-464 | 0.008 | 4.603 | 24.294 | 0.023 |
| mmu-miR-380-3p | 0.000 | 4.613 | 24.463 | 0.004 |
| mmu-miR-1933-3p | 0.012 | 4.613 | 24.463 | 0.028 |
| mmu-miR-1936 | 0.003 | 4.620 | 24.590 | 0.012 |
| mmu-miR-1898 | 0.009 | 4.625 | 24.675 | 0.024 |
| mmu-miR-191 | 0.005 | 4.648 | 25.063 | 0.016 |
| mmu-miR-1961 | 0.000 | 4.675 | 25.546 | 0.003 |
| mmu-miR-654-5p | 0.008 | 4.688 | 25.768 | 0.023 |
| mmu-miR-466b-3-3p | 0.029 | 4.688 | 25.768 | 0.055 |
| mmu-miR-467e | 0.033 | 4.710 | 26.173 | 0.060 |
| mmu-miR-669k | 0.004 | 4.720 | 26.355 | 0.015 |
| mmu-miR-542-5p | 0.036 | 4.730 | 26.538 | 0.065 |
| mmu-miR-483 | 0.000 | 4.750 | 26.909 | 0.004 |

TABLE 1-continued

Exosomal miRNA significantly decreased in sera of ADicerKO mice compared to control mice.

| miRNA | WTvsKO p-value | WTvsKO logFC | WTvsKO FC | WTvsKO FDR |
|---|---|---|---|---|
| mmu-miR-186* | 0.007 | 4.750 | 26.909 | 0.020 |
| mmu-miR-883b-5p | 0.001 | 4.763 | 27.143 | 0.006 |
| mmu-miR-345-3p | 0.014 | 4.805 | 27.954 | 0.033 |
| mmu-miR-802 | 0.015 | 4.855 | 28.940 | 0.034 |
| mmu-let-7a | 0.000 | 4.880 | 29.446 | 0.003 |
| mmu-miR-425 | 0.001 | 4.890 | 29.651 | 0.007 |
| mmu-miR-291b-3p | 0.000 | 4.898 | 29.805 | 0.004 |
| mmu-miR-34b-3p | 0.025 | 4.900 | 29.857 | 0.049 |
| mmu-miR-138 | 0.002 | 4.903 | 29.909 | 0.008 |
| mmu-miR-878-3p | 0.007 | 4.925 | 30.379 | 0.022 |
| mmu-miR-466e-5p | 0.000 | 4.948 | 30.856 | 0.005 |
| mmu-miR-433 | 0.000 | 4.963 | 31.179 | 0.003 |
| mmu-miR-139-3p | 0.001 | 5.020 | 32.447 | 0.007 |
| mmu-miR-433* | 0.041 | 5.028 | 32.616 | 0.073 |
| mmu-miR-101a | 0.000 | 5.058 | 33.301 | 0.005 |
| mmu-miR-706 | 0.027 | 5.063 | 33.417 | 0.051 |
| mmu-miR-410 | 0.001 | 5.093 | 34.119 | 0.005 |
| mmu-miR-491 | 0.015 | 5.103 | 34.356 | 0.033 |
| mmu-miR-125a-3p | 0.002 | 5.113 | 34.595 | 0.008 |
| mmu-miR-466a-3p | 0.017 | 5.113 | 34.595 | 0.037 |
| mmu-miR-218-1* | 0.047 | 5.168 | 35.940 | 0.080 |
| mmu-miR-412 | 0.003 | 5.208 | 36.950 | 0.012 |
| mmu-let-7i* | 0.049 | 5.220 | 37.271 | 0.083 |
| mmu-miR-363 | 0.003 | 5.235 | 37.661 | 0.011 |
| mmu-let-7f | 0.004 | 5.258 | 38.253 | 0.013 |
| mmu-miR-695 | 0.010 | 5.285 | 38.989 | 0.025 |
| mmu-miR-290-3p | 0.016 | 5.310 | 39.671 | 0.036 |
| mmu-miR-697 | 0.012 | 5.313 | 39.739 | 0.028 |
| mmu-miR-380-5p | 0.000 | 5.355 | 40.928 | 0.005 |
| mmu-miR-883b-3p | 0.002 | 5.453 | 43.789 | 0.010 |
| mmu-miR-323-3p | 0.000 | 5.455 | 43.865 | 0.003 |
| mmu-miR-568 | 0.003 | 5.480 | 44.632 | 0.012 |
| mmu-miR-298 | 0.014 | 5.625 | 49.351 | 0.033 |
| mmu-miR-202-3p | 0.001 | 5.755 | 54.004 | 0.006 |
| mmu-miR-148a* | 0.011 | 5.840 | 57.282 | 0.027 |
| mmu-miR-294 | 0.002 | 5.843 | 57.381 | 0.009 |
| mmu-miR-322 | 0.001 | 5.858 | 57.981 | 0.005 |
| mmu-miR-129-3p | 0.002 | 5.878 | 58.790 | 0.008 |
| mmu-miR-302b | 0.002 | 5.910 | 60.129 | 0.010 |
| mmu-miR-409-5p | 0.000 | 6.000 | 64.000 | 0.003 |
| mmu-miR-337-3p | 0.002 | 6.020 | 64.893 | 0.009 |
| mmu-miR-376a | 0.001 | 6.023 | 65.006 | 0.007 |
| mmu-miR-141 | 0.015 | 6.055 | 66.487 | 0.033 |
| mmu-miR-466c-3p | 0.004 | 6.078 | 67.532 | 0.015 |
| mmu-miR-196a | 0.003 | 6.085 | 67.884 | 0.012 |
| mmu-miR-292-5p | 0.001 | 6.100 | 68.594 | 0.006 |
| mmu-miR-671-3p | 0.012 | 6.250 | 76.109 | 0.028 |
| mmu-miR-431* | 0.045 | 6.263 | 76.772 | 0.077 |
| mmu-miR-136 | 0.005 | 6.310 | 79.341 | 0.016 |
| mmu-miR-653 | 0.009 | 6.348 | 81.431 | 0.024 |
| mmu-miR-1 | 0.002 | 6.363 | 82.282 | 0.010 |
| mmu-miR-194 | 0.020 | 6.373 | 82.854 | 0.040 |
| mmu-miR-687 | 0.042 | 6.725 | 105.786 | 0.073 |
| mmu-miR-340-5p | 0.009 | 6.748 | 107.448 | 0.024 |
| mmu-miR-127 | 0.000 | 6.823 | 113.182 | 0.004 |
| mmu-miR-362-5p | 0.020 | 7.180 | 145.009 | 0.040 |
| mmu-miR-135b | 0.006 | 7.325 | 160.341 | 0.019 |
| mmu-miR-689 | 0.001 | 7.413 | 170.367 | 0.006 |
| mmu-miR-208a | 0.012 | 8.055 | 265.948 | 0.027 |
| mmu-miR-98 | 0.000 | 8.670 | 407.315 | 0.003 |
| mmu-miR-324-5p | 0.000 | 8.815 | 450.380 | 0.003 |
| mmu-miR-421 | 0.002 | 9.043 | 527.307 | 0.010 |
| mmu-miR-320 | 0.000 | 9.743 | 856.613 | 0.005 |
| mmu-miR-295 | 0.005 | 11.573 | 3045.577 | 0.018 |
| mmu-miR-183 | 0.001 | 11.580 | 3061.451 | 0.006 |
| mmu-miR-615-5p | 0.026 | 13.880 | 15076.354 | 0.050 |

FDR = false discovery rate, "*" indicates star species miRNA, in which the 3'-5' fragment induces the repression.

Figure 6F:
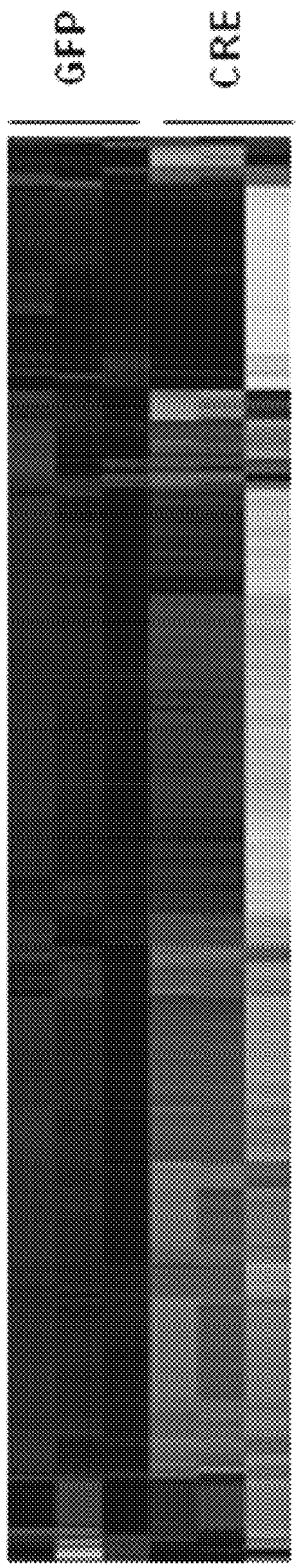
Figure 6G:
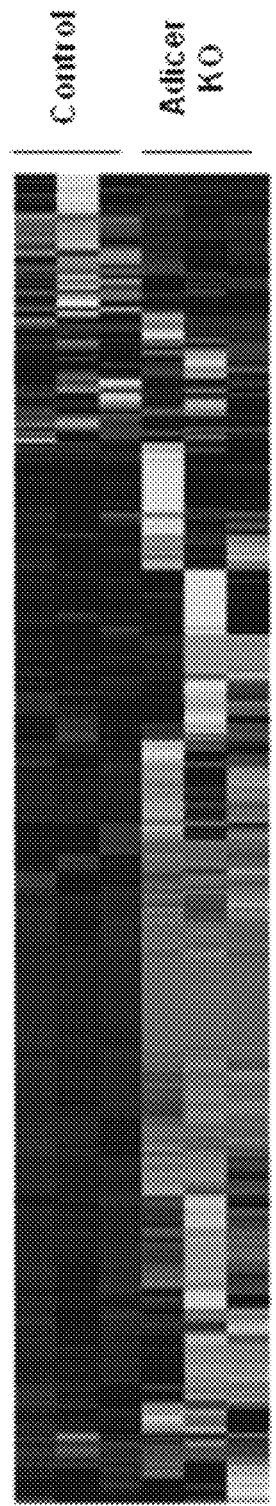
Figure 6I:
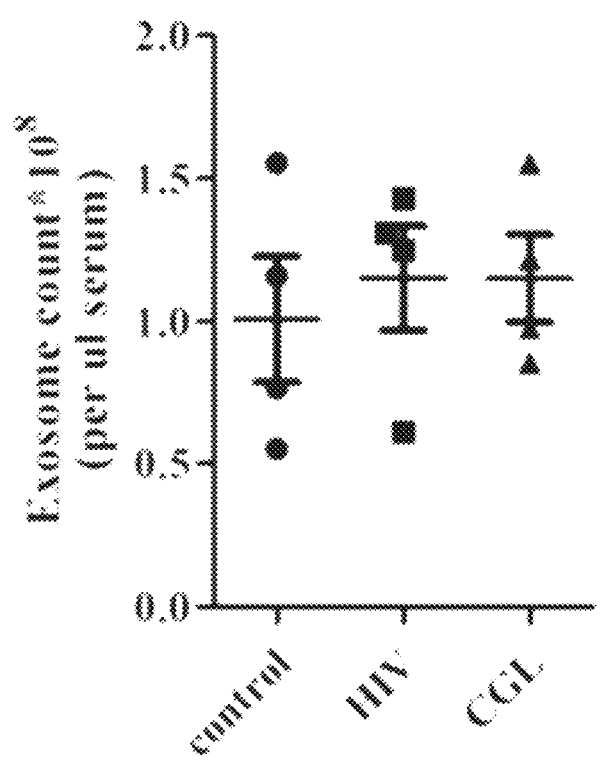
Figure 6J:
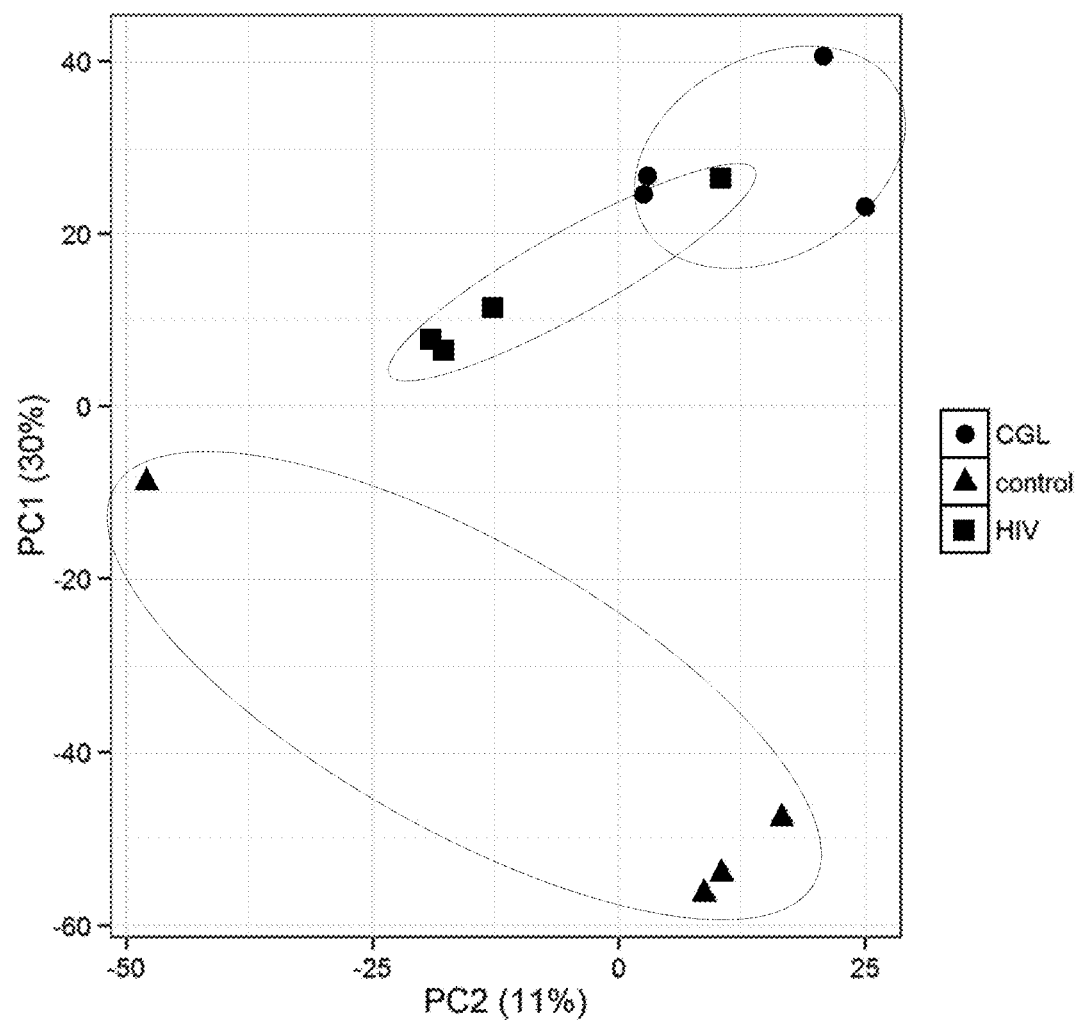

To determine if circulating exosomal miRNAs in humans might also originate from fat, exosomal miRNA profiling was performed on sera from patients with congenital generalized lipodystrophy (CGL) and patients with HIV-related lipodystrophy, who have previously been shown to have decreased levels of Dicer in adipose tissue[14] (details in FIG. 6f). FIG. 6f shows expression of exosomal miRNAs from culture supernatant of Dicer$^{fl/fl}$ preadipocytes transduced with Ad-GFP (GFP) or Ad-CRE (CRE). Isolation yielded similar exosome numbers from both controls and lipodystrophic patients (6h, with subject groups described in 6j). Genome-wide qPCR profiling of 572 miRNAs in exosomes from human sera revealed 119 significantly different between control and HIV lipodystrophy subjects and 213 significantly different between control and CGL (FIGS. 1e-f; Tables 2 and 3).

TABLE 2

Serum Exosomal miRNAs in Humans with HIV Lipodystrophy

| miRNA | HIVvsCon p-value | HIVvsCon logFC | HIVvsCon FC | HIVvsCon FDR |
|---|---|---|---|---|
| hsa-miR-374b | 0.003 | 6.458 | 87.882 | 0.099 |
| hsa-miR-101 | 0.003 | 6.385 | 83.575 | 0.099 |
| hsa-miR-557 | 0.008 | 5.305 | 39.533 | 0.106 |
| hsa-miR-126 | 0.027 | 5.028 | 32.616 | 0.163 |
| hsa-miR-338-3p | 0.026 | 4.640 | 24.933 | 0.161 |
| hsa-miR-362-3p | 0.036 | 4.128 | 17.478 | 0.197 |
| hsa-miR-103 | 0.039 | 3.743 | 13.385 | 0.204 |
| hsa-miR-19a | 0.008 | 3.735 | 13.315 | 0.106 |
| hsa-miR-16 | 0.012 | 3.255 | 9.547 | 0.124 |
| hsa-miR-195 | 0.013 | 3.245 | 9.481 | 0.127 |
| hsa-miR-21 | 0.015 | 3.230 | 9.383 | 0.132 |
| hsa-miR-371-3p | 0.035 | 3.165 | 8.969 | 0.194 |
| hsa-miR-19b | 0.009 | 3.055 | 8.311 | 0.106 |
| hsa-miR-30a | 0.038 | 2.235 | 4.708 | 0.204 |
| hsa-miR-15a | 0.032 | 2.113 | 4.324 | 0.181 |
| hsa-miR-193a-5p | 0.024 | 1.858 | 3.624 | 0.160 |
| hsa-miR-483-3p | 0.031 | −1.830 | −3.555 | 0.178 |
| hsa-miR-631 | 0.044 | −1.843 | −3.586 | 0.225 |
| hsa-miR-147 | 0.024 | −1.905 | −3.745 | 0.160 |
| hsa-miR-323-3p | 0.016 | −1.948 | −3.857 | 0.140 |
| hsa-miR-483-5p | 0.022 | −2.010 | −4.028 | 0.160 |
| hsa-miR-149 | 0.024 | −2.128 | −4.370 | 0.160 |
| hsa-miR-487b | 0.045 | −2.183 | −4.539 | 0.231 |
| hsa-miR-10b | 0.018 | −2.208 | −4.619 | 0.146 |
| hsa-miR-646 | 0.017 | −2.298 | −4.916 | 0.144 |
| hsa-miR-671-5p | 0.025 | −2.405 | −5.296 | 0.160 |
| hsa-miR-802 | 0.049 | −2.455 | −5.483 | 0.237 |
| hsa-miR-485-3p | 0.009 | −2.468 | −5.531 | 0.106 |
| hsa-miR-610 | 0.011 | −2.513 | −5.706 | 0.121 |
| hsa-miR-583 | 0.020 | −2.585 | −6.000 | 0.155 |
| hsa-miR-141 | 0.024 | −2.608 | −6.094 | 0.160 |
| hsa-miR-767-5p | 0.038 | −2.623 | −6.158 | 0.204 |
| hsa-miR-222 | 0.008 | −2.650 | −6.277 | 0.106 |
| hsa-miR-770-5p | 0.004 | −2.683 | −6.420 | 0.099 |
| hsa-miR-181b | 0.018 | −2.693 | −6.464 | 0.145 |
| hsa-miR-511 | 0.048 | −2.703 | −6.509 | 0.236 |
| hsa-miR-648 | 0.024 | −2.728 | −6.623 | 0.160 |
| hsa-miR-519e | 0.023 | −2.740 | −6.681 | 0.160 |
| hsa-miR-500 | 0.025 | −2.773 | −6.833 | 0.160 |
| hsa-miR-509-3-5p | 0.015 | −2.918 | −7.555 | 0.136 |
| hsa-miR-615-3p | 0.037 | −2.960 | −7.781 | 0.204 |
| hsa-miR-935 | 0.028 | −2.978 | −7.876 | 0.166 |
| hsa-miR-516a-3p | 0.039 | −2.980 | −7.890 | 0.204 |
| hsa-miR-422a | 0.046 | −3.048 | −8.268 | 0.232 |
| hsa-miR-299-5p | 0.006 | −3.063 | −8.354 | 0.106 |
| hsa-miR-130b | 0.014 | −3.088 | −8.500 | 0.129 |
| hsa-miR-885-3p | 0.020 | −3.210 | −9.254 | 0.151 |
| hsa-miR-920 | 0.012 | −3.243 | −9.464 | 0.124 |
| hsa-miR-544 | 0.039 | −3.273 | −9.663 | 0.204 |
| hsa-miR-409-5p | 0.003 | −3.275 | −9.680 | 0.099 |
| hsa-miR-630 | 0.006 | −3.280 | −9.714 | 0.106 |
| hsa-miR-767-3p | 0.002 | −3.340 | −10.126 | 0.081 |
| hsa-miR-302e | 0.006 | −3.423 | −10.722 | 0.106 |
| hsa-miR-516b | 0.000 | −3.425 | −10.741 | 0.050 |
| hsa-miR-448 | 0.008 | −3.448 | −10.909 | 0.106 |
| hsa-miR-106b | 0.001 | −3.465 | −11.043 | 0.081 |
| hsa-miR-486-3p | 0.010 | −3.520 | −11.472 | 0.120 |
| hsa-miR-520d-5p | 0.048 | −3.535 | −11.592 | 0.236 |
| hsa-miR-490-3p | 0.025 | −3.545 | −11.672 | 0.161 |
| hsa-miR-487a | 0.007 | −3.550 | −11.713 | 0.106 |

TABLE 2-continued

Serum Exosomal miRNAs in Humans with HIV Lipodystrophy

| miRNA | HIVvsCon p-value | HIVvsCon logFC | HIVvsCon FC | HIVvsCon FDR |
|---|---|---|---|---|
| hsa-miR-183 | 0.049 | −3.625 | −12.338 | 0.238 |
| hsa-miR-323-5p | 0.047 | −3.735 | −13.315 | 0.235 |
| hsa-miR-374a | 0.022 | −3.743 | −13.385 | 0.160 |
| hsa-miR-875-3p | 0.025 | −3.743 | −13.385 | 0.160 |
| hsa-miR-518d-3p | 0.019 | −3.788 | −13.809 | 0.151 |
| hsa-miR-449b | 0.009 | −3.805 | −13.977 | 0.108 |
| hsa-miR-516a-5p | 0.008 | −3.815 | −14.074 | 0.106 |
| hsa-miR-140-5p | 0.007 | −3.845 | −14.370 | 0.106 |
| hsa-miR-449a | 0.014 | −3.848 | −14.395 | 0.129 |
| hsa-miR-635 | 0.017 | −3.863 | −14.545 | 0.144 |
| hsa-miR-654-3p | 0.028 | −3.913 | −15.058 | 0.166 |
| hsa-miR-410 | 0.003 | −3.990 | −15.889 | 0.099 |
| hsa-miR-501-3p | 0.010 | −3.990 | −15.889 | 0.114 |
| hsa-miR-508-5p | 0.019 | −4.020 | −16.223 | 0.151 |
| hsa-miR-657 | 0.014 | −4.113 | −17.298 | 0.129 |
| hsa-miR-520c-3p | 0.013 | −4.193 | −18.284 | 0.127 |
| hsa-miR-133b | 0.049 | −4.208 | −18.475 | 0.237 |
| hsa-miR-889 | 0.021 | −4.235 | −18.831 | 0.158 |
| hsa-miR-541 | 0.005 | −4.270 | −19.293 | 0.106 |
| hsa-miR-566 | 0.017 | −4.270 | −19.293 | 0.144 |
| hsa-miR-342-3p | 0.006 | −4.280 | −19.427 | 0.106 |
| hsa-miR-545 | 0.007 | −4.340 | −20.252 | 0.106 |
| hsa-miR-554 | 0.008 | −4.378 | −20.785 | 0.106 |
| hsa-miR-100 | 0.004 | −4.395 | −21.039 | 0.104 |
| hsa-miR-370 | 0.023 | −4.405 | −21.185 | 0.160 |
| hsa-miR-542-3p | 0.014 | −4.415 | −21.333 | 0.129 |
| hsa-miR-220c | 0.006 | −4.485 | −22.393 | 0.106 |
| hsa-miR-520c-5p | 0.029 | −4.545 | −23.344 | 0.169 |
| hsa-miR-890 | 0.026 | −4.570 | −23.752 | 0.161 |
| hsa-miR-645 | 0.006 | −4.583 | −23.959 | 0.106 |
| hsa-miR-603 | 0.018 | −4.638 | −24.890 | 0.147 |
| hsa-miR-220a | 0.031 | −4.683 | −25.679 | 0.178 |
| hsa-miR-520e | 0.008 | −4.713 | −26.218 | 0.106 |
| hsa-miR-369-5p | 0.005 | −4.733 | −26.584 | 0.106 |
| hsa-miR-632 | 0.013 | −4.865 | −29.141 | 0.127 |
| hsa-miR-548a-5p | 0.004 | −4.950 | −30.910 | 0.101 |
| hsa-miR-421 | 0.008 | −4.970 | −31.341 | 0.106 |
| hsa-miR-539 | 0.013 | −5.028 | −32.616 | 0.127 |
| hsa-miR-339-3p | 0.008 | −5.475 | −44.477 | 0.106 |
| hsa-miR-525-3p | 0.002 | −5.543 | −46.608 | 0.081 |
| hsa-miR-592 | 0.024 | −5.550 | −46.851 | 0.160 |
| hsa-miR-9 | 0.002 | −5.693 | −51.715 | 0.081 |
| hsa-miR-452 | 0.000 | −5.698 | −51.894 | 0.041 |
| hsa-miR-365 | 0.001 | −5.773 | −54.663 | 0.080 |
| hsa-miR-326 | 0.039 | −5.815 | −56.298 | 0.204 |
| hsa-miR-383 | 0.008 | −5.835 | −57.083 | 0.106 |
| hsa-miR-649 | 0.027 | −6.000 | −64.000 | 0.164 |
| hsa-miR-29c | 0.012 | −6.040 | −65.799 | 0.124 |
| hsa-miR-769-5p | 0.027 | −6.418 | −85.479 | 0.163 |
| hsa-miR-375 | 0.000 | −6.590 | −96.336 | 0.059 |
| hsa-miR-34c-5p | 0.001 | −6.693 | −103.429 | 0.081 |
| hsa-miR-346 | 0.004 | −7.050 | −132.514 | 0.099 |
| hsa-miR-199b-5p | 0.002 | −7.110 | −138.141 | 0.081 |
| hsa-miR-382 | 0.003 | −7.138 | −140.800 | 0.099 |
| hsa-miR-362-5p | 0.002 | −7.975 | −251.602 | 0.081 |
| hsa-miR-335 | 0.001 | −8.105 | −275.327 | 0.081 |
| hsa-miR-224 | 0.004 | −8.718 | −420.949 | 0.101 |
| hsa-miR-548e | 0.000 | −9.018 | −518.248 | 0.004 |
| hsa-miR-324-5p | 0.002 | −9.638 | −796.483 | 0.081 |

FDR = false discovery rate the repression.

TABLE 3

Serum Exosomal miRNAs in Humans with Congenital Generalized Lipodystrophy

| miRNA | CGLvsCon p-value | CGLvsCon logFC | CGLvsCon FC | CGLvsCon FDR |
|---|---|---|---|---|
| hsa-miR-190 | 0.037 | 10.825 | 1814.052 | 0.110 |
| hsa-miR-101 | 0.002 | 6.760 | 108.383 | 0.027 |
| hsa-miR-550 | 0.021 | 6.365 | 82.424 | 0.079 |
| hsa-miR-126 | 0.010 | 6.085 | 67.884 | 0.055 |
| hsa-miR-374b | 0.007 | 5.563 | 47.258 | 0.047 |
| hsa-miR-331-3p | 0.028 | 5.455 | 43.865 | 0.092 |
| hsa-miR-17 | 0.016 | 4.675 | 25.546 | 0.067 |
| hsa-miR-19b | 0.001 | 4.543 | 23.304 | 0.017 |
| hsa-miR-19a | 0.003 | 4.500 | 22.627 | 0.027 |
| hsa-miR-337-5p | 0.005 | 4.323 | 20.008 | 0.040 |
| hsa-miR-557 | 0.026 | 4.228 | 18.733 | 0.089 |
| hsa-miR-548i | 0.034 | 3.928 | 15.216 | 0.106 |
| hsa-miR-21 | 0.005 | 3.833 | 14.246 | 0.040 |
| hsa-miR-20a | 0.027 | 3.703 | 13.019 | 0.090 |
| hsa-miR-16 | 0.013 | 3.175 | 9.032 | 0.064 |
| hsa-miR-195 | 0.016 | 3.123 | 8.709 | 0.067 |
| hsa-miR-367 | 0.014 | 2.735 | 6.658 | 0.065 |
| hsa-miR-106a | 0.010 | 2.613 | 6.116 | 0.055 |
| hsa-miR-140-3p | 0.005 | 2.598 | 6.052 | 0.040 |
| hsa-miR-30a | 0.021 | 2.543 | 5.826 | 0.079 |
| hsa-miR-193a-5p | 0.011 | 2.173 | 4.508 | 0.055 |
| hsa-miR-30d | 0.035 | 1.903 | 3.739 | 0.106 |
| hsa-miR-450b-5p | 0.049 | 1.813 | 3.513 | 0.132 |
| hsa-miR-192 | 0.044 | 1.685 | 3.215 | 0.122 |
| hsa-miR-651 | 0.039 | −1.733 | −3.323 | 0.114 |
| hsa-miR-638 | 0.020 | −1.778 | −3.428 | 0.078 |
| hsa-miR-720 | 0.020 | −1.840 | −3.580 | 0.077 |
| hsa-let-7d | 0.027 | −1.898 | −3.726 | 0.090 |
| hsa-miR-614 | 0.032 | −1.925 | −3.797 | 0.102 |
| hsa-miR-640 | 0.029 | −1.945 | −3.850 | 0.095 |
| hsa-miR-135b | 0.035 | −1.993 | −3.979 | 0.106 |
| hsa-miR-377 | 0.025 | −2.128 | −4.370 | 0.088 |
| hsa-miR-665 | 0.014 | −2.133 | −4.385 | 0.065 |
| hsa-miR-937 | 0.017 | −2.158 | −4.461 | 0.068 |
| hsa-miR-877 | 0.017 | −2.173 | −4.508 | 0.070 |
| hsa-miR-212 | 0.008 | −2.233 | −4.699 | 0.050 |
| hsa-miR-188-3p | 0.014 | −2.270 | −4.823 | 0.065 |
| hsa-miR-668 | 0.020 | −2.298 | −4.916 | 0.077 |
| hsa-miR-933 | 0.015 | −2.300 | −4.925 | 0.067 |
| hsa-miR-221 | 0.014 | −2.320 | −4.993 | 0.064 |
| hsa-miR-483-3p | 0.009 | −2.350 | −5.098 | 0.050 |
| hsa-miR-10b | 0.013 | −2.353 | −5.107 | 0.064 |
| hsa-miR-188-5p | 0.017 | −2.358 | −5.125 | 0.070 |
| hsa-miR-610 | 0.014 | −2.390 | −5.242 | 0.065 |
| hsa-miR-874 | 0.005 | −2.423 | −5.361 | 0.039 |
| hsa-miR-671-3p | 0.003 | −2.425 | −5.370 | 0.027 |
| hsa-miR-92b | 0.003 | −2.460 | −5.502 | 0.033 |
| hsa-miR-125a-3p | 0.005 | −2.475 | −5.560 | 0.040 |
| hsa-miR-548u | 0.016 | −2.493 | −5.628 | 0.068 |
| hsa-miR-147 | 0.005 | −2.495 | −5.637 | 0.040 |
| hsa-miR-493 | 0.008 | −2.518 | −5.726 | 0.050 |
| hsa-miR-564 | 0.013 | −2.518 | −5.726 | 0.064 |
| hsa-miR-513a-5p | 0.050 | −2.535 | −5.796 | 0.133 |
| hsa-miR-300 | 0.010 | −2.553 | −5.866 | 0.055 |
| hsa-miR-507 | 0.025 | −2.593 | −6.031 | 0.087 |
| hsa-miR-766 | 0.004 | −2.613 | −6.116 | 0.036 |
| hsa-miR-323-3p | 0.003 | −2.625 | −6.169 | 0.027 |
| hsa-miR-153 | 0.015 | −2.670 | −6.364 | 0.067 |
| hsa-miR-514b-5p | 0.039 | −2.685 | −6.431 | 0.114 |
| hsa-miR-659 | 0.006 | −2.693 | −6.464 | 0.041 |
| hsa-miR-596 | 0.002 | −2.743 | −6.692 | 0.024 |
| hsa-miR-141 | 0.019 | −2.755 | −6.751 | 0.074 |
| hsa-miR-339-5p | 0.010 | −2.760 | −6.774 | 0.055 |

TABLE 3-continued

Serum Exosomal miRNAs in Humans with Congenital Generalized Lipodystrophy

| miRNA | CGLvsCon p-value | CGLvsCon logFC | CGLvsCon FC | CGLvsCon FDR |
|---|---|---|---|---|
| hsa-miR-149 | 0.006 | −2.765 | −6.797 | 0.041 |
| hsa-miR-485-3p | 0.004 | −2.785 | −6.892 | 0.036 |
| hsa-miR-802 | 0.028 | −2.795 | −6.940 | 0.092 |
| hsa-miR-605 | 0.001 | −2.823 | −7.074 | 0.020 |
| hsa-miR-631 | 0.005 | −2.823 | −7.074 | 0.040 |
| hsa-miR-30b | 0.014 | −2.865 | −7.285 | 0.065 |
| hsa-miR-199a-5p | 0.044 | −2.883 | −7.374 | 0.122 |
| hsa-miR-487a | 0.020 | −2.918 | −7.555 | 0.077 |
| hsa-miR-623 | 0.021 | −2.923 | −7.582 | 0.078 |
| hsa-miR-935 | 0.027 | −3.000 | −8.000 | 0.090 |
| hsa-miR-575 | 0.045 | −3.070 | −8.398 | 0.124 |
| hsa-miR-519e | 0.013 | −3.080 | −8.456 | 0.064 |
| hsa-miR-512-3p | 0.002 | −3.103 | −8.589 | 0.025 |
| hsa-miR-647 | 0.012 | −3.103 | −8.589 | 0.062 |
| hsa-miR-378 | 0.022 | −3.120 | −8.694 | 0.081 |
| hsa-miR-873 | 0.043 | −3.123 | −8.709 | 0.121 |
| hsa-miR-147b | 0.034 | −3.137 | −8.800 | 0.105 |
| hsa-miR-181b | 0.007 | −3.163 | −8.954 | 0.046 |
| hsa-miR-518d-5p | 0.046 | −3.175 | −9.032 | 0.125 |
| hsa-miR-646 | 0.002 | −3.178 | −9.047 | 0.027 |
| hsa-miR-518a-3p | 0.036 | −3.223 | −9.334 | 0.106 |
| hsa-miR-936 | 0.016 | −3.230 | −9.383 | 0.067 |
| hsa-miR-548a-3p | 0.019 | −3.245 | −9.481 | 0.076 |
| hsa-miR-490-3p | 0.037 | −3.255 | −9.547 | 0.109 |
| hsa-miR-583 | 0.005 | −3.268 | −9.630 | 0.040 |
| hsa-miR-518d-3p | 0.037 | −3.293 | −9.798 | 0.109 |
| hsa-miR-551b | 0.035 | −3.318 | −9.969 | 0.106 |
| hsa-miR-600 | 0.032 | −3.323 | −10.004 | 0.100 |
| hsa-miR-296-3p | 0.002 | −3.360 | −10.267 | 0.025 |
| hsa-miR-650 | 0.033 | −3.370 | −10.339 | 0.103 |
| hsa-miR-216b | 0.049 | −3.380 | −10.411 | 0.132 |
| hsa-miR-196b | 0.040 | −3.383 | −10.429 | 0.116 |
| hsa-miR-106b | 0.001 | −3.405 | −10.593 | 0.020 |
| hsa-miR-211 | 0.022 | −3.423 | −10.722 | 0.080 |
| hsa-miR-502-5p | 0.007 | −3.493 | −11.255 | 0.044 |
| hsa-miR-222 | 0.001 | −3.503 | −11.333 | 0.021 |
| hsa-miR-206 | 0.022 | −3.543 | −11.652 | 0.081 |
| hsa-miR-497 | 0.016 | −3.545 | −11.672 | 0.067 |
| hsa-miR-298 | 0.002 | −3.555 | −11.753 | 0.027 |
| hsa-miR-887 | 0.008 | −3.583 | −11.980 | 0.050 |
| hsa-miR-219-2-3p | 0.008 | −3.598 | −12.105 | 0.050 |
| hsa-miR-520e | 0.031 | −3.600 | −12.126 | 0.098 |
| hsa-miR-210 | 0.004 | −3.610 | −12.210 | 0.036 |
| hsa-miR-520c-3p | 0.026 | −3.630 | −12.381 | 0.089 |
| hsa-miR-587 | 0.045 | −3.633 | −12.402 | 0.124 |
| hsa-miR-143 | 0.037 | −3.635 | −12.424 | 0.109 |
| hsa-miR-490-5p | 0.021 | −3.688 | −12.884 | 0.079 |
| hsa-miR-202 | 0.008 | −3.690 | −12.906 | 0.050 |
| hsa-miR-875-3p | 0.026 | −3.695 | −12.951 | 0.090 |
| hsa-miR-609 | 0.045 | −3.715 | −13.132 | 0.124 |
| hsa-miR-654-5p | 0.014 | −3.733 | −13.292 | 0.065 |
| hsa-miR-339-3p | 0.049 | −3.778 | −13.713 | 0.132 |
| hsa-miR-934 | 0.026 | −3.843 | −14.345 | 0.088 |
| hsa-miR-508-5p | 0.024 | −3.845 | −14.370 | 0.086 |
| hsa-miR-509-5p | 0.007 | −3.865 | −14.571 | 0.044 |
| hsa-miR-617 | 0.016 | −3.888 | −14.800 | 0.068 |
| hsa-miR-921 | 0.024 | −3.930 | −15.242 | 0.086 |
| hsa-miR-658 | 0.001 | −3.933 | −15.269 | 0.017 |
| hsa-miR-299-5p | 0.001 | −3.938 | −15.322 | 0.020 |
| hsa-miR-566 | 0.025 | −3.943 | −15.375 | 0.088 |
| hsa-miR-220b | 0.019 | −3.980 | −15.780 | 0.074 |
| hsa-miR-453 | 0.024 | −3.990 | −15.889 | 0.086 |
| hsa-miR-491-3p | 0.006 | −3.995 | −15.945 | 0.041 |
| hsa-miR-501-5p | 0.000 | −4.008 | −16.083 | 0.011 |
| hsa-miR-603 | 0.035 | −4.025 | −16.280 | 0.106 |
| hsa-miR-634 | 0.039 | −4.038 | −16.421 | 0.113 |
| hsa-miR-744 | 0.004 | −4.053 | −16.593 | 0.034 |
| hsa-miR-34c-3p | 0.011 | −4.053 | −16.593 | 0.055 |
| hsa-miR-516b | 0.000 | −4.135 | −17.569 | 0.006 |
| hsa-miR-448 | 0.002 | −4.143 | −17.661 | 0.027 |
| hsa-miR-196a | 0.041 | −4.158 | −17.846 | 0.117 |
| hsa-miR-758 | 0.024 | −4.188 | −18.221 | 0.085 |
| hsa-miR-496 | 0.015 | −4.193 | −18.284 | 0.067 |
| hsa-miR-593 | 0.020 | −4.203 | −18.411 | 0.078 |
| hsa-miR-876-5p | 0.023 | −4.203 | −18.411 | 0.082 |
| hsa-miR-770-5p | 0.000 | −4.233 | −18.798 | 0.007 |
| hsa-miR-449b | 0.005 | −4.235 | −18.831 | 0.040 |
| hsa-miR-34b | 0.012 | −4.265 | −19.226 | 0.060 |
| hsa-miR-516a-3p | 0.006 | −4.295 | −19.630 | 0.041 |
| hsa-miR-554 | 0.008 | −4.325 | −20.043 | 0.050 |
| hsa-miR-544 | 0.010 | −4.328 | −20.077 | 0.055 |
| hsa-miR-612 | 0.028 | −4.338 | −20.217 | 0.092 |
| hsa-miR-519c-5p | 0.005 | −4.403 | −21.149 | 0.040 |
| hsa-miR-28-5p | 0.044 | −4.413 | −21.296 | 0.124 |
| hsa-miR-133a | 0.027 | −4.475 | −22.239 | 0.090 |
| hsa-miR-433 | 0.002 | −4.513 | −22.824 | 0.027 |
| hsa-miR-520b | 0.015 | −4.553 | −23.466 | 0.067 |
| hsa-miR-636 | 0.035 | −4.558 | −23.547 | 0.106 |
| hsa-miR-505 | 0.005 | −4.573 | −23.794 | 0.040 |
| hsa-miR-760 | 0.002 | −4.593 | −24.126 | 0.024 |
| hsa-miR-376a | 0.032 | −4.603 | −24.294 | 0.100 |
| hsa-miR-576-5p | 0.030 | −4.658 | −25.238 | 0.096 |
| hsa-miR-509-3-5p | 0.001 | −4.665 | −25.369 | 0.018 |
| hsa-miR-412 | 0.001 | −4.665 | −25.369 | 0.020 |
| hsa-miR-765 | 0.004 | −4.680 | −25.634 | 0.038 |
| hsa-miR-657 | 0.007 | −4.683 | −25.679 | 0.044 |
| hsa-miR-767-3p | 0.000 | −4.718 | −26.309 | 0.007 |
| hsa-miR-511 | 0.002 | −4.730 | −26.538 | 0.027 |
| hsa-miR-648 | 0.001 | −4.813 | −28.100 | 0.018 |
| hsa-miR-409-3p | 0.007 | −4.828 | −28.394 | 0.044 |
| hsa-miR-449a | 0.003 | −4.838 | −28.591 | 0.033 |
| hsa-miR-539 | 0.015 | −4.853 | −28.890 | 0.067 |
| hsa-miR-526a | 0.007 | −4.858 | −28.990 | 0.045 |
| hsa-miR-31 | 0.010 | −4.895 | −29.754 | 0.055 |
| hsa-miR-645 | 0.004 | −4.923 | −30.326 | 0.034 |
| hsa-miR-409-5p | 0.000 | −4.925 | −30.379 | 0.007 |
| hsa-miR-891b | 0.041 | −4.978 | −31.505 | 0.117 |
| hsa-miR-500b | 0.008 | −4.983 | −31.614 | 0.050 |
| hsa-miR-302e | 0.000 | −4.993 | −31.834 | 0.014 |
| hsa-miR-891a | 0.000 | −4.995 | −31.889 | 0.011 |
| hsa-miR-500 | 0.001 | −5.000 | −32.000 | 0.017 |
| hsa-miR-632 | 0.011 | −5.020 | −32.447 | 0.055 |
| hsa-miR-487b | 0.000 | −5.025 | −32.559 | 0.011 |
| hsa-miR-369-5p | 0.003 | −5.073 | −33.649 | 0.033 |
| hsa-miR-582-3p | 0.003 | −5.223 | −37.336 | 0.028 |

TABLE 3-continued

Serum Exosomal miRNAs in Humans with Congenital Generalized Lipodystrophy

| miRNA | CGLvsCon p-value | CGLvsCon logFC | CGLvsCon FC | CGLvsCon FDR |
|---|---|---|---|---|
| hsa-miR-656 | 0.001 | −5.293 | −39.192 | 0.020 |
| hsa-miR-626 | 0.013 | −5.318 | −39.877 | 0.064 |
| hsa-miR-133b | 0.016 | −5.365 | −41.212 | 0.068 |
| hsa-miR-199b-5p | 0.009 | −5.410 | −42.518 | 0.052 |
| hsa-miR-920 | 0.000 | −5.540 | −46.527 | 0.011 |
| hsa-miR-890 | 0.009 | −5.590 | −48.168 | 0.052 |
| hsa-miR-220a | 0.013 | −5.608 | −48.756 | 0.064 |
| hsa-miR-370 | 0.005 | −5.720 | −52.710 | 0.040 |
| hsa-miR-888 | 0.010 | −5.723 | −52.801 | 0.054 |
| hsa-miR-622 | 0.002 | −5.785 | −55.139 | 0.027 |
| hsa-miR-128 | 0.017 | −5.833 | −56.985 | 0.070 |
| hsa-miR-525-3p | 0.001 | −5.883 | −58.994 | 0.020 |
| hsa-miR-545 | 0.001 | −5.913 | −60.234 | 0.020 |
| hsa-miR-542-3p | 0.002 | −5.923 | −60.653 | 0.027 |
| hsa-miR-29c | 0.011 | −6.060 | −66.718 | 0.058 |
| hsa-miR-548a-5p | 0.001 | −6.140 | −70.522 | 0.020 |
| hsa-miR-421 | 0.002 | −6.158 | −71.383 | 0.025 |
| hsa-miR-630 | 0.000 | −6.163 | −71.630 | 0.006 |
| hsa-miR-383 | 0.006 | −6.175 | −72.254 | 0.041 |
| hsa-miR-548c-5p | 0.001 | −6.420 | −85.627 | 0.017 |
| hsa-miR-34c-5p | 0.001 | −6.578 | −95.505 | 0.020 |
| hsa-miR-323-5p | 0.002 | −6.715 | −105.055 | 0.025 |
| hsa-miR-452 | 0.000 | −6.718 | −105.237 | 0.006 |
| hsa-miR-342-3p | 0.000 | −6.865 | −116.566 | 0.010 |
| hsa-miR-423-3p | 0.000 | −6.900 | −119.428 | 0.000 |
| hsa-miR-375 | 0.000 | −7.158 | −142.765 | 0.011 |
| hsa-miR-365 | 0.000 | −7.318 | −159.510 | 0.007 |
| hsa-miR-382 | 0.002 | −7.478 | −178.218 | 0.027 |
| hsa-miR-346 | 0.002 | −7.760 | −216.767 | 0.025 |
| hsa-miR-484 | 0.001 | −7.783 | −220.174 | 0.020 |
| hsa-miR-637 | 0.001 | −8.035 | −262.287 | 0.020 |
| hsa-miR-362-5p | 0.001 | −8.665 | −405.905 | 0.020 |
| hsa-miR-548e | 0.000 | −9.358 | −655.976 | 0.002 |
| hsa-miR-324-5p | 0.002 | −9.525 | −736.734 | 0.027 |
| hsa-miR-224 | 0.001 | −10.530 | −1478.583 | 0.020 |

FDR = false discovery rate

Figure 1A:
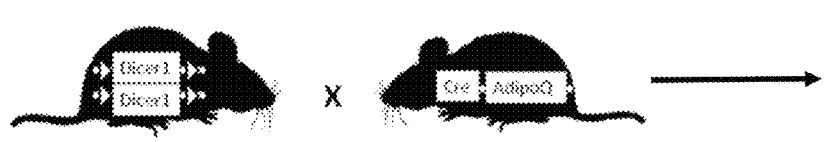
Figure 1B:
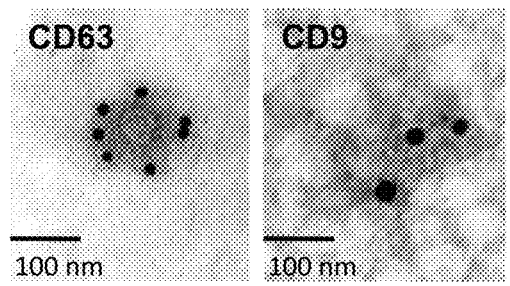
Figure 1C:
Figure 1D:
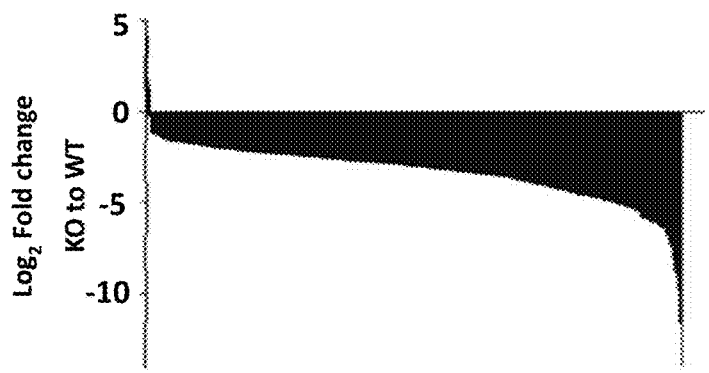
Figure 1E:
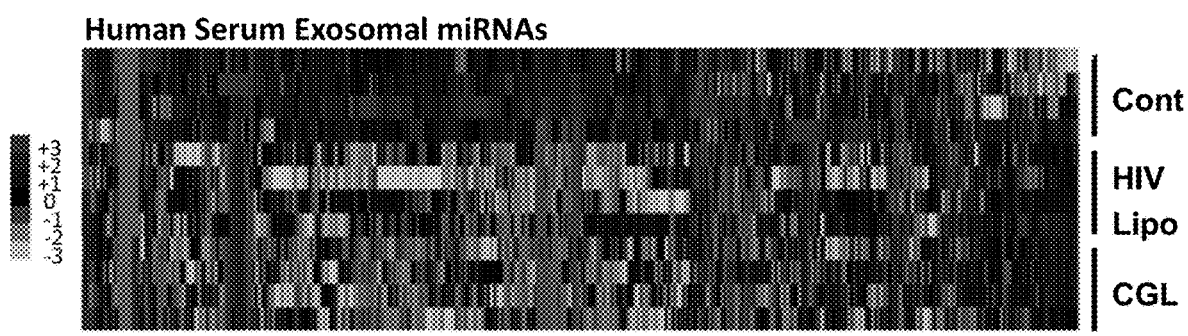
Figure 1F:
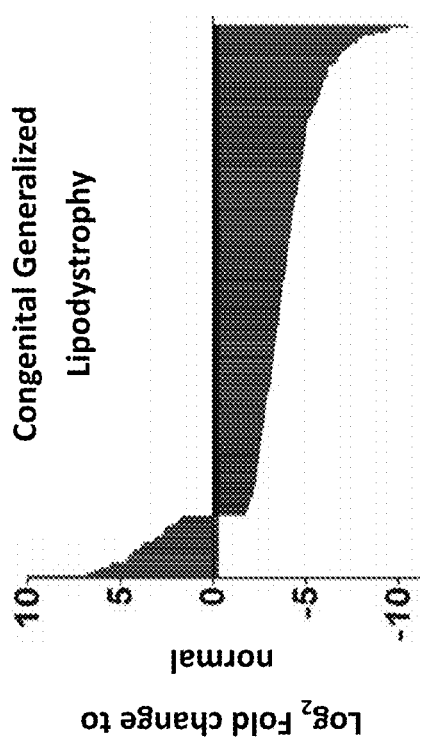
Figure 1F:
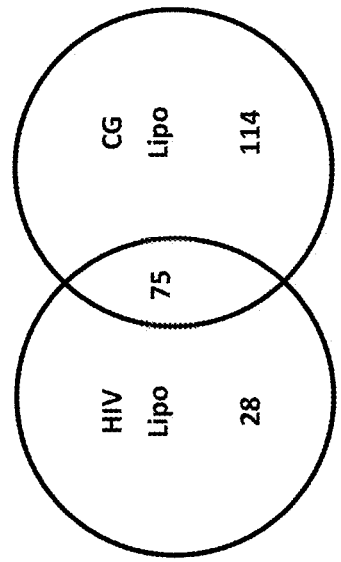
Figure 1G:
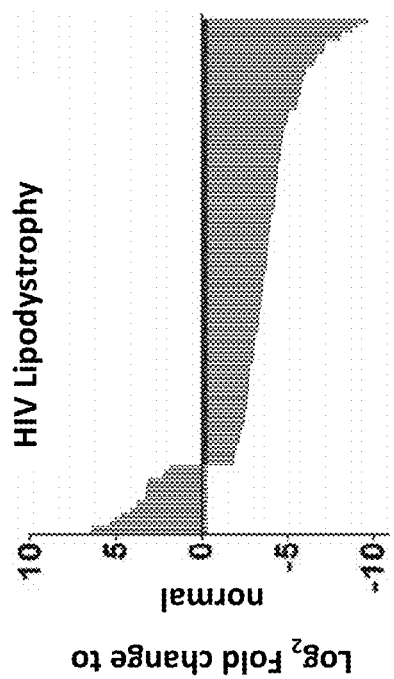
Figure 1G:
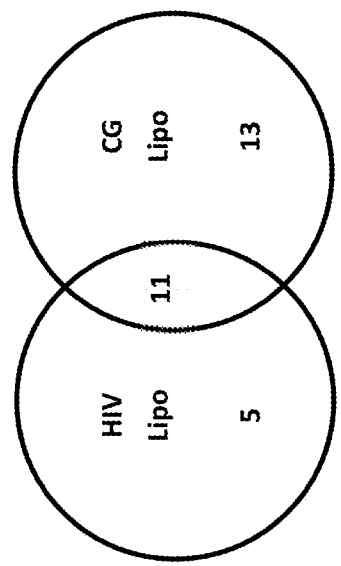

Of these, only 5% (29 miRNAs) were upregulated in either HIV or CGL patients, while 217 (38%) were robustly decreased in either CGL or HIV lipodystrophy, and 75 were decreased in both lipodystrophy groups (FIG. 1g, Table 4).

TABLE 4

Exosomal miRNAs Jointly Regulated in both Human HIV and Generalized Lipodystrophy

| upregulated in HIV | common upregulated | upregulated in CGL |
|---|---|---|
| hsa-miR-338-3p | hsa-miR-19b | hsa-miR-337-5p |
| hsa-miR-15a | hsa-miR-101 | hsa-miR-140-3p |
| hsa-miR-362-3p | hsa-miR-19a | hsa-miR-106a |
| hsa-miR-371-3p | hsa-miR-374b | hsa-miR-367 |
| hsa-miR-103 | hsa-miR-21 | hsa-miR-17 |
|  | hsa-miR-16 | hsa-miR-550 |
|  | hsa-miR-557 | hsa-miR-190 |
|  | hsa-miR-195 | hsa-miR-20a |
|  | hsa-miR-193a-5p | hsa-miR-331-3p |
|  | hsa-miR-126 | hsa-miR-30d |
|  | hsa-miR-30a | hsa-miR-548i |
|  |  | hsa-miR-192 |

TABLE 4-continued

Exosomal miRNAs Jointly Regulated in both Human HIV and Generalized Lipodystrophy

|  |  | hsa-miR-450b-5p |
|---|---|---|
| downregulated in HIV | common downregulated | downregulated CGL |
| hsa-miR-335 | hsa-miR-548e | hsa-miR-423-3p |
| hsa-miR-9 | hsa-miR-452 | hsa-miR-658 |
| hsa-miR-410 | hsa-miR-516b | hsa-miR-891a |
| hsa-miR-100 | hsa-miR-630 | hsa-miR-501-5p |
| hsa-miR-541 | hsa-miR-365 | hsa-miR-548c-5p |
| hsa-miR-220c | hsa-miR-767-3p | hsa-miR-605 |
| hsa-miR-140-5p | hsa-miR-375 | hsa-miR-596 |
| hsa-miR-516a-5p | hsa-miR-409-5p | hsa-miR-412 |
| hsa-miR-501-3p | hsa-miR-770-5p | hsa-miR-484 |
| hsa-miR-486-3p | hsa-miR-342-3p | hsa-miR-637 |
| hsa-miR-130b | hsa-miR-487b | hsa-miR-512-3p |
| hsa-miR-889 | hsa-miR-920 | hsa-miR-656 |
| hsa-miR-885-3p | hsa-miR-34c-5p | hsa-miR-760 |
| hsa-miR-635 | hsa-miR-302e | hsa-miR-296-3p |
| hsa-miR-374a | hsa-miR-362-5p | hsa-miR-298 |
| hsa-miR-671-5p | hsa-miR-106b | hsa-miR-671-3p |
| hsa-miR-769-5p | hsa-miR-525-3p | hsa-miR-433 |
| hsa-miR-483-5p | hsa-miR-548a-5p | hsa-miR-622 |
| hsa-miR-592 | hsa-miR-500 | hsa-miR-582-3p |
| hsa-miR-767-5p | hsa-miR-224 | hsa-miR-887 |
| hsa-miR-649 | hsa-miR-509-3-5p | hsa-miR-92b |
| hsa-miR-654-3p | hsa-miR-648 | hsa-miR-744 |
| hsa-miR-520c-5p | hsa-miR-545 | hsa-miR-519c-5p |
| hsa-miR-183 | hsa-miR-324-5p | hsa-miR-210 |
| hsa-miR-615-3p | hsa-miR-299-5p | hsa-miR-766 |
| hsa-miR-422a | hsa-miR-346 | hsa-miR-212 |
| hsa-miR-326 | hsa-miR-222 | hsa-miR-874 |
| hsa-miR-520d-5p | hsa-miR-382 | hsa-miR-765 |
|  | hsa-miR-199b-5p | hsa-miR-125a-3p |
|  | hsa-miR-421 | hsa-miR-505 |
|  | hsa-miR-448 | hsa-miR-220b |
|  | hsa-miR-369-5p | hsa-miR-491-3p |
|  | hsa-miR-542-3p | hsa-miR-409-3p |
|  | hsa-miR-645 | hsa-miR-659 |
|  | hsa-miR-323-5p | hsa-miR-514b-5p |
|  | hsa-miR-646 | hsa-miR-502-5p |
|  | hsa-miR-323-3p | hsa-miR-526a |
|  | hsa-miR-485-3p | hsa-miR-509-5p |
|  | hsa-miR-511 | hsa-miR-199a-5p |
|  | hsa-miR-449a | hsa-miR-500b |
|  | hsa-miR-449b | hsa-miR-219-2-3p |
|  | hsa-miR-383 | hsa-miR-202 |
|  | hsa-miR-554 | hsa-miR-493 |
|  | hsa-miR-657 | hsa-miR-888 |
|  | hsa-miR-583 | hsa-miR-153 |
|  | hsa-miR-370 | hsa-miR-300 |
|  | hsa-miR-147 | hsa-miR-31 |
|  | hsa-miR-149 | hsa-miR-221 |
|  | hsa-miR-631 | hsa-miR-339-5p |
|  | hsa-miR-487a | hsa-miR-34c-3p |
|  | hsa-miR-181b | hsa-miR-647 |
|  | hsa-miR-29c | hsa-miR-34b |
|  | hsa-miR-632 | hsa-miR-626 |
|  | hsa-miR-516a-3p | hsa-miR-933 |
|  | hsa-miR-610 | hsa-miR-188-3p |
|  | hsa-miR-520e | hsa-miR-564 |
|  | hsa-miR-539 | hsa-miR-520b |
|  | hsa-miR-890 | hsa-miR-453 |
|  | hsa-miR-483-3p | hsa-miR-30b |
|  | hsa-miR-10b | hsa-miR-720 |
|  | hsa-miR-339-3p | hsa-miR-654-5p |
|  | hsa-miR-519e | hsa-miR-877 |
|  | hsa-miR-544 | hsa-miR-548u |
|  | hsa-miR-520c-3p | hsa-miR-665 |
|  | hsa-miR-220a | hsa-miR-133a |
|  | hsa-miR-566 | hsa-miR-497 |
|  | hsa-miR-141 | hsa-miR-617 |
|  | hsa-miR-508-5p | hsa-miR-668 |
|  | hsa-miR-603 | hsa-miR-496 |
|  | hsa-miR-133b | hsa-miR-188-5p |
|  | hsa-miR-875-3p | hsa-miR-936 |
|  | hsa-miR-518d-3p | hsa-miR-128 |

TABLE 4-continued

Exosomal miRNAs Jointly Regulated in both Human HIV and Generalized Lipodystrophy

| | |
|---|---|
| hsa-miR-935 | hsa-miR-937 |
| hsa-miR-490-3p | hsa-miR-593 |
| hsa-miR-802 | hsa-miR-378 |
| | hsa-miR-377 |
| | hsa-miR-548a-3p |
| | hsa-miR-135b |
| | hsa-miR-638 |
| | hsa-miR-876-5p |
| | hsa-miR-211 |
| | hsa-miR-490-5p |
| | hsa-miR-623 |
| | hsa-miR-206 |
| | hsa-let-7d |
| | hsa-miR-758 |
| | hsa-miR-634 |
| | hsa-miR-921 |
| | hsa-miR-507 |
| | hsa-miR-376a |
| | hsa-miR-934 |
| | hsa-miR-551b |
| | hsa-miR-576-5p |
| | hsa-miR-612 |
| | hsa-miR-651 |
| | hsa-miR-147b |
| | hsa-miR-640 |
| | hsa-miR-873 |
| | hsa-miR-600 |
| | hsa-miR-614 |
| | hsa-miR-650 |
| | hsa-miR-28-5p |
| | hsa-miR-518a-3p |
| | hsa-miR-518d-5p |
| | hsa-miR-636 |
| | hsa-miR-196b |
| | hsa-miR-143 |
| | hsa-miR-196a |
| | hsa-miR-891b |
| | hsa-miR-513a-5p |
| | hsa-miR-609 |
| | hsa-miR-587 |
| | hsa-miR-575 |
| | hsa-miR-216b |

Again, several of these miRNAs (miR-221, miR-222 and miR-16) have been previously implicated in regulation of adipose tissue[9,10,20,21]. Thirty of the miRNAs that were decreased in serum of both patient cohorts were also decreased in the serum of the ADicerKO mice (Table 5).

TABLE 5

Serum Exosomal miRNAs Which Are Down-regulated in Both Human Lipodystrophies and ADicerKO Mice
Homolog common downregulated

| |
|---|
| miR-324-5p |
| miR-323-5p |
| miR-323-3p |
| miR-409-5p |
| miR-500 |
| miR-149 |
| miR-29c |
| miR-375 |
| miR-382 |
| miR-383 |
| miR-449b |
| miR-346 |
| miR-10b |
| miR-370 |
| miR-452 |
| miR-449a |
| miR-487b |
| miR-339-3p |
| miR-421 |

TABLE 5-continued

Serum Exosomal miRNAs Which Are Down-regulated in Both Human Lipodystrophies and ADicerKO Mice
Homolog common downregulated

| |
|---|
| miR-147 |
| miR-133b |
| miR-544 |
| miR-365 |
| miR-222 |
| miR-342-3p |
| miR-141 |
| miR-802 |
| miR-362-5p |
| miR-770-5p |
| miR-448 |

Lipodystrophy and altered metabolism in general might be an important driver of altered exosomal miRNA availability in serum. One way to dissociate altered metabolism from these phenotypes is to compare serum miRNAs from young control and AdicerKO mice at 4 weeks of age, since at this age the metabolic phenotypes of ADicerKO mice have not yet appeared. miRNA profiling of circulating exosomes from 4 week-old ADicerKO mice (FIG. 6g) demonstrated that of the of the 380 miRNAs profiled, 373 were detectable with 202 down-regulated in ADicerKO mice and only 23 miRNAs up-regulated, indicating that reduction in circulating miRNAs reflects primarily the difference in miRNA processing rather than the effect of chronic lipodystrophy.

These data indicate that adipose tissue is a major source of circulating exosomal miRNA and that exosomal miRNA downregulation is due to Dicer deficiency in fat and not due to onset of lipodystrophy.

Figure 2A:
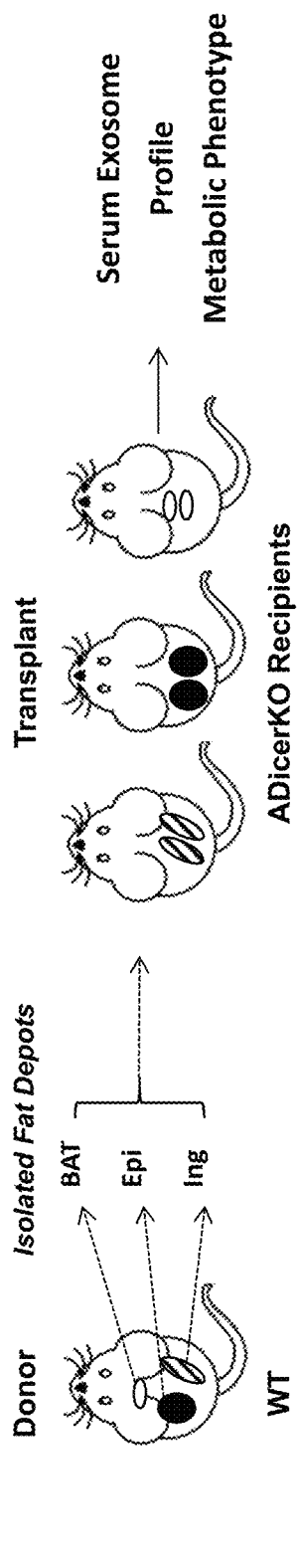
Figure 2B:
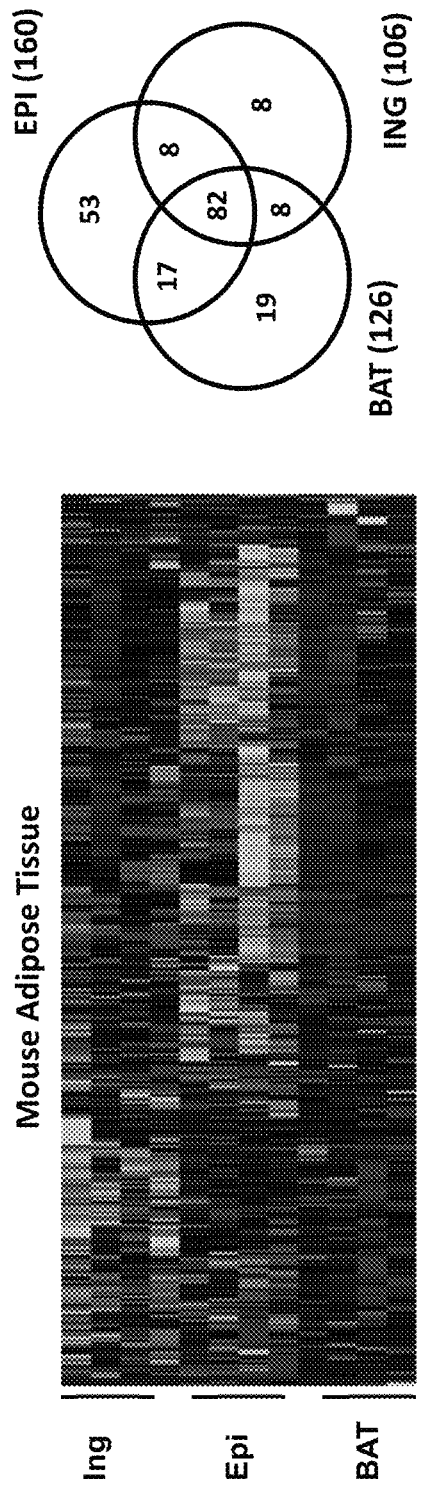

Example 2. Adipose Tissue Transplantation Reconstitutes Circulating miRNAs in Lipodystrophic Mice Next, fat tissue was transplanted from normal mice into ADicerKO mice and mice were followed for 14 days (FIG. 2a). miRNA profiling of subcutaneous inguinal (ing) white adipose tissue (WAT), intraabdominal epididymal (Epi) WAT, and interscapular BAT from the normal donor mice taken at the time of transplantation revealed distinct, depot-specific signatures consistent with previous studies[22] (FIG. 2b). Considering only the miRNAs that were higher expressed than the control U6, 126 were highly expressed in BAT, 106 in Ing-WAT, and 160 in Epi-WAT, with 82 of these miRNAs expressed in all three depots (FIGS. 2b, 7a; Table 6).

Figure 7A:
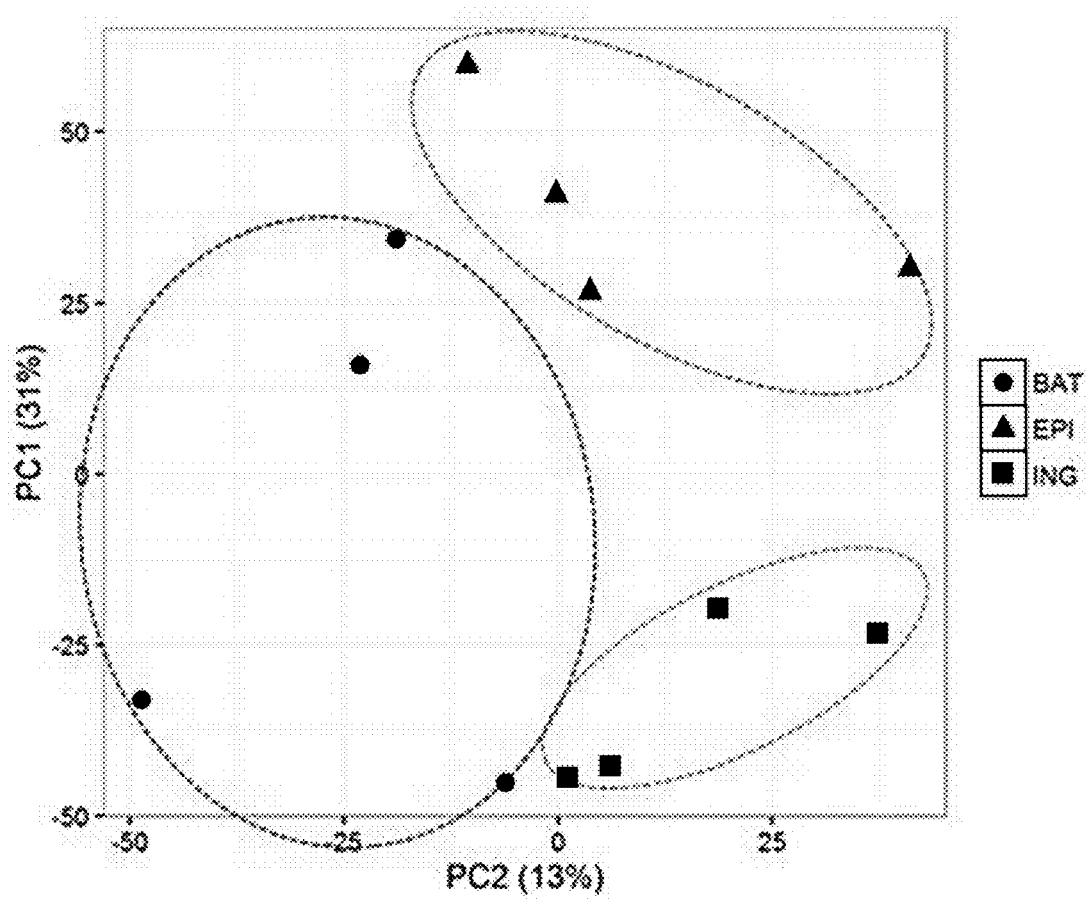
Figure 7B:
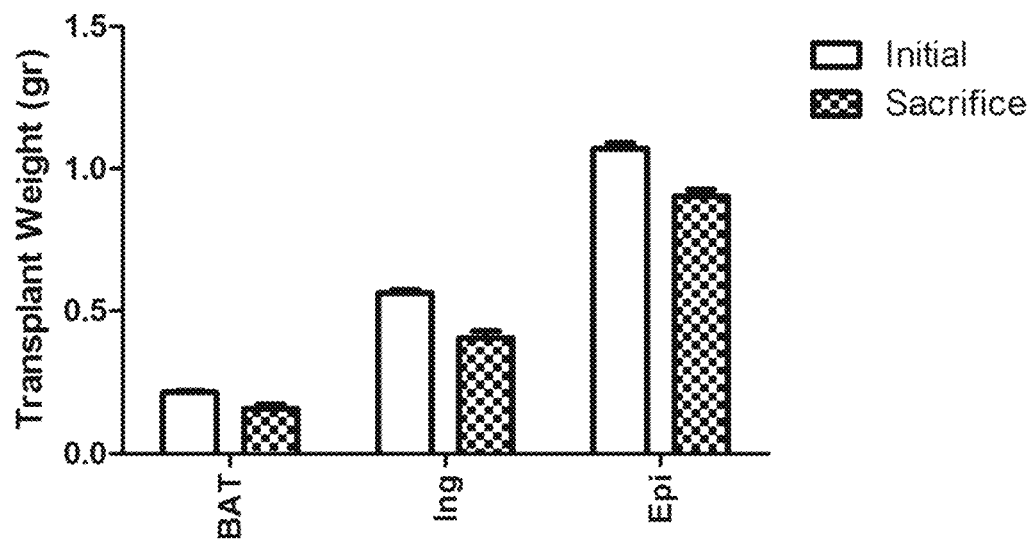
Figure 7C:
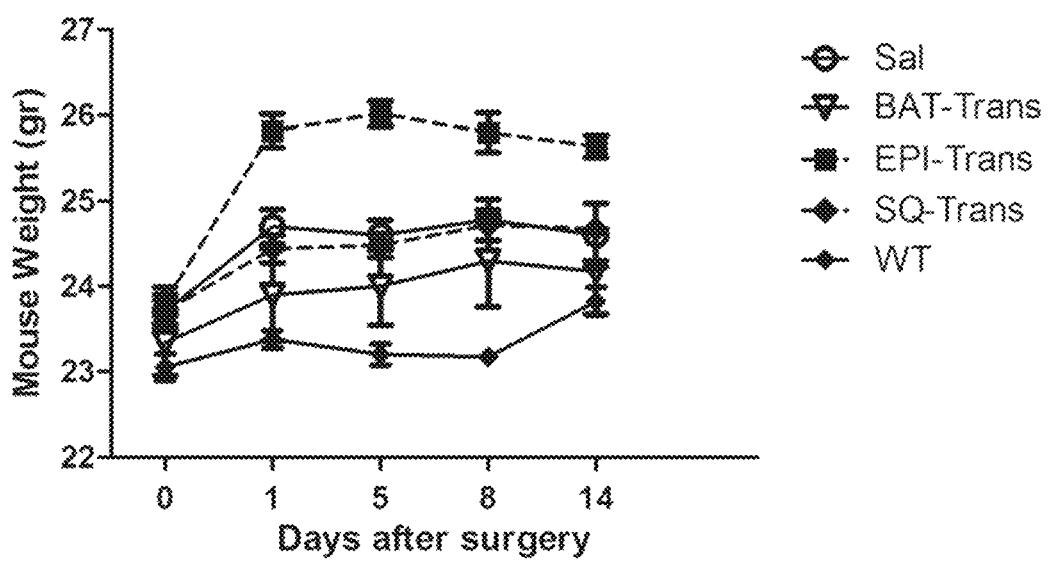
Figure 7D:
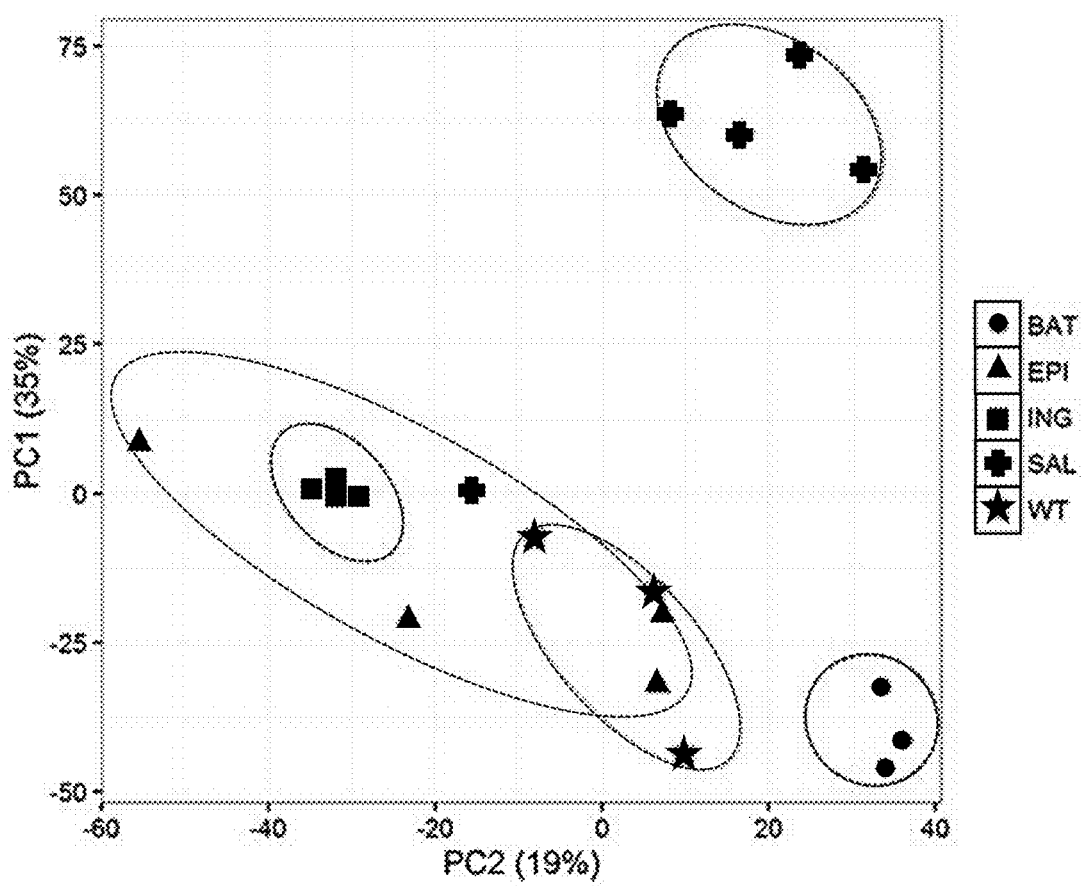

At the time of sacrifice two weeks later, all mice had maintained body weight, and the transplanted fat weighed 80-90% of the original weight, indicating successful engraftment (FIGS. 7b and 7c). "Sal" refers to ADicerKO mice that received saline instead of a transplant. "Wt" refers to wild-type mice, other groups in FIG. 7c are ADicerKO mice that have received fat tissue transplants.

Table 6 presents miRNA profiling of subcutaneous inguinal (ing) WAT, intraabdominal epididymal (Epi) WAT, and interscapular BAT from the normal donor mice taken at the time of transplantation revealed distinct, depot-specific signatures consistent with previous studies[22]. Considering only the miRNAs that were expressed greater than U6, 126 were highly expressed in BAT, 106 in Ing-WAT, and 160 in Epi-WAT, with 82 of these miRNAs expressed in all three depots when compared to ADicerKO Sal group.

TABLE 6

Fat tissue mouse miRNA signatures

| miRNA | EPIvsING p-value | EPIvsING FDR | EPIvsING logFC | EPIvsING FC |
|---|---|---|---|---|
| mmu-miR-290-5p | <0.0001 | 0.006 | −6.78 | −109.861 |
| mmu-miR-574-5p | <0.0001 | 0.02 | −9.332 | −644.501 |
| mmu-miR-500 | <0.0001 | 0.02 | 6.02 | 64.914 |
| mmu-miR-467h | <0.0001 | 0.02 | −3.582 | −11.976 |
| mmu-miR-666-5p | <0.0001 | 0.024 | −3.02 | −8.109 |
| mmu-miR-295* | <0.0001 | 0.056 | −2.628 | −6.18 |
| mmu-miR-883b-3p | 0.001 | 0.056 | 7.6 | 193.986 |
| mmu-miR-26b | 0.001 | 0.031 | −3.765 | −13.591 |
| mmu-miR-33 | 0.001 | 0.031 | −4.895 | −29.744 |
| mmu-miR-1949 | 0.001 | 0.056 | −2.413 | −5.325 |
| mmu-miR-452 | 0.001 | 0.039 | −3.135 | −8.782 |
| mmu-miR-200a* | 0.001 | 0.056 | 2.702 | 6.508 |
| mmu-miR-883a-5p | 0.001 | 0.056 | −6.818 | −112.805 |
| mmu-miR-345-3p | 0.001 | 0.039 | −3.29 | −9.778 |
| mmu-miR-1-2-as | 0.001 | 0.039 | 4.985 | 31.679 |
| mmu-miR-467a* | 0.001 | 0.056 | 1.695 | 3.237 |
| mmu-miR-1 | 0.001 | 0.039 | −14.052 | −16985.769 |
| mmu-miR-196a* | 0.001 | 0.056 | 6.927 | 121.71 |
| mmu-miR-467g | 0.001 | 0.039 | 11.43 | 2760.016 |
| mmu-miR-326 | 0.001 | 0.039 | −2.315 | −4.974 |
| mmu-miR-291a-5p | 0.001 | 0.039 | −5.885 | −59.078 |
| mmu-miR-1981 | 0.001 | 0.056 | −2.023 | −4.063 |
| mmu-miR-1190 | 0.002 | 0.056 | −6.028 | −65.24 |
| mmu-miR-568 | 0.002 | 0.041 | 7.97 | 250.812 |
| mmu-miR-804 | 0.002 | 0.056 | −9.055 | −531.966 |
| mmu-miR-340-5p | 0.002 | 0.041 | −5.91 | −60.11 |
| mmu-miR-465a-5p | 0.002 | 0.041 | −2.162 | −4.475 |
| mmu-miR-463* | 0.002 | 0.056 | −7.075 | −134.848 |
| mmu-miR-6690 | 0.002 | 0.056 | −1.665 | −3.172 |
| mmu-miR-467a | 0.002 | 0.041 | −3.562 | −11.811 |
| mmu-miR-127 | 0.002 | 0.041 | −3.06 | −8.337 |
| mmu-miR-30b | 0.002 | 0.041 | −2.51 | −5.694 |
| mmu-miR-136 | 0.002 | 0.041 | −7.387 | −167.386 |
| mmu-miR-877 | 0.002 | 0.058 | −2.428 | −5.38 |
| mmu-miR-343 | 0.002 | 0.042 | −3.66 | −12.637 |
| mmu-miR-299 | 0.003 | 0.044 | 6.535 | 92.762 |
| mmu-miR-31 | 0.003 | 0.044 | −2.872 | −7.321 |
| mmu-miR-106b* | 0.003 | 0.062 | 1.822 | 3.536 |
| mmu-miR-1971 | 0.003 | 0.062 | −2.385 | −5.224 |
| mmu-miR-450b-3p | 0.003 | 0.045 | 2.755 | 6.753 |
| mmu-miR-212 | 0.004 | 0.051 | −5.122 | −34.825 |
| mmu-miR-467f | 0.004 | 0.051 | −2.905 | −7.488 |
| mmu-miR-1188 | 0.004 | 0.077 | 2.947 | 7.713 |
| mmu-miR-328 | 0.004 | 0.052 | −1.707 | −3.265 |
| mmu-miR-1947 | 0.004 | 0.077 | −2.365 | −5.152 |
| mmu-miR-467b | 0.004 | 0.054 | −2.245 | −4.739 |
| mmu-miR-298 | 0.004 | 0.054 | −2.467 | −5.529 |
| mmu-miR-449c | 0.005 | 0.054 | −5.717 | −52.602 |
| mmu-miR-451 | 0.005 | 0.054 | −1.527 | −2.882 |
| mmu-miR-25 | 0.005 | 0.054 | −3.262 | −9.593 |
| mmu-miR-1951 | 0.005 | 0.081 | −2.345 | −5.081 |
| mmu-miR-148a* | 0.005 | 0.081 | −4.13 | −17.511 |
| mmu-miR-449a | 0.005 | 0.055 | −4.507 | −22.738 |
| mmu-let-7i* | 0.005 | 0.081 | 5.05 | 33.124 |
| mmu-miR-711 | 0.005 | 0.081 | 3.292 | 9.797 |
| mmu-miR-1933-3p | 0.005 | 0.081 | 2.665 | 6.341 |
| mmu-miR-409-3p | 0.005 | 0.059 | 2.758 | 6.764 |
| mmu-miR-125a-3p | 0.006 | 0.06 | −3.307 | −9.897 |
| mmu-miR-760 | 0.006 | 0.084 | 3.8 | 13.927 |
| mmu-miR-689 | 0.006 | 0.084 | 3.452 | 10.946 |
| mmu-miR-1936 | 0.007 | 0.088 | 5.347 | 40.71 |
| mmu-miR-27b | 0.007 | 0.07 | −1.692 | −3.231 |
| mmu-miR-707 | 0.007 | 0.091 | 3.56 | 11.793 |
| mmu-miR-222 | 0.007 | 0.07 | −3.17 | −8.998 |
| mmu-miR-877* | 0.007 | 0.092 | 1.812 | 3.512 |
| mmu-miR-323-5p | 0.008 | 0.07 | −3.89 | −14.821 |
| mmu-miR-1944 | 0.008 | 0.092 | −1.975 | −3.932 |
| mmu-miR-130b | 0.008 | 0.07 | 5.103 | 34.367 |
| mmu-miR-363 | 0.008 | 0.07 | −3.362 | −10.282 |
| mmu-miR-466a-5p | 0.008 | 0.07 | −4.78 | −27.465 |
| mmu-miR-380-3p | 0.008 | 0.07 | 8.748 | 429.931 |
| mmu-miR-125b-3p | 0.008 | 0.07 | −2.707 | −6.53 |
| mmu-miR-344 | 0.008 | 0.07 | 2.418 | 5.344 |
| mmu-miR-24 | 0.009 | 0.072 | −1.352 | −2.553 |
| mmu-miR-712 | 0.009 | 0.094 | −3.485 | −11.198 |

TABLE 6-continued

Fat tissue mouse miRNA signatures

| | | | | |
|---|---|---|---|---|
| mmu-miR-674 | 0.009 | 0.094 | 2.297 | 4.915 |
| mmu-miR-698 | 0.009 | 0.094 | 5.322 | 40.011 |
| mmu-miR-351 | 0.009 | 0.072 | −1.76 | −3.386 |
| mmu-miR-139-3p | 0.009 | 0.072 | 3.678 | 12.799 |
| mmu-miR-881* | 0.009 | 0.095 | 5.342 | 40.569 |
| mmu-miR-770-5p | 0.01 | 0.097 | −3.115 | −8.665 |
| mmu-miR-654-3p | 0.01 | 0.074 | −2.37 | −5.168 |
| mmu-miR-687 | 0.01 | 0.098 | 3.69 | 12.905 |
| mmu-miR-346 | 0.01 | 0.074 | −1.655 | −3.148 |
| mmu-miR-669e | 0.01 | 0.074 | 2.063 | 4.178 |
| mmu-miR-147 | 0.011 | 0.074 | −2.27 | −4.822 |
| mmu-miR-423-5p | 0.011 | 0.074 | −1.312 | −2.483 |
| mmu-miR-23b | 0.011 | 0.074 | −2.435 | −5.406 |
| mmu-miR-18a | 0.011 | 0.074 | −1.912 | −3.763 |
| mmu-miR-34b-3p | 0.011 | 0.074 | −2.822 | −7.072 |
| mmu-miR-324-5p | 0.011 | 0.074 | −3.062 | −8.352 |
| mmu-miR-214* | 0.011 | 0.105 | 2.737 | 6.668 |
| mmu-miR-33* | 0.012 | 0.105 | 1.472 | 2.775 |
| mmu-miR-138* | 0.012 | 0.105 | 2.217 | 4.65 |
| mmu-miR-1199 | 0.012 | 0.105 | 1.33 | 2.514 |
| mmu-miR-1941-5p | 0.013 | 0.11 | 2.66 | 6.319 |
| mmu-miR-138 | 0.013 | 0.084 | −3.107 | −8.616 |
| mmu-miR-668 | 0.013 | 0.084 | −3.072 | −8.41 |
| mmu-miR-369-3p | 0.013 | 0.084 | 6.418 | 85.506 |
| mmu-miR-367 | 0.013 | 0.084 | −4.897 | −29.796 |
| mmu-miR-148b | 0.014 | 0.084 | −1.325 | −2.505 |
| mmu-miR-465b-5p | 0.014 | 0.084 | −2.9 | −7.462 |
| mmu-miR-708 | 0.014 | 0.112 | −1.883 | −3.688 |
| mmu-miR-27a* | 0.014 | 0.112 | −1.415 | −2.667 |
| mmu-miR-200c* | 0.014 | 0.112 | 4.887 | 29.596 |
| mmu-miR-4661 | 0.015 | 0.085 | −5.29 | −39.112 |
| mmu-miR-207 | 0.015 | 0.085 | 2.853 | 7.225 |
| mmu-miR-181b | 0.015 | 0.085 | −2.512 | −5.704 |
| mmu-miR-1194 | 0.015 | 0.112 | −1.213 | −2.318 |
| mmu-miR-547 | 0.016 | 0.088 | −7.647 | −200.442 |
| mmu-miR-431 | 0.016 | 0.088 | 2.13 | 4.379 |
| mmu-miR-17 | 0.016 | 0.088 | −1.82 | −3.53 |
| mmu-miR-1934 | 0.016 | 0.122 | 2.037 | 4.105 |
| mmu-miR-669h-3p | 0.016 | 0.089 | −1.3 | −2.462 |
| mmu-miR-339-3p | 0.017 | 0.089 | 26.118 | 72826545.03 |
| mmu-miR-1897-3p | 0.017 | 0.123 | 2.362 | 5.142 |
| mmu-miR-509-3p | 0.017 | 0.089 | 3.058 | 8.328 |
| mmu-let-7e | 0.017 | 0.089 | −1.202 | −2.301 |
| mmu-let-7b* | 0.017 | 0.125 | −1.458 | −2.747 |
| mmu-miR-744* | 0.018 | 0.128 | 3.157 | 8.922 |
| mmu-miR-22 | 0.019 | 0.096 | −2.12 | −4.346 |
| mmu-miR-1904 | 0.019 | 0.128 | 1.082 | 2.117 |
| mmu-miR-183* | 0.019 | 0.129 | 3.945 | 15.399 |
| mmu-miR-142-5p | 0.02 | 0.101 | −3.957 | −15.531 |
| mmu-miR-34b-5p | 0.02 | 0.101 | 2.57 | 5.94 |
| mmu-miR-141* | 0.021 | 0.136 | 7.707 | 208.993 |
| mmu-miR-28 | 0.021 | 0.101 | −2.857 | −7.245 |
| mmu-miR-201 | 0.021 | 0.101 | −3.217 | −9.299 |
| mmu-miR-665 | 0.021 | 0.102 | −1.907 | −3.75 |
| mmu-miR-1306 | 0.022 | 0.136 | −1.915 | −3.772 |
| mmu-miR-342-3p | 0.022 | 0.104 | −1.325 | −2.505 |
| mmu-miR-693-3p | 0.022 | 0.136 | 2.36 | 5.133 |
| mmu-miR-1927 | 0.023 | 0.136 | 2.12 | 4.346 |
| mmu-miR-18b | 0.023 | 0.107 | −4.795 | −27.752 |
| mmu-miR-300* | 0.023 | 0.136 | −1.703 | −3.255 |
| mmu-miR-411* | 0.023 | 0.136 | 2.392 | 5.25 |
| mmu-miR-322* | 0.023 | 0.136 | −1.39 | −2.621 |
| mmu-miR-493 | 0.024 | 0.111 | −2.227 | −4.682 |
| mmu-miR-875-5p | 0.024 | 0.136 | 5.052 | 33.182 |
| mmu-miR-1967 | 0.024 | 0.136 | −1.948 | −3.858 |
| mmu-miR-1940 | 0.024 | 0.136 | 1.747 | 3.357 |
| mmu-miR-470* | 0.025 | 0.137 | 5.412 | 42.586 |
| mmu-miR-187 | 0.025 | 0.114 | −1.555 | −2.937 |
| mmu-miR-205 | 0.025 | 0.114 | 3.205 | 9.224 |
| mmu-miR-678 | 0.026 | 0.138 | −2.603 | −6.074 |
| mmu-miR-144 | 0.026 | 0.117 | −6.867 | −116.731 |
| mmu-miR-29a | 0.027 | 0.12 | 10.698 | 1661.144 |
| mmu-miR-20b | 0.027 | 0.12 | −1.402 | −2.643 |
| mmu-miR-145* | 0.028 | 0.144 | −2.16 | −4.47 |
| mmu-miR-694 | 0.028 | 0.144 | 2.735 | 6.657 |
| mmu-miR-2183 | 0.028 | 0.144 | 1.68 | 3.204 |
| mmu-miR-704 | 0.028 | 0.144 | −1.545 | −2.918 |
| mmu-let-7a | 0.029 | 0.127 | −1.207 | −2.309 |

TABLE 6-continued

| Fat tissue mouse miRNA signatures | | | | |
|---|---|---|---|---|
| mmu-miR-876-5p | 0.03 | 0.148 | 2.825 | 7.085 |
| mmu-miR-1950 | 0.03 | 0.148 | 3.117 | 8.678 |
| mmu-miR-101b | 0.031 | 0.129 | −1.577 | −2.984 |
| mmu-miR-455 | 0.031 | 0.129 | −2.665 | −6.34 |
| mmu-miR-129-5p | 0.031 | 0.129 | 5.353 | 40.87 |
| mmu-miR-29c | 0.032 | 0.13 | −1.287 | −2.44 |
| mmu-miR-764-5p | 0.033 | 0.159 | −1.738 | −3.335 |
| mmu-miR-182 | 0.033 | 0.135 | −2.595 | −6.04 |
| mmu-miR-1963 | 0.034 | 0.165 | −1.378 | −2.599 |
| mmu-miR-204 | 0.035 | 0.14 | −1.472 | −2.774 |
| mmu-miR-673-5p | 0.035 | 0.166 | −1.108 | −2.155 |
| mmu-miR-615-3p | 0.036 | 0.143 | −1.482 | −2.793 |
| mmu-miR-362-5p | 0.037 | 0.147 | 2.87 | 7.313 |
| mmu-miR-743a | 0.038 | 0.175 | 5.602 | 48.581 |
| mmu-let-7c | 0.039 | 0.152 | −1.032 | −2.045 |
| mmu-miR-450a-5p | 0.039 | 0.152 | −1.072 | −2.102 |
| mmu-miR-1948 | 0.04 | 0.182 | 5.07 | 33.587 |
| mmu-miR-338-3p | 0.04 | 0.153 | 1.978 | 3.939 |
| mmu-miR-133b | 0.041 | 0.153 | −3.957 | −15.531 |
| mmu-miR-652 | 0.041 | 0.154 | −1.332 | −2.518 |
| mmu-miR-193b | 0.042 | 0.154 | −1.955 | −3.876 |
| mmu-miR-191* | 0.042 | 0.189 | 1.485 | 2.799 |
| mmu-miR-713 | 0.043 | 0.19 | 1.797 | 3.476 |
| mmu-miR-497 | 0.043 | 0.158 | −1.585 | −2.999 |
| mmu-miR-702 | 0.044 | 0.19 | −1.015 | −2.021 |
| mmu-miR-29b* | 0.044 | 0.19 | 1.44 | 2.713 |
| mmu-miR-483 | 0.044 | 0.161 | 2.298 | 4.918 |
| mmu-let-7g | 0.045 | 0.161 | −1.237 | −2.357 |
| mmu-miR-1839-3p | 0.045 | 0.194 | 1.197 | 2.293 |
| mmu-miR-194 | 0.047 | 0.164 | −1.137 | −2.199 |
| mmu-miR-215 | 0.047 | 0.164 | −2.565 | −5.916 |
| mmu-miR-32 | 0.048 | 0.164 | 1.068 | 2.096 |
| mmu-miR-434-3p | 0.048 | 0.164 | 1.238 | 2.359 |
| mmu-miR-1902 | 0.048 | 0.204 | 1.652 | 3.143 |
| mmu-miR-7b | 0.048 | 0.164 | 1.878 | 3.676 |
| mmu-miR-296-3p | 0.049 | 0.164 | −1.177 | −2.261 |
| mmu-miR-411 | 0.05 | 0.164 | −1.067 | −2.095 |

| miRNA | BATvsEPI p-value | BATvsEPI FDR | BATvsEPI logFC | BATvsEPI FC |
|---|---|---|---|---|
| mmu-miR-702 | <0.0001 | <0.0001 | 4.239 | 18.883 |
| mmu-miR-805 | <0.0001 | <0.0001 | 3.734 | 13.306 |
| mmu-miR-378* | <0.0001 | <0.0001 | 4.127 | 17.467 |
| mmu-miR-1949 | <0.0001 | <0.0001 | 4.459 | 21.994 |
| mmu-miR-1963 | <0.0001 | 0.002 | 3.792 | 13.847 |
| mmu-miR-714 | <0.0001 | 0.002 | 2.502 | 5.663 |
| mmu-miR-715 | <0.0001 | 0.002 | 2.659 | 6.316 |
| mmu-miR-2134 | <0.0001 | 0.004 | 3.762 | 13.562 |
| mmu-miR-193b | <0.0001 | 0.018 | 4.789 | 27.637 |
| mmu-miR-328 | <0.0001 | 0.018 | 2.566 | 5.922 |
| mmu-miR-290-5p | <0.0001 | 0.018 | 5.104 | 34.38 |
| mmu-miR-455 | <0.0001 | 0.018 | 5.811 | 56.142 |
| mmu-miR-666-5p | <0.0001 | 0.018 | 3.129 | 8.745 |
| mmu-miR-1981 | <0.0001 | 0.011 | 2.479 | 5.575 |
| mmu-miR-1274a | <0.0001 | 0.011 | 2.214 | 4.64 |
| mmu-miR-204 | <0.0001 | 0.027 | 3.031 | 8.174 |
| mmu-miR-880 | <0.0001 | 0.015 | 9.812 | 898.6 |
| mmu-miR-193* | 0.001 | 0.015 | 2.129 | 4.374 |
| mmu-miR-182 | 0.001 | 0.027 | 5.146 | 35.408 |
| mmu-miR-1-2-as | 0.001 | 0.027 | −5.564 | −47.307 |
| mmu-miR-1942 | 0.001 | 0.016 | 6.074 | 67.37 |
| mmu-miR-761 | 0.001 | 0.016 | 2.959 | 7.776 |
| mmu-miR-883a-5p | 0.001 | 0.016 | 7.059 | 133.346 |
| mmu-miR-378 | 0.001 | 0.033 | 5.141 | 35.286 |
| mmu-miR-2182 | 0.001 | 0.016 | 2.294 | 4.904 |
| mmu-miR-763 | 0.001 | 0.016 | −1.626 | −3.086 |
| mmu-miR-1961 | 0.001 | 0.016 | −1.626 | −3.086 |
| mmu-miR-467h | 0.001 | 0.035 | 2.926 | 7.6 |
| mmu-let-7g | 0.001 | 0.035 | 2.421 | 5.355 |
| mmu-miR-1947 | 0.001 | 0.017 | 2.884 | 7.382 |
| mmu-miR-1932 | 0.001 | 0.017 | 2.879 | 7.357 |
| mmu-let-7a | 0.001 | 0.039 | 2.064 | 4.18 |
| mmu-miR-133b | 0.001 | 0.039 | 7.289 | 156.337 |
| mmu-miR-343 | 0.002 | 0.04 | 3.906 | 14.991 |
| mmu-miR-668 | 0.002 | 0.04 | 4.344 | 20.302 |
| mmu-miR-291a-5p | 0.002 | 0.041 | 5.731 | 53.114 |
| mmu-miR-10a* | 0.002 | 0.032 | 1.934 | 3.821 |

TABLE 6-continued

| Fat tissue mouse miRNA signatures | | | | |
|---|---|---|---|---|
| mmu-miR-423-5p | 0.002 | 0.051 | 1.691 | 3.229 |
| mmu-miR-706 | 0.002 | 0.037 | −1.868 | −3.651 |
| mmu-miR-27b | 0.002 | 0.053 | 1.994 | 3.982 |
| mmu-miR-1935 | 0.003 | 0.037 | −1.726 | −3.308 |
| mmu-miR-467a* | 0.003 | 0.037 | −1.511 | −2.85 |
| mmu-miR-200a* | 0.003 | 0.037 | −2.288 | −4.885 |
| mmu-miR-30c-1* | 0.003 | 0.037 | 4.214 | 18.559 |
| mmu-miR-324-5p | 0.003 | 0.064 | 3.779 | 13.723 |
| mmu-miR-718 | 0.003 | 0.037 | 3.807 | 13.992 |
| mmu-miR-1945 | 0.003 | 0.037 | 2.724 | 6.607 |
| mmu-miR-709 | 0.003 | 0.037 | 1.482 | 2.792 |
| mmu-miR-295* | 0.003 | 0.037 | 1.967 | 3.908 |
| mmu-miR-450b-3p | 0.004 | 0.07 | −2.669 | −6.36 |
| mmu-miR-503* | 0.004 | 0.039 | 1.457 | 2.744 |
| mmu-miR-1901 | 0.004 | 0.04 | 2.137 | 4.397 |
| mmu-miR-1965 | 0.004 | 0.04 | 1.762 | 3.391 |
| mmu-miR-22* | 0.004 | 0.043 | 3.164 | 8.963 |
| mmu-miR-687 | 0.005 | 0.043 | −4.218 | −18.616 |
| mmu-miR-134 | 0.005 | 0.078 | −1.756 | −3.379 |
| mmu-miR-590-3p | 0.005 | 0.078 | −1.756 | −3.379 |
| mmu-let-7e | 0.005 | 0.078 | 1.514 | 2.855 |
| mmu-miR-376c* | 0.005 | 0.043 | 5.427 | 43.008 |
| mmu-miR-1939 | 0.005 | 0.043 | 1.934 | 3.821 |
| mmu-miR-345-3p | 0.005 | 0.082 | 2.656 | 6.303 |
| mmu-miR-677 | 0.005 | 0.045 | 1.874 | 3.666 |
| mmu-miR-704 | 0.005 | 0.045 | 2.114 | 4.329 |
| mmu-miR-1896 | 0.005 | 0.045 | 1.859 | 3.628 |
| mmu-miR-25 | 0.005 | 0.084 | 3.176 | 9.038 |
| mmu-miR-216b | 0.006 | 0.085 | 3.881 | 14.733 |
| mmu-miR-322* | 0.006 | 0.047 | 1.799 | 3.48 |
| mmu-let-7d* | 0.006 | 0.047 | 2.039 | 4.11 |
| mmu-miR-26b | 0.006 | 0.086 | 2.654 | 6.292 |
| mmu-miR-99b* | 0.006 | 0.048 | 1.559 | 2.947 |
| mmu-miR-1957 | 0.006 | 0.048 | 4.317 | 19.925 |
| mmu-miR-877 | 0.007 | 0.049 | 2.049 | 4.138 |
| mmu-miR-33 | 0.007 | 0.086 | 3.406 | 10.6 |
| mmu-let-7c | 0.007 | 0.086 | 1.469 | 2.767 |
| mmu-miR-652 | 0.007 | 0.086 | 1.914 | 3.767 |
| mmu-miR-467a | 0.007 | 0.086 | 2.936 | 7.653 |
| mmu-miR-2133 | 0.007 | 0.05 | 1.589 | 3.008 |
| mmu-miR-654-3p | 0.007 | 0.087 | 2.494 | 5.631 |
| mmu-miR-676 | 0.008 | 0.053 | 1.699 | 3.247 |
| mmu-miR-369-3p | 0.008 | 0.087 | −7.101 | −137.328 |
| mmu-miR-574-5p | 0.008 | 0.087 | 5.144 | 35.347 |
| mmu-miR-302c* | 0.008 | 0.055 | 3.859 | 14.511 |
| mmu-miR-804 | 0.008 | 0.055 | 7.192 | 146.173 |
| mmu-miR-1 | 0.008 | 0.089 | 10.556 | 1505.491 |
| mmu-miR-494 | 0.009 | 0.089 | 2.181 | 4.535 |
| mmu-miR-206 | 0.009 | 0.089 | 4.736 | 26.649 |
| mmu-miR-212 | 0.009 | 0.089 | 4.411 | 21.274 |
| mmu-miR-883b-5p | 0.009 | 0.061 | 2.644 | 6.251 |
| mmu-miR-451 | 0.009 | 0.089 | 1.354 | 2.555 |
| mmu-miR-188-3p | 0.01 | 0.089 | 3.049 | 8.274 |
| mmu-miR-467b | 0.01 | 0.089 | 1.944 | 3.846 |
| mmu-miR-1962 | 0.01 | 0.063 | 1.577 | 2.983 |
| mmu-miR-1933-3p | 0.01 | 0.064 | −2.396 | −5.263 |
| mmu-miR-466i | 0.011 | 0.095 | −1.991 | −3.976 |
| mmu-miR-30b | 0.011 | 0.095 | 1.936 | 3.826 |
| mmu-miR-1186 | 0.011 | 0.068 | −1.293 | −2.451 |
| mmu-miR-1946b | 0.011 | 0.068 | −1.826 | −3.545 |
| mmu-miR-346 | 0.012 | 0.095 | 1.621 | 3.076 |
| mmu-miR-875-5p | 0.012 | 0.069 | −5.838 | −57.221 |
| mmu-miR-133a | 0.012 | 0.095 | 5.916 | 60.381 |
| mmu-miR-370 | 0.012 | 0.095 | 1.709 | 3.268 |
| mmu-miR-21 | 0.012 | 0.095 | −2.516 | −5.722 |
| mmu-miR-2146 | 0.012 | 0.071 | 1.944 | 3.848 |
| mmu-miR-326 | 0.012 | 0.097 | 1.636 | 3.108 |
| mmu-miR-127 | 0.013 | 0.1 | 2.271 | 4.827 |
| mmu-miR-2142 | 0.013 | 0.075 | 2.177 | 4.521 |
| mmu-miR-33* | 0.013 | 0.075 | −1.436 | −2.706 |
| mmu-miR-874 | 0.014 | 0.075 | 1.222 | 2.332 |
| mmu-miR-1907 | 0.014 | 0.075 | 1.184 | 2.272 |
| mmu-miR-298 | 0.014 | 0.105 | 2.024 | 4.066 |
| mmu-miR-712 | 0.014 | 0.076 | 3.187 | 9.104 |
| mmu-miR-363 | 0.014 | 0.105 | 3.021 | 8.117 |
| mmu-miR-409-5p | 0.015 | 0.105 | −1.889 | −3.704 |
| mmu-miR-133a* | 0.015 | 0.078 | 4.687 | 25.751 |
| mmu-miR-466f-3p | 0.015 | 0.105 | −1.389 | −2.619 |

TABLE 6-continued

Fat tissue mouse miRNA signatures

| miRNA | | | | |
|---|---|---|---|---|
| mmu-miR-449a | 0.015 | 0.105 | 3.704 | 13.028 |
| mmu-miR-1936 | 0.015 | 0.08 | −4.606 | −24.352 |
| mmu-miR-669e | 0.015 | 0.105 | −1.919 | −3.782 |
| mmu-miR-466a-5p | 0.015 | 0.105 | 4.236 | 18.844 |
| mmu-miR-463* | 0.015 | 0.08 | 5.034 | 32.764 |
| mmu-miR-1839-5p | 0.016 | 0.08 | 1.194 | 2.288 |
| mmu-miR-1971 | 0.016 | 0.08 | 1.769 | 3.408 |
| mmu-miR-15b* | 0.016 | 0.08 | 1.657 | 3.153 |
| mmu-miR-192 | 0.017 | 0.113 | 1.804 | 3.491 |
| mmu-miR-881* | 0.017 | 0.083 | −4.753 | −26.973 |
| mmu-miR-190b | 0.018 | 0.114 | 3.184 | 9.085 |
| mmu-miR-665 | 0.018 | 0.114 | 1.979 | 3.941 |
| mmu-miR-32 | 0.018 | 0.115 | −1.326 | −2.508 |
| mmu-miR-467g | 0.018 | 0.115 | −7.454 | −175.336 |
| mmu-miR-1938 | 0.019 | 0.088 | −4.093 | −17.071 |
| mmu-miR-106b* | 0.019 | 0.088 | −1.306 | −2.472 |
| mmu-miR-1930 | 0.019 | 0.088 | 1.234 | 2.352 |
| mmu-miR-18b | 0.021 | 0.13 | 4.871 | 29.263 |
| mmu-miR-770-5p | 0.022 | 0.1 | 2.667 | 6.349 |
| mmu-miR-222 | 0.022 | 0.133 | 2.574 | 5.953 |
| mmu-let-7b* | 0.023 | 0.105 | 1.374 | 2.592 |
| mmu-miR-101a | 0.024 | 0.14 | −2.761 | −6.781 |
| mmu-miR-183 | 0.024 | 0.14 | 5.086 | 33.966 |
| mmu-miR-425* | 0.024 | 0.107 | 3.492 | 11.248 |
| mmu-miR-31 | 0.024 | 0.14 | 1.951 | 3.866 |
| mmu-miR-882 | 0.024 | 0.107 | 5.444 | 43.533 |
| mmu-miR-203* | 0.026 | 0.112 | 2.087 | 4.247 |
| mmu-miR-27b* | 0.026 | 0.112 | 1.742 | 3.344 |
| mmu-miR-344 | 0.027 | 0.151 | −1.924 | −3.795 |
| mmu-miR-302d | 0.028 | 0.154 | 6.074 | 67.346 |
| mmu-miR-34b-3p | 0.028 | 0.156 | 2.339 | 5.058 |
| mmu-miR-105 | 0.03 | 0.165 | 5.226 | 37.427 |
| mmu-miR-223 | 0.031 | 0.165 | −1.431 | −2.697 |
| mmu-miR-340-5p | 0.032 | 0.165 | 3.599 | 12.113 |
| mmu-miR-465c-5p | 0.032 | 0.165 | 2.731 | 6.639 |
| mmu-miR-2144 | 0.032 | 0.134 | 1.997 | 3.99 |
| mmu-miR-150 | 0.032 | 0.165 | 1.361 | 2.569 |
| mmu-miR-1893 | 0.032 | 0.134 | 2.127 | 4.367 |
| mmu-miR-376b* | 0.034 | 0.141 | −2.208 | −4.622 |
| mmu-miR-669o | 0.035 | 0.144 | 0.994 | 1.992 |
| mmu-miR-338-3p | 0.035 | 0.178 | −2.041 | −4.117 |
| mmu-miR-484 | 0.036 | 0.178 | 1.104 | 2.149 |
| mmu-miR-1190 | 0.036 | 0.145 | 3.539 | 11.624 |
| mmu-miR-1892 | 0.037 | 0.145 | 2.034 | 4.095 |
| mmu-miR-449c | 0.037 | 0.184 | 3.809 | 14.011 |
| mmu-miR-365 | 0.038 | 0.184 | 1.941 | 3.84 |
| mmu-miR-680 | 0.038 | 0.15 | 1.359 | 2.565 |
| mmu-miR-669b | 0.038 | 0.184 | −3.814 | −14.064 |
| mmu-miR-1951 | 0.039 | 0.15 | 1.562 | 2.952 |
| mmu-miR-202-5p | 0.039 | 0.185 | 5.851 | 57.721 |
| mmu-miR-23b | 0.042 | 0.194 | 1.836 | 3.57 |
| mmu-miR-7a | 0.042 | 0.194 | 1.396 | 2.632 |
| mmu-let-7i* | 0.043 | 0.163 | −3.336 | −10.098 |
| mmu-miR-483 | 0.043 | 0.197 | −2.319 | −4.99 |
| mmu-miR-30e* | 0.043 | 0.163 | 1.207 | 2.308 |
| mmu-miR-24-2* | 0.044 | 0.163 | −2.326 | −5.014 |
| mmu-miR-485 | 0.044 | 0.199 | −2.164 | −4.482 |
| mmu-miR-673-5p | 0.045 | 0.166 | 1.044 | 2.062 |
| mmu-miR-684 | 0.045 | 0.166 | −1.063 | −2.09 |
| mmu-miR-28* | 0.046 | 0.166 | −1.023 | −2.033 |
| mmu-miR-452 | 0.047 | 0.209 | 1.551 | 2.93 |
| mmu-miR-31* | 0.047 | 0.168 | 2.859 | 7.255 |
| mmu-miR-409-3p | 0.048 | 0.213 | −1.779 | −3.432 |
| mmu-miR-488* | 0.048 | 0.172 | 3.197 | 9.168 |
| mmu-miR-496 | 0.049 | 0.217 | −2.199 | −4.592 |

| miRNA | BATvsING p-value | BATvsING FDR | BATvsING logFC | BATvsING FC |
|---|---|---|---|---|
| mmu-miR-378* | <0.0001 | 0.001 | 4.336 | 20.201 |
| mmu-miR-805 | <0.0001 | 0.001 | 3.596 | 12.095 |
| mmu-miR-715 | <0.0001 | 0.001 | 3.224 | 9.343 |
| mmu-miR-702 | <0.0001 | 0.001 | 3.224 | 9.343 |
| mmu-miR-1945 | <0.0001 | 0.011 | 4.039 | 16.437 |
| mmu-miR-1935 | <0.0001 | 0.015 | −2.344 | −5.076 |
| mmu-miR-1199 | <0.0001 | 0.016 | 2.256 | 4.778 |
| mmu-miR-30c-1* | <0.0001 | 0.016 | 5.636 | 49.74 |
| mmu-miR-1940 | 0.001 | 0.021 | 3.199 | 9.182 |

TABLE 6-continued

Fat tissue mouse miRNA signatures

| | | | | |
|---|---|---|---|---|
| mmu-miR-1942 | 0.001 | 0.022 | 6.009 | 64.394 |
| mmu-miR-718 | 0.001 | 0.023 | 4.671 | 25.481 |
| mmu-miR-714 | 0.001 | 0.023 | 1.756 | 3.378 |
| mmu-miR-2134 | 0.001 | 0.023 | 2.821 | 7.068 |
| mmu-miR-706 | 0.001 | 0.026 | −2.091 | −4.261 |
| mmu-miR-1932 | 0.001 | 0.026 | 2.836 | 7.142 |
| mmu-miR-299 | 0.001 | 0.425 | 7.201 | 147.184 |
| mmu-miR-1963 | 0.001 | 0.029 | 2.414 | 5.329 |
| mmu-miR-707 | 0.002 | 0.029 | 4.449 | 21.839 |
| mmu-miR-763 | 0.002 | 0.029 | −1.474 | −2.777 |
| mmu-miR-1961 | 0.002 | 0.029 | −1.474 | −2.777 |
| mmu-miR-503* | 0.002 | 0.029 | 1.626 | 3.087 |
| mmu-miR-1839-3p | 0.002 | 0.033 | 2.116 | 4.336 |
| mmu-miR-1949 | 0.002 | 0.036 | 2.046 | 4.131 |
| mmu-miR-1946a | 0.003 | 0.045 | −1.794 | −3.467 |
| mmu-miR-874 | 0.004 | 0.06 | 1.486 | 2.802 |
| mmu-miR-500 | 0.004 | 0.425 | 3.901 | 14.944 |
| mmu-miR-684 | 0.005 | 0.066 | −1.641 | −3.119 |
| mmu-miR-1901 | 0.005 | 0.066 | 2.034 | 4.095 |
| mmu-miR-99b* | 0.005 | 0.066 | 1.599 | 3.029 |
| mmu-miR-1897-3p | 0.006 | 0.066 | 2.859 | 7.254 |
| mmu-miR-10a* | 0.006 | 0.066 | 1.639 | 3.114 |
| mmu-miR-2133 | 0.006 | 0.066 | 1.629 | 3.093 |
| mmu-miR-1946b | 0.006 | 0.066 | −2.024 | −4.066 |
| mmu-miR-193b | 0.007 | 0.425 | 2.834 | 7.13 |
| mmu-miR-1191 | 0.007 | 0.068 | 3.381 | 10.42 |
| mmu-miR-689 | 0.007 | 0.072 | 3.359 | 10.259 |
| mmu-miR-223 | 0.008 | 0.425 | −1.889 | −3.703 |
| mmu-miR-15b* | 0.008 | 0.076 | 1.891 | 3.71 |
| mmu-miR-877* | 0.008 | 0.076 | 1.791 | 3.461 |
| mmu-miR-880 | 0.009 | 0.077 | 6.431 | 86.303 |
| mmu-miR-761 | 0.009 | 0.077 | 2.029 | 4.081 |
| mmu-miR-465a-5p | 0.009 | 0.425 | −1.701 | −3.251 |
| mmu-miR-1194 | 0.01 | 0.081 | −1.314 | −2.486 |
| mmu-miR-302c* | 0.01 | 0.081 | 3.754 | 13.49 |
| mmu-miR-1907 | 0.011 | 0.087 | 1.244 | 2.368 |
| mmu-miR-1274a | 0.011 | 0.087 | 1.314 | 2.486 |
| mmu-miR-191* | 0.011 | 0.087 | 1.966 | 3.908 |
| mmu-miR-21 | 0.014 | 0.425 | −2.451 | −5.468 |
| mmu-miR-148b | 0.014 | 0.425 | −1.326 | −2.507 |
| mmu-miR-455 | 0.014 | 0.425 | 3.146 | 8.855 |
| mmu-miR-703 | 0.014 | 0.108 | −1.899 | −3.729 |
| mmu-miR-883b-3p | 0.015 | 0.109 | 4.551 | 23.447 |
| mmu-miR-193* | 0.016 | 0.117 | 1.254 | 2.385 |
| mmu-miR-147 | 0.016 | 0.425 | −2.106 | −4.305 |
| mmu-miR-568 | 0.017 | 0.425 | 5.549 | 46.818 |
| mmu-miR-378 | 0.017 | 0.425 | 3.161 | 8.947 |
| mmu-miR-34c* | 0.017 | 0.119 | −1.419 | −2.673 |
| mmu-miR-669h-3p | 0.018 | 0.425 | −1.276 | −2.422 |
| mmu-miR-325 | 0.019 | 0.425 | 6.319 | 79.837 |
| mmu-miR-1904 | 0.02 | 0.139 | 1.069 | 2.098 |
| mmu-miR-433* | 0.02 | 0.139 | −3.996 | −15.957 |
| mmu-miR-682 | 0.021 | 0.144 | −3.269 | −9.637 |
| mmu-miR-208a | 0.022 | 0.425 | −4.296 | −19.644 |
| mmu-miR-339-3p | 0.022 | 0.425 | 24.721 | 27663479.2 |
| mmu-let-7d | 0.022 | 0.425 | 1.461 | 2.754 |
| mmu-miR-10b | 0.023 | 0.425 | −1.274 | −2.418 |
| mmu-miR-574-5p | 0.023 | 0.425 | −4.189 | −18.234 |
| mmu-miR-7b | 0.025 | 0.425 | 2.199 | 4.592 |
| mmu-miR-678 | 0.025 | 0.165 | −2.614 | −6.121 |
| mmu-miR-224 | 0.026 | 0.425 | −1.329 | −2.511 |
| mmu-miR-99a | 0.027 | 0.425 | −1.306 | −2.473 |
| mmu-miR-204 | 0.027 | 0.425 | 1.559 | 2.946 |
| mmu-miR-100 | 0.027 | 0.425 | −1.291 | −2.447 |
| mmu-miR-375 | 0.028 | 0.425 | 3.239 | 9.441 |
| mmu-miR-19b | 0.028 | 0.425 | −1.624 | −3.081 |
| mmu-miR-432 | 0.028 | 0.181 | −1.239 | −2.36 |
| mmu-miR-1930 | 0.029 | 0.181 | 1.131 | 2.191 |
| mmu-miR-138* | 0.03 | 0.189 | 1.834 | 3.565 |
| mmu-miR-2182 | 0.033 | 0.202 | 1.229 | 2.344 |
| mmu-miR-184 | 0.035 | 0.477 | −2.241 | −4.727 |
| mmu-miR-182 | 0.036 | 0.477 | 2.551 | 5.862 |
| mmu-miR-1965 | 0.036 | 0.216 | 1.159 | 2.233 |
| mmu-miR-337-3p | 0.037 | 0.477 | 2.224 | 4.672 |
| mmu-miR-434-3p | 0.038 | 0.477 | 1.314 | 2.486 |
| mmu-miR-409-5p | 0.038 | 0.477 | −1.539 | −2.905 |
| mmu-miR-876-5p | 0.038 | 0.225 | 2.669 | 6.359 |
| mmu-miR-488* | 0.039 | 0.226 | 3.376 | 10.384 |

TABLE 6-continued

| Fat tissue mouse miRNA signatures | | | | |
|---|---|---|---|---|
| mmu-miR-1948 | 0.041 | 0.232 | 5.039 | 32.873 |
| mmu-miR-148a | 0.042 | 0.477 | −1.009 | −2.012 |
| mmu-miR-1896 | 0.043 | 0.237 | 1.234 | 2.352 |
| mmu-miR-452 | 0.043 | 0.477 | −1.584 | −2.997 |
| mmu-miR-27a* | 0.043 | 0.237 | −1.111 | −2.16 |
| mmu-miR-2146 | 0.044 | 0.238 | 1.471 | 2.773 |
| mmu-miR-34b-5p | 0.045 | 0.477 | 2.151 | 4.443 |
| mmu-miR-187 | 0.045 | 0.477 | −1.356 | −2.56 |
| mmu-miR-134 | 0.045 | 0.477 | −1.121 | −2.175 |
| mmu-miR-590-3p | 0.045 | 0.477 | −1.121 | −2.175 |
| mmu-miR-196a* | 0.045 | 0.242 | 3.666 | 12.696 |
| mmu-miR-683 | 0.047 | 0.245 | 4.734 | 26.609 |
| mmu-miR-183* | 0.049 | 0.25 | 3.189 | 9.119 |
| mmu-miR-802 | 0.05 | 0.253 | 4.554 | 23.488 |

FDR = false discovery rate,
"*" indicates star species miRNA, in which the 3'-5' fragment induces the repression.

Figure 2C:
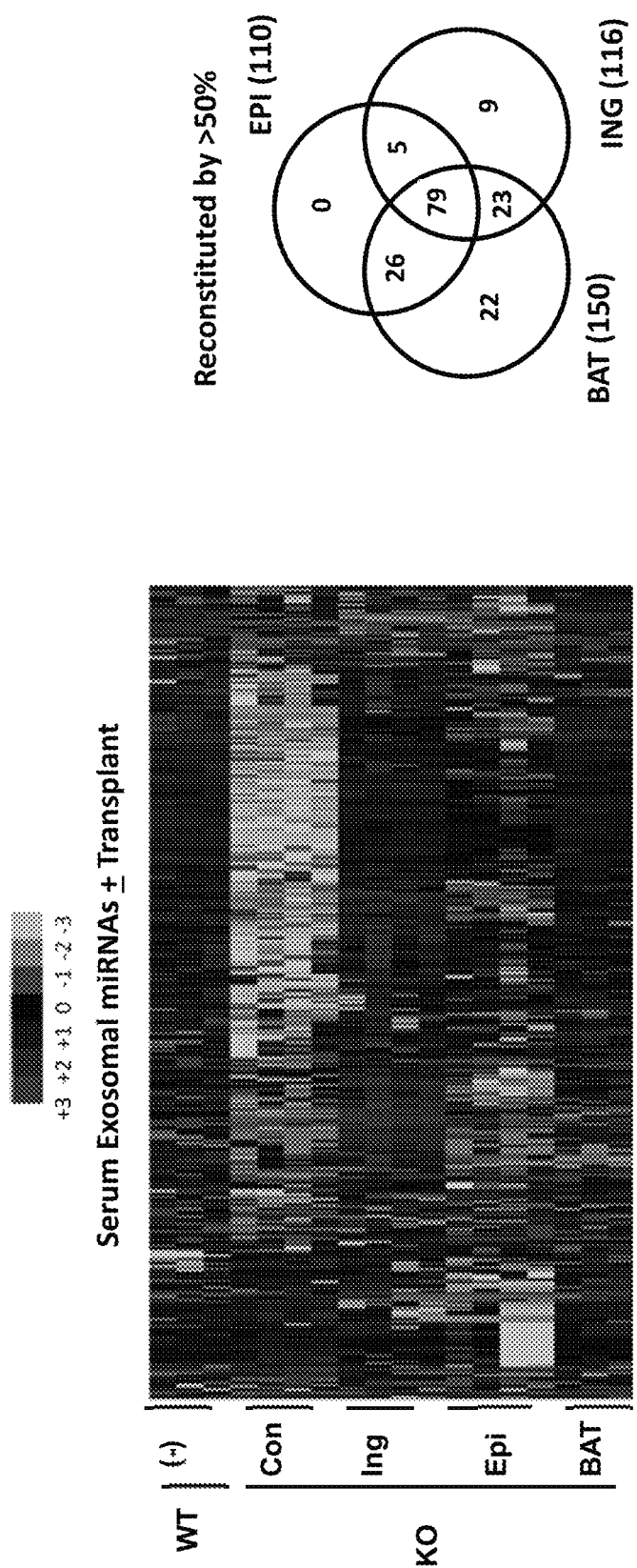

As in the first cohort, in the sham operated ADicerKO mice (KO Con) circulating exosomal miRNAs were markedly reduced compared to controls (FIG. 2c). By comparison, ADicerKO mice that received fat transplants showed remarkable restoration of circulating exosomal miRNAs (FIGS. 2c and 7d; Table 7).

TABLE 7

| Serum exosomal miRNA signatures after fat transplantation | | | | |
|---|---|---|---|---|
| miRNA | SALvsWT p-value | SALvsWT logFC | SALvsWT FC | SALvsWT FDR |
| mmu-miR-19b | <0.0001 | −14.441 | −22239.448 | <0.0001 |
| mmu-miR-19a | <0.0001 | −14.388 | −21432.314 | <0.0001 |
| mmu-miR-22 | <0.0001 | −13.074 | −8624.151 | <0.0001 |
| mmu-miR-133b | <0.0001 | −12.603 | −6222.736 | <0.0001 |
| mmu-miR-1 | <0.0001 | −11.748 | −3438.348 | <0.0001 |
| mmu-miR-29a | <0.0001 | −11.112 | −2212.814 | <0.0001 |
| mmu-miR-15a | <0.0001 | −10.894 | −1903.141 | <0.0001 |
| mmu-miR-20a | <0.0001 | −10.108 | −1103.854 | <0.0001 |
| mmu-miR-323-5p | <0.0001 | −10.104 | −1100.67 | <0.0001 |
| mmu-miR-212 | <0.0001 | −10.093 | −1092.436 | <0.0001 |
| mmu-miR-328 | <0.0001 | −10.082 | −1083.638 | <0.0001 |
| mmu-miR-106a | <0.0001 | −9.944 | −985.128 | <0.0001 |
| mmu-miR-185 | <0.0001 | −9.764 | −869.575 | <0.0001 |
| mmu-miR-133a | <0.0001 | −9.506 | −727.011 | <0.0001 |
| mmu-let-7a | <0.0001 | −9.418 | −683.833 | <0.0001 |
| mmu-miR-324-3p | <0.0001 | −9.361 | −657.494 | 0.001 |
| mmu-miR-101b | <0.0001 | −8.952 | −495.131 | <0.0001 |
| mmu-miR-291a-5p | <0.0001 | −8.915 | −482.706 | <0.0001 |
| mmu-let-7g | <0.0001 | −8.893 | −475.51 | <0.0001 |
| mmu-miR-130a | <0.0001 | −8.788 | −442.132 | <0.0001 |
| mmu-miR-92b | <0.0001 | −8.541 | −372.432 | <0.0001 |
| mmu-miR-103 | <0.0001 | −8.508 | −363.926 | <0.0001 |
| mmu-miR-93 | <0.0001 | −8.392 | −335.848 | <0.0001 |
| mmu-miR-128 | <0.0001 | −8.328 | −321.424 | <0.0001 |
| mmu-miR-29c | <0.0001 | −8.314 | −318.283 | <0.0001 |
| mmu-miR-301a | <0.0001 | −8.168 | −287.516 | <0.0001 |
| mmu-miR-127 | <0.0001 | −8.118 | −277.722 | <0.0001 |
| mmu-miR-146a | <0.0001 | −8.107 | −275.645 | <0.0001 |
| mmu-miR-326 | <0.0001 | −8.094 | −273.267 | <0.0001 |
| mmu-miR-200a | <0.0001 | −8.007 | −257.186 | <0.0001 |
| mmu-miR-101a | <0.0001 | −7.998 | −255.557 | <0.0001 |
| mmu-miR-193b | <0.0001 | −7.954 | −247.995 | <0.0001 |
| mmu-miR-148b | <0.0001 | −7.684 | −205.667 | <0.0001 |
| mmu-miR-338-5p | <0.0001 | −7.679 | −204.955 | <0.0001 |
| mmu-miR-21* | <0.0001 | −7.644 | −200.043 | 0.019 |
| mmu-miR-130b | <0.0001 | −7.536 | −185.572 | <0.0001 |
| mmu-miR-20b | <0.0001 | −7.501 | −181.124 | <0.0001 |
| mmu-miR-140 | <0.0001 | −7.428 | −172.147 | <0.0001 |
| mmu-let-7e | <0.0001 | −7.271 | −154.433 | <0.0001 |
| mmu-miR-92a | <0.0001 | −7.203 | −147.374 | <0.0001 |
| mmu-miR-30b | <0.0001 | −7.128 | −139.908 | <0.0001 |
| mmu-miR-320 | <0.0001 | −7.123 | −139.424 | <0.0001 |
| mmu-miR-214 | <0.0001 | −7.084 | −135.69 | <0.0001 |
| mmu-miR-186 | <0.0001 | −7.078 | −135.064 | 0.001 |
| mmu-miR-27a | <0.0001 | −7.048 | −132.284 | <0.0001 |
| mmu-miR-127* | <0.0001 | −7.001 | −128.074 | <0.0001 |
| mmu-miR-107 | <0.0001 | −6.951 | −123.711 | <0.0001 |

TABLE 7-continued

Serum exosomal miRNA signatures after fat transplantation

| | | | |
|---|---|---|---|
| mmu-miR-188-3p | <0.0001 | −6.916 | −120.746 | <0.0001 |
| mmu-miR-183 | <0.0001 | −6.908 | −120.051 | 0.002 |
| mmu-miR-207 | <0.0001 | −6.888 | −118.398 | <0.0001 |
| mmu-miR-205 | <0.0001 | −6.884 | −118.125 | <0.0001 |
| mmu-miR-125a-5p | <0.0001 | −6.868 | −116.768 | 0.04 |
| mmu-miR-195 | <0.0001 | −6.799 | −111.366 | <0.0001 |
| mmu-miR-100 | <0.0001 | −6.769 | −109.074 | <0.0001 |
| mmu-miR-32 | <0.0001 | −6.584 | −95.947 | <0.0001 |
| mmu-miR-199a-3p | <0.0001 | −6.54 | −93.054 | <0.0001 |
| mmu-miR-26a | <0.0001 | −6.473 | −88.852 | 0.003 |
| mmu-miR-24 | <0.0001 | −6.449 | −87.376 | <0.0001 |
| mmu-miR-16 | <0.0001 | −6.388 | −83.768 | <0.0001 |
| mmu-miR-324-5p | <0.0001 | −6.378 | −83.19 | <0.0001 |
| mmu-let-7d | <0.0001 | −6.369 | −82.663 | 0.019 |
| mmu-miR-335-3p | <0.0001 | −6.343 | −81.149 | <0.0001 |
| mmu-miR-199a-5p | <0.0001 | −6.338 | −80.868 | <0.0001 |
| mmu-miR-539 | <0.0001 | −6.318 | −79.801 | 0.072 |
| mmu-miR-187 | <0.0001 | −6.29 | −78.249 | 0.03 |
| mmu-miR-34a | <0.0001 | −6.289 | −78.204 | <0.0001 |
| mmu-miR-181d | <0.0001 | −6.185 | −72.756 | <0.0001 |
| mmu-miR-25 | <0.0001 | −6.17 | −72.004 | <0.0001 |
| mmu-miR-222 | <0.0001 | −6.042 | −65.875 | <0.0001 |
| mmu-miR-148a | <0.0001 | −5.957 | −62.106 | <0.0001 |
| mmu-miR-18a | <0.0001 | −5.884 | −59.062 | 0.002 |
| mmu-miR-297a | <0.0001 | −5.865 | −58.283 | 0.001 |
| mmu-miR-204 | <0.0001 | −5.844 | −57.447 | <0.0001 |
| mmu-let-7c | <0.0001 | −5.816 | −56.33 | <0.0001 |
| mmu-miR-21 | <0.0001 | −5.704 | −52.135 | <0.0001 |
| mmu-miR-125a-3p | <0.0001 | −5.691 | −51.655 | 0.002 |
| mmu-miR-145 | <0.0001 | −5.638 | −49.78 | <0.0001 |
| mmu-miR-350 | 0.015 | −5.615 | −49.01 | 0.04 |
| mmu-miR-542-3p | 0.009 | −5.531 | −46.232 | 0.026 |
| mmu-miR-199b | <0.0001 | −5.485 | −44.787 | 0.002 |
| mmu-miR-99a | <0.0001 | −5.466 | −44.196 | <0.0001 |
| mmu-miR-150 | 0.005 | −5.416 | −42.69 | 0.015 |
| mmu-miR-134 | 0.001 | −5.385 | −41.788 | 0.003 |
| mmu-miR-200b | <0.0001 | −5.381 | −41.667 | 0.001 |
| mmu-miR-30e* | 0.003 | −5.377 | −41.547 | 0.011 |
| mmu-miR-218 | 0.003 | −5.365 | −41.212 | 0.011 |
| mmu-miR-346 | 0.005 | −5.363 | −41.141 | 0.015 |
| mmu-miR-194 | 0.002 | −5.348 | −40.739 | 0.007 |
| mmu-let-7b | <0.0001 | −5.338 | −40.457 | 0.001 |
| mmu-miR-181a | 0.011 | −5.316 | −39.831 | 0.03 |
| mmu-miR-301b | 0.003 | −5.316 | −39.831 | 0.009 |
| mmu-miR-598 | <0.0001 | −5.304 | −39.511 | 0.001 |
| mmu-miR-125b-3p | 0.001 | −5.274 | −38.697 | 0.003 |
| mmu-miR-125b-5p | <0.0001 | −5.268 | −38.541 | <0.0001 |
| mmu-miR-129-5p | <0.0001 | −5.251 | −38.077 | 0.001 |
| mmu-miR-197 | <0.0001 | −5.221 | −37.293 | <0.0001 |
| mmu-miR-706 | <0.0001 | −5.098 | −34.237 | 0.002 |
| mmu-miR-183* | 0.023 | −5.044 | −32.995 | 0.055 |
| mmu-miR-302c | <0.0001 | −5.041 | −32.919 | 0.001 |
| mmu-miR-135a* | 0.013 | −4.998 | −31.945 | 0.035 |
| mmu-miR-30d | <0.0001 | −4.985 | −31.669 | <0.0001 |
| mmu-miR-139-5p | 0.001 | −4.968 | −31.287 | 0.004 |
| mmu-miR-221 | <0.0001 | −4.961 | −31.143 | 0.001 |
| mmu-miR-339-5p | 0.002 | −4.898 | −29.823 | 0.007 |
| mmu-miR-149 | 0.002 | −4.879 | −29.429 | 0.007 |
| mmu-miR-298 | 0.001 | −4.878 | −29.395 | 0.002 |
| mmu-miR-7a | <0.0001 | −4.831 | −28.459 | 0.002 |
| mmu-miR-129-3p | 0.004 | −4.771 | −27.3 | 0.014 |
| mmu-miR-155 | <0.0001 | −4.714 | −26.249 | 0.001 |
| mmu-miR-142-5p | <0.0001 | −4.694 | −25.887 | <0.0001 |
| mmu-miR-26b | 0.001 | −4.678 | −25.605 | 0.004 |
| mmu-miR-146b | 0.01 | −4.623 | −24.647 | 0.028 |
| mmu-miR-181b | 0.02 | −4.428 | −21.518 | 0.05 |
| mmu-miR-188-5p | 0.001 | −4.411 | −21.271 | 0.002 |
| mmu-miR-33 | 0.002 | −4.371 | −20.69 | 0.007 |
| mmu-miR-27b | <0.0001 | −4.336 | −20.194 | 0.001 |
| mmu-miR-191 | <0.0001 | −4.3 | −19.698 | 0.001 |
| mmu-miR-300 | 0.03 | −4.271 | −19.304 | 0.068 |
| mmu-miR-196a | 0.004 | −4.219 | −18.625 | 0.013 |
| mmu-let-7a* | 0.015 | −4.218 | −18.603 | 0.039 |
| mmu-miR-1943 | 0.003 | −4.191 | −18.263 | 0.009 |
| mmu-miR-31* | 0.003 | −4.183 | −18.168 | 0.009 |
| mmu-miR-345-5p | 0.017 | −4.112 | −17.288 | 0.044 |
| mmu-let-7d* | 0.001 | −4.044 | −16.497 | 0.002 |
| mmu-miR-711 | 0.035 | −4.043 | −16.488 | 0.076 |

TABLE 7-continued

Serum exosomal miRNA signatures after fat transplantation

| | | | | |
|---|---|---|---|---|
| mmu-miR-17 | <0.0001 | −3.975 | −15.725 | 0.002 |
| mmu-miR-342-3p | 0.011 | −3.922 | −15.154 | 0.03 |
| mmu-miR-210 | 0.03 | −3.896 | −14.885 | 0.068 |
| mmu-miR-1934 | 0.042 | −3.852 | −14.437 | 0.088 |
| mmu-miR-670 | 0.007 | −3.834 | −14.263 | 0.02 |
| mmu-miR-139-3p | 0.004 | −3.81 | −14.026 | 0.014 |
| mmu-miR-322 | 0.023 | −3.804 | −13.969 | 0.055 |
| mmu-miR-124 | 0.024 | −3.799 | −13.921 | 0.057 |
| mmu-miR-196a* | 0.011 | −3.796 | −13.889 | 0.031 |
| mmu-miR-879* | 0.013 | −3.746 | −13.416 | 0.036 |
| mmu-miR-15b | <0.0001 | −3.739 | −13.354 | 0.002 |
| mmu-miR-296-3p | 0.004 | −3.698 | −12.981 | 0.013 |
| mmu-miR-10b | 0.029 | −3.655 | −12.597 | 0.066 |
| mmu-miR-92a* | 0.044 | −3.595 | −12.084 | 0.091 |
| mmu-miR-296-5p | 0.033 | −3.564 | −11.828 | 0.073 |
| mmu-miR-770-3p | 0.005 | −3.548 | −11.692 | 0.016 |
| mmu-miR-872* | 0.038 | −3.521 | −11.478 | 0.08 |
| mmu-miR-10a | 0.002 | −3.463 | −11.03 | 0.006 |
| mmu-miR-511 | 0.036 | −3.423 | −10.728 | 0.077 |
| mmu-miR-151-5p | 0.037 | −3.422 | −10.716 | 0.079 |
| mmu-miR-2140 | <0.0001 | −3.417 | −10.679 | 0.002 |
| mmu-miR-337-3p | 0.033 | −3.386 | −10.453 | 0.072 |
| mmu-miR-1895 | 0.021 | −3.322 | −9.998 | 0.051 |
| mmu-miR-669i | 0.048 | −3.215 | −9.286 | 0.096 |
| mmu-miR-497 | 0.019 | −3.214 | −9.28 | 0.048 |
| mmu-miR-493 | 0.001 | −3.123 | −8.714 | 0.005 |
| mmu-miR-669m | 0.034 | −3.118 | −8.679 | 0.073 |
| mmu-miR-1196 | 0.001 | −3.096 | −8.549 | 0.003 |
| mmu-miR-1983 | 0.044 | −3.031 | −8.173 | 0.091 |
| mmu-miR-1955 | 0.02 | −2.999 | −7.995 | 0.05 |
| mmu-miR-1197 | 0.003 | −2.986 | −7.922 | 0.01 |
| mmu-miR-760 | 0.025 | −2.98 | −7.89 | 0.059 |
| mmu-miR-152 | 0.005 | −2.977 | −7.872 | 0.015 |
| mmu-miR-1954 | 0.007 | −2.934 | −7.643 | 0.02 |
| mmu-miR-30e | 0.036 | −2.893 | −7.43 | 0.077 |
| mmu-miR-1898 | 0.013 | −2.878 | −7.353 | 0.035 |
| mmu-miR-467e* | 0.045 | −2.86 | −7.26 | 0.092 |
| mmu-miR-1899 | 0.006 | −2.814 | −7.033 | 0.017 |
| mmu-miR-540-3p | 0.03 | −2.798 | −6.952 | 0.068 |
| mmu-miR-203 | 0.008 | −2.762 | −6.782 | 0.022 |
| mmu-miR-291b-5p | 0.044 | −2.7 | −6.498 | 0.091 |
| mmu-miR-99b | 0.012 | −2.453 | −5.474 | 0.033 |
| mmu-miR-151-3p | 0.018 | −2.448 | −5.458 | 0.047 |
| mmu-miR-20b* | 0.032 | −2.411 | −5.318 | 0.072 |
| mmu-miR-1952 | 0.042 | −2.26 | −4.79 | 0.087 |
| mmu-miR-126-5p | 0.021 | −2.157 | −4.459 | 0.051 |
| mmu-miR-2136 | 0.019 | −2.138 | −4.4 | 0.047 |
| mmu-miR-130b* | 0.027 | −2.123 | −4.357 | 0.064 |
| mmu-miR-184 | 0.015 | −2.086 | −4.245 | 0.039 |
| mmu-miR-99b* | 0.012 | −2.067 | −4.189 | 0.032 |
| mmu-miR-876-3p | 0.03 | −1.978 | −3.94 | 0.068 |
| mmu-miR-2133 | 0.032 | −1.668 | −3.177 | 0.071 |

| miRNA | INGvsSAL p-value | INGvsSAL logFC | INGvsSAL FC | INGvsSAL FDR |
|---|---|---|---|---|
| mmu-miR-19a | <0.0001 | 12.755 | 6912.539 | <0.0001 |
| mmu-miR-19b | <0.0001 | 12.303 | 5051.514 | <0.0001 |
| mmu-miR-22 | <0.0001 | 10.543 | 1491.45 | <0.0001 |
| mmu-miR-323-5p | <0.0001 | 11.22 | 2385.374 | <0.0001 |
| mmu-miR-204 | <0.0001 | 11.985 | 4053.634 | <0.0001 |
| mmu-miR-193b | <0.0001 | 8.535 | 370.929 | <0.0001 |
| mmu-let-7a | <0.0001 | 8.408 | 339.555 | <0.0001 |
| mmu-miR-92b | <0.0001 | 7.078 | 135.064 | <0.0001 |
| mmu-miR-17 | <0.0001 | −8.54 | −372.217 | <0.0001 |
| mmu-miR-15a | <0.0001 | 8.268 | 308.152 | <0.0001 |
| mmu-miR-101a | <0.0001 | 9.16 | 572.051 | <0.0001 |
| mmu-miR-133b | <0.0001 | 9.42 | 685.019 | <0.0001 |
| mmu-miR-183 | <0.0001 | 12.338 | 5175.563 | <0.0001 |
| mmu-miR-185 | <0.0001 | 6.898 | 119.221 | <0.0001 |
| mmu-miR-212 | <0.0001 | 8.98 | 504.951 | <0.0001 |
| mmu-miR-199a-5p | <0.0001 | 6.27 | 77.172 | <0.0001 |
| mmu-miR-129-3p | <0.0001 | 10.5 | 1448.155 | <0.0001 |
| mmu-miR-124 | <0.0001 | 11.1 | 2194.992 | <0.0001 |
| mmu-miR-29a | <0.0001 | 9.893 | 950.472 | <0.0001 |
| mmu-miR-130a | <0.0001 | 8.04 | 263.197 | <0.0001 |
| mmu-miR-188-3p | <0.0001 | 6.255 | 76.373 | <0.0001 |
| mmu-miR-207 | <0.0001 | 5.495 | 45.098 | <0.0001 |

TABLE 7-continued

Serum exosomal miRNA signatures after fat transplantation

| | | | | |
|---|---|---|---|---|
| mmu-miR-7a | <0.0001 | 7.49 | 179.769 | <0.0001 |
| mmu-miR-291a-5p | <0.0001 | 6.63 | 99.044 | <0.0001 |
| mmu-miR-200b | <0.0001 | −7.92 | −242.191 | <0.0001 |
| mmu-miR-27a | <0.0001 | 6.25 | 76.109 | <0.0001 |
| mmu-miR-181d | <0.0001 | 7.158 | 142.765 | <0.0001 |
| mmu-miR-706 | <0.0001 | 7.285 | 155.957 | <0.0001 |
| mmu-miR-1955 | <0.0001 | 7.05 | 132.514 | <0.0001 |
| mmu-let-7c | <0.0001 | 4.545 | 23.344 | <0.0001 |
| mmu-miR-129-5p | <0.0001 | 6.298 | 78.657 | <0.0001 |
| mmu-miR-30d | <0.0001 | 4.908 | 30.013 | <0.0001 |
| mmu-let-7e | <0.0001 | 5.223 | 37.336 | <0.0001 |
| mmu-miR-24 | <0.0001 | 4.8 | 27.858 | <0.0001 |
| mmu-miR-148a | <0.0001 | 4.993 | 31.834 | <0.0001 |
| mmu-miR-30b | <0.0001 | 7.488 | 179.458 | <0.0001 |
| mmu-miR-148b | <0.0001 | 6.333 | 80.588 | <0.0001 |
| mmu-miR-335-3p | <0.0001 | 6.225 | 74.802 | <0.0001 |
| mmu-miR-20a | <0.0001 | 7.29 | 156.498 | <0.0001 |
| mmu-miR-328 | <0.0001 | 7.845 | 229.922 | <0.0001 |
| mmu-miR-188-5p | <0.0001 | 5.585 | 48.001 | <0.0001 |
| mmu-miR-184 | <0.0001 | 3.998 | 15.972 | <0.0001 |
| mmu-miR-99a | <0.0001 | 4.658 | 25.238 | <0.0001 |
| mmu-miR-598 | <0.0001 | 5.9 | 59.714 | <0.0001 |
| mmu-let-7g | <0.0001 | 7.613 | 195.7 | <0.0001 |
| mmu-miR-100 | <0.0001 | 5.633 | 49.608 | <0.0001 |
| mmu-miR-127 | <0.0001 | 7.498 | 180.706 | <0.0001 |
| mmu-miR-106a | <0.0001 | 6.918 | 120.886 | <0.0001 |
| mmu-miR-338-5p | <0.0001 | 6.39 | 83.865 | <0.0001 |
| mmu-miR-134 | <0.0001 | 6.28 | 77.708 | <0.0001 |
| mmu-miR-133a | <0.0001 | 6.483 | 89.418 | 0.001 |
| mmu-miR-195 | <0.0001 | 4.053 | 16.593 | 0.001 |
| mmu-miR-149 | <0.0001 | 6.098 | 68.475 | 0.001 |
| mmu-miR-20b | <0.0001 | 4.58 | 23.918 | 0.001 |
| mmu-miR-25 | <0.0001 | 3.915 | 15.085 | 0.001 |
| mmu-miR-125a-3p | <0.0001 | 5.823 | 56.591 | 0.001 |
| mmu-miR-770-3p | <0.0001 | 4.848 | 28.79 | 0.001 |
| mmu-miR-92a | <0.0001 | 4.04 | 16.45 | 0.001 |
| mmu-miR-101b | <0.0001 | 6.655 | 100.775 | 0.001 |
| mmu-miR-125b-5p | <0.0001 | 4.413 | 21.296 | 0.001 |
| mmu-miR-326 | <0.0001 | 5.493 | 45.02 | 0.001 |
| mmu-miR-205 | <0.0001 | 3.85 | 14.42 | 0.002 |
| mmu-miR-31* | <0.0001 | 5.033 | 32.729 | 0.002 |
| mmu-miR-301a | <0.0001 | 5.868 | 58.384 | 0.002 |
| mmu-miR-218 | <0.0001 | 6.515 | 91.456 | 0.002 |
| mmu-miR-127* | <0.0001 | 4.603 | 24.294 | 0.002 |
| mmu-miR-26b | <0.0001 | 4.788 | 27.617 | 0.002 |
| mmu-miR-16 | <0.0001 | 3.32 | 9.987 | 0.002 |
| mmu-miR-291b-5p | <0.0001 | −4.975 | −31.45 | 0.002 |
| mmu-miR-222 | <0.0001 | 3.593 | 12.063 | 0.002 |
| mmu-miR-1 | 0.001 | 5.798 | 55.619 | 0.003 |
| mmu-miR-320 | 0.001 | 4.708 | 26.128 | 0.003 |
| mmu-miR-145 | 0.001 | 3.14 | 8.815 | 0.004 |
| mmu-miR-27b | 0.001 | 3.368 | 10.321 | 0.004 |
| mmu-miR-191 | 0.001 | 3.275 | 9.68 | 0.004 |
| mmu-miR-93 | 0.001 | 4.613 | 24.463 | 0.004 |
| mmu-miR-128 | 0.001 | 3.29 | 9.781 | 0.005 |
| mmu-miR-146a | 0.001 | 4.66 | 25.281 | 0.005 |
| mmu-miR-298 | 0.001 | 4.085 | 16.971 | 0.005 |
| mmu-miR-200a | 0.001 | 4.88 | 29.446 | 0.005 |
| mmu-let-7d* | 0.001 | 3.365 | 10.303 | 0.005 |
| mmu-miR-342-3p | 0.002 | 4.775 | 27.379 | 0.006 |
| mmu-miR-199a-3p | 0.002 | 4.063 | 16.708 | 0.007 |
| mmu-miR-197 | 0.002 | 3.413 | 10.648 | 0.007 |
| mmu-miR-186 | 0.002 | 4.88 | 29.446 | 0.007 |
| mmu-miR-1196 | 0.002 | 2.538 | 5.806 | 0.007 |
| mmu-miR-142-5p | 0.003 | −2.678 | −6.397 | 0.01 |
| mmu-miR-130b | 0.003 | 4.528 | 23.063 | 0.01 |
| mmu-let-7b | 0.003 | 3.515 | 11.432 | 0.011 |
| mmu-miR-297a | 0.003 | 4.095 | 17.089 | 0.012 |
| mmu-miR-32 | 0.004 | 3.903 | 14.954 | 0.013 |
| mmu-miR-214 | 0.004 | 3.253 | 9.53 | 0.013 |
| mmu-miR-324-3p | 0.004 | 6.188 | 72.882 | 0.014 |
| mmu-miR-346 | 0.004 | 5.025 | 32.559 | 0.014 |
| mmu-miR-152 | 0.005 | 2.738 | 6.669 | 0.015 |
| mmu-miR-33 | 0.005 | 3.585 | 12 | 0.016 |
| mmu-miR-1952 | 0.005 | 3.058 | 8.325 | 0.016 |
| mmu-miR-196a | 0.005 | −3.763 | −13.571 | 0.016 |
| mmu-miR-181b | 0.005 | 5.09 | 34.06 | 0.017 |
| mmu-let-7d | 0.006 | 5.99 | 63.558 | 0.017 |

TABLE 7-continued

Serum exosomal miRNA signatures after fat transplantation

| miRNA | | | | |
|---|---|---|---|---|
| mmu-miR-872* | 0.007 | 4.478 | 22.277 | 0.02 |
| mmu-miR-30e* | 0.007 | 4.493 | 22.51 | 0.02 |
| mmu-miR-194 | 0.007 | 4.13 | 17.509 | 0.021 |
| mmu-miR-187 | 0.008 | 6.115 | 69.31 | 0.022 |
| mmu-miR-221 | 0.008 | 2.783 | 6.88 | 0.022 |
| mmu-miR-155 | 0.008 | 2.848 | 7.198 | 0.023 |
| mmu-miR-99b | 0.008 | 2.413 | 5.324 | 0.023 |
| mmu-miR-34a | 0.01 | −2.423 | −5.361 | 0.027 |
| mmu-miR-302c | 0.011 | 2.865 | 7.285 | 0.029 |
| mmu-miR-301b | 0.012 | 3.925 | 15.189 | 0.031 |
| mmu-miR-183* | 0.013 | 5.19 | 36.504 | 0.033 |
| mmu-miR-130b* | 0.015 | 2.213 | 4.635 | 0.036 |
| mmu-miR-139-5p | 0.016 | 3.123 | 8.709 | 0.039 |
| mmu-miR-30e | 0.016 | −3.143 | −8.831 | 0.039 |
| mmu-miR-1983 | 0.018 | 3.385 | 10.447 | 0.043 |
| mmu-miR-345-5p | 0.023 | 3.618 | 12.274 | 0.052 |
| mmu-miR-135a* | 0.023 | 4.153 | 17.784 | 0.052 |
| mmu-miR-669m | 0.023 | 3.113 | 8.649 | 0.053 |
| mmu-miR-139-3p | 0.025 | 2.633 | 6.201 | 0.055 |
| mmu-miR-337-3p | 0.027 | 3.273 | 9.663 | 0.059 |
| mmu-miR-324-5p | 0.027 | 2.708 | 6.532 | 0.06 |
| mmu-miR-107 | 0.027 | 2.178 | 4.524 | 0.06 |
| mmu-miR-296-3p | 0.031 | 2.405 | 5.296 | 0.067 |
| mmu-miR-467e* | 0.033 | 2.838 | 7.148 | 0.071 |
| mmu-miR-199b | 0.033 | 2.68 | 6.409 | 0.071 |
| mmu-miR-493 | 0.035 | 1.74 | 3.34 | 0.073 |
| mmu-miR-1954 | 0.036 | 2 | 4 | 0.074 |
| mmu-miR-760 | 0.037 | 2.528 | 5.766 | 0.077 |
| mmu-miR-210 | 0.037 | 3.443 | 10.872 | 0.077 |
| mmu-miR-29c | 0.038 | 2.983 | 7.904 | 0.078 |
| mmu-miR-203 | 0.041 | −1.858 | −3.624 | 0.084 |
| mmu-miR-15b | 0.042 | 1.738 | 3.335 | 0.084 |
| mmu-miR-103 | 0.042 | 1.703 | 3.255 | 0.084 |
| mmu-miR-879* | 0.044 | 2.723 | 6.6 | 0.087 |
| mmu-miR-339-5p | 0.044 | 2.683 | 6.42 | 0.087 |

| miRNA | INGvsSAL p-value | INGvsSAL logFC | INGvsSAL FC | INGvsSAL FDR |
|---|---|---|---|---|
| mmu-miR-19a | <0.0001 | 12.755 | 6912.539 | <0.0001 |
| mmu-miR-19b | <0.0001 | 12.303 | 5051.514 | <0.0001 |
| mmu-miR-22 | <0.0001 | 10.543 | 1491.45 | <0.0001 |
| mmu-miR-323-5p | <0.0001 | 11.22 | 2385.374 | <0.0001 |
| mmu-miR-204 | <0.0001 | 11.985 | 4053.634 | <0.0001 |
| mmu-miR-193b | <0.0001 | 8.535 | 370.929 | <0.0001 |
| mmu-let-7a | <0.0001 | 8.408 | 339.555 | <0.0001 |
| mmu-miR-92b | <0.0001 | 7.078 | 135.064 | <0.0001 |
| mmu-miR-17 | <0.0001 | −8.54 | −372.217 | <0.0001 |
| mmu-miR-15a | <0.0001 | 8.268 | 308.152 | <0.0001 |
| mmu-miR-101a | <0.0001 | 9.16 | 572.051 | <0.0001 |
| mmu-miR-133b | <0.0001 | 9.42 | 685.019 | <0.0001 |
| mmu-miR-183 | <0.0001 | 12.338 | 5175.563 | <0.0001 |
| mmu-miR-185 | <0.0001 | 6.898 | 119.221 | <0.0001 |
| mmu-miR-212 | <0.0001 | 8.98 | 504.951 | <0.0001 |
| mmu-miR-199a-5p | <0.0001 | 6.27 | 77.172 | <0.0001 |
| mmu-miR-129-3p | <0.0001 | 10.5 | 1448.155 | <0.0001 |
| mmu-miR-124 | <0.0001 | 11.1 | 2194.992 | <0.0001 |
| mmu-miR-29a | <0.0001 | 9.893 | 950.472 | <0.0001 |
| mmu-miR-130a | <0.0001 | 8.04 | 263.197 | <0.0001 |
| mmu-miR-188-3p | <0.0001 | 6.255 | 76.373 | <0.0001 |
| mmu-miR-207 | <0.0001 | 5.495 | 45.098 | <0.0001 |
| mmu-miR-7a | <0.0001 | 7.49 | 179.769 | <0.0001 |
| mmu-miR-291a-5p | <0.0001 | 6.63 | 99.044 | <0.0001 |
| mmu-miR-200b | <0.0001 | −7.92 | −242.191 | <0.0001 |
| mmu-miR-27a | <0.0001 | 6.25 | 76.109 | <0.0001 |
| mmu-miR-181d | <0.0001 | 7.158 | 142.765 | <0.0001 |
| mmu-miR-706 | <0.0001 | 7.285 | 155.957 | <0.0001 |
| mmu-miR-1955 | <0.0001 | 7.05 | 132.514 | <0.0001 |
| mmu-let-7c | <0.0001 | 4.545 | 23.344 | <0.0001 |
| mmu-miR-129-5p | <0.0001 | 6.298 | 78.657 | <0.0001 |
| mmu-miR-30d | <0.0001 | 4.908 | 30.013 | <0.0001 |
| mmu-let-7e | <0.0001 | 5.223 | 37.336 | <0.0001 |
| mmu-miR-24 | <0.0001 | 4.8 | 27.858 | <0.0001 |
| mmu-miR-148a | <0.0001 | 4.993 | 31.834 | <0.0001 |
| mmu-miR-30b | <0.0001 | 7.488 | 179.458 | <0.0001 |
| mmu-miR-148b | <0.0001 | 6.333 | 80.588 | <0.0001 |
| mmu-miR-335-3p | <0.0001 | 6.225 | 74.802 | <0.0001 |
| mmu-miR-20a | <0.0001 | 7.29 | 156.498 | <0.0001 |

TABLE 7-continued

Serum exosomal miRNA signatures after fat transplantation

| | | | | |
|---|---|---|---|---|
| mmu-miR-328 | <0.0001 | 7.845 | 229.922 | <0.0001 |
| mmu-miR-188-5p | <0.0001 | 5.585 | 48.001 | <0.0001 |
| mmu-miR-184 | <0.0001 | 3.998 | 15.972 | <0.0001 |
| mmu-miR-99a | <0.0001 | 4.658 | 25.238 | <0.0001 |
| mmu-miR-598 | <0.0001 | 5.9 | 59.714 | <0.0001 |
| mmu-let-7g | <0.0001 | 7.613 | 195.7 | <0.0001 |
| mmu-miR-100 | <0.0001 | 5.633 | 49.608 | <0.0001 |
| mmu-miR-127 | <0.0001 | 7.498 | 180.706 | <0.0001 |
| mmu-miR-106a | <0.0001 | 6.918 | 120.886 | <0.0001 |
| mmu-miR-338-5p | <0.0001 | 6.39 | 83.865 | <0.0001 |
| mmu-miR-134 | <0.0001 | 6.28 | 77.708 | <0.0001 |
| mmu-miR-133a | <0.0001 | 6.483 | 89.418 | 0.001 |
| mmu-miR-195 | <0.0001 | 4.053 | 16.593 | 0.001 |
| mmu-miR-149 | <0.0001 | 6.098 | 68.475 | 0.001 |
| mmu-miR-20b | <0.0001 | 4.58 | 23.918 | 0.001 |
| mmu-miR-25 | <0.0001 | 3.915 | 15.085 | 0.001 |
| mmu-miR-125a-3p | <0.0001 | 5.823 | 56.591 | 0.001 |
| mmu-miR-770-3p | <0.0001 | 4.848 | 28.79 | 0.001 |
| mmu-miR-92a | <0.0001 | 4.04 | 16.45 | 0.001 |
| mmu-miR-101b | <0.0001 | 6.655 | 100.775 | 0.001 |
| mmu-miR-125b-5p | <0.0001 | 4.413 | 21.296 | 0.001 |
| mmu-miR-326 | <0.0001 | 5.493 | 45.02 | 0.001 |
| mmu-miR-205 | <0.0001 | 3.85 | 14.42 | 0.002 |
| mmu-miR-31* | <0.0001 | 5.033 | 32.729 | 0.002 |
| mmu-miR-301a | <0.0001 | 5.868 | 58.384 | 0.002 |
| mmu-miR-218 | <0.0001 | 6.515 | 91.456 | 0.002 |
| mmu-miR-127* | <0.0001 | 4.603 | 24.294 | 0.002 |
| mmu-miR-26b | <0.0001 | 4.788 | 27.617 | 0.002 |
| mmu-miR-16 | <0.0001 | 3.32 | 9.987 | 0.002 |
| mmu-miR-291b-5p | <0.0001 | −4.975 | −31.45 | 0.002 |
| mmu-miR-222 | <0.0001 | 3.593 | 12.063 | 0.002 |
| mmu-miR-1 | 0.001 | 5.798 | 55.619 | 0.003 |
| mmu-miR-320 | 0.001 | 4.708 | 26.128 | 0.003 |
| mmu-miR-145 | 0.001 | 3.14 | 8.815 | 0.004 |
| mmu-miR-27b | 0.001 | 3.368 | 10.321 | 0.004 |
| mmu-miR-191 | 0.001 | 3.275 | 9.68 | 0.004 |
| mmu-miR-93 | 0.001 | 4.613 | 24.463 | 0.004 |
| mmu-miR-128 | 0.001 | 3.29 | 9.781 | 0.005 |
| mmu-miR-146a | 0.001 | 4.66 | 25.281 | 0.005 |
| mmu-miR-298 | 0.001 | 4.085 | 16.971 | 0.005 |
| mmu-miR-200a | 0.001 | 4.88 | 29.446 | 0.005 |
| mmu-let-7d* | 0.001 | 3.365 | 10.303 | 0.005 |
| mmu-miR-342-3p | 0.002 | 4.775 | 27.379 | 0.006 |
| mmu-miR-199a-3p | 0.002 | 4.063 | 16.708 | 0.007 |
| mmu-miR-197 | 0.002 | 3.413 | 10.648 | 0.007 |
| mmu-miR-186 | 0.002 | 4.88 | 29.446 | 0.007 |
| mmu-miR-1196 | 0.002 | 2.538 | 5.806 | 0.007 |
| mmu-miR-142-5p | 0.003 | −2.678 | −6.397 | 0.01 |
| mmu-miR-130b | 0.003 | 4.528 | 23.063 | 0.01 |
| mmu-let-7b | 0.003 | 3.515 | 11.432 | 0.011 |
| mmu-miR-297a | 0.003 | 4.095 | 17.089 | 0.012 |
| mmu-miR-32 | 0.004 | 3.903 | 14.954 | 0.013 |
| mmu-miR-214 | 0.004 | 3.253 | 9.53 | 0.013 |
| mmu-miR-324-3p | 0.004 | 6.188 | 72.882 | 0.014 |
| mmu-miR-346 | 0.004 | 5.025 | 32.559 | 0.014 |
| mmu-miR-152 | 0.005 | 2.738 | 6.669 | 0.015 |
| mmu-miR-33 | 0.005 | 3.585 | 12 | 0.016 |
| mmu-miR-1952 | 0.005 | 3.058 | 8.325 | 0.016 |
| mmu-miR-196a | 0.005 | −3.763 | −13.571 | 0.016 |
| mmu-miR-181b | 0.005 | 5.09 | 34.06 | 0.017 |
| mmu-let-7d | 0.006 | 5.99 | 63.558 | 0.017 |
| mmu-miR-872* | 0.007 | 4.478 | 22.277 | 0.02 |
| mmu-miR-30e* | 0.007 | 4.493 | 22.51 | 0.02 |
| mmu-miR-194 | 0.007 | 4.13 | 17.509 | 0.021 |
| mmu-miR-187 | 0.008 | 6.115 | 69.31 | 0.022 |
| mmu-miR-221 | 0.008 | 2.783 | 6.88 | 0.022 |
| mmu-miR-155 | 0.008 | 2.848 | 7.198 | 0.023 |
| mmu-miR-99b | 0.008 | 2.413 | 5.324 | 0.023 |
| mmu-miR-34a | 0.01 | −2.423 | −5.361 | 0.027 |
| mmu-miR-302c | 0.011 | 2.865 | 7.285 | 0.029 |
| mmu-miR-301b | 0.012 | 3.925 | 15.189 | 0.031 |
| mmu-miR-183* | 0.013 | 5.19 | 36.504 | 0.033 |
| mmu-miR-130b* | 0.015 | 2.213 | 4.635 | 0.036 |
| mmu-miR-139-5p | 0.016 | 3.123 | 8.709 | 0.039 |
| mmu-miR-30e | 0.016 | −3.143 | −8.831 | 0.039 |
| mmu-miR-1983 | 0.018 | 3.385 | 10.447 | 0.043 |
| mmu-miR-345-5p | 0.023 | 3.618 | 12.274 | 0.052 |
| mmu-miR-135a* | 0.023 | 4.153 | 17.784 | 0.052 |

TABLE 7-continued

Serum exosomal miRNA signatures after fat transplantation

| miRNA | | | | |
|---|---|---|---|---|
| mmu-miR-669m | 0.023 | 3.113 | 8.649 | 0.053 |
| mmu-miR-139-3p | 0.025 | 2.633 | 6.201 | 0.055 |
| mmu-miR-337-3p | 0.027 | 3.273 | 9.663 | 0.059 |
| mmu-miR-324-5p | 0.027 | 2.708 | 6.532 | 0.06 |
| mmu-miR-107 | 0.027 | 2.178 | 4.524 | 0.06 |
| mmu-miR-296-3p | 0.031 | 2.405 | 5.296 | 0.067 |
| mmu-miR-467e* | 0.033 | 2.838 | 7.148 | 0.071 |
| mmu-miR-199b | 0.033 | 2.68 | 6.409 | 0.071 |
| mmu-miR-493 | 0.035 | 1.74 | 3.34 | 0.073 |
| mmu-miR-1954 | 0.036 | 2 | 4 | 0.074 |
| mmu-miR-760 | 0.037 | 2.528 | 5.766 | 0.077 |
| mmu-miR-210 | 0.037 | 3.443 | 10.872 | 0.077 |
| mmu-miR-29c | 0.038 | 2.983 | 7.904 | 0.078 |
| mmu-miR-203 | 0.041 | −1.858 | −3.624 | 0.084 |
| mmu-miR-15b | 0.042 | 1.738 | 3.335 | 0.084 |
| mmu-miR-103 | 0.042 | 1.703 | 3.255 | 0.084 |
| mmu-miR-879* | 0.044 | 2.723 | 6.6 | 0.087 |
| mmu-miR-339-5p | 0.044 | 2.683 | 6.42 | 0.087 |

| miRNA | EPIvsSAL p-value | EPIvsSAL logFC | EPIvsSAL FC | EPIvsSAL FDR |
|---|---|---|---|---|
| mmu-miR-22 | <0.0001 | 11.77 | 3492.393 | <0.0001 |
| mmu-miR-19b | <0.0001 | 12.65 | 6427.313 | <0.0001 |
| mmu-miR-19a | <0.0001 | 12.458 | 5624.464 | <0.0001 |
| mmu-miR-92b | <0.0001 | 9.335 | 645.825 | <0.0001 |
| mmu-miR-323-5p | <0.0001 | 10.398 | 1348.837 | <0.0001 |
| mmu-miR-193b | <0.0001 | 8.545 | 373.509 | <0.0001 |
| mmu-miR-133b | <0.0001 | 11.94 | 3929.146 | <0.0001 |
| mmu-let-7a | <0.0001 | 8.838 | 457.459 | <0.0001 |
| mmu-miR-207 | <0.0001 | 7.813 | 224.8 | <0.0001 |
| mmu-miR-291a-5p | <0.0001 | 9.528 | 738.012 | <0.0001 |
| mmu-miR-185 | <0.0001 | 8.455 | 350.92 | <0.0001 |
| mmu-miR-15a | <0.0001 | 7.838 | 228.73 | <0.0001 |
| mmu-miR-92a | <0.0001 | 7.528 | 184.503 | <0.0001 |
| mmu-miR-326 | <0.0001 | 10.503 | 1450.666 | <0.0001 |
| mmu-miR-25 | <0.0001 | 6.693 | 103.429 | <0.0001 |
| mmu-miR-125a-3p | <0.0001 | 9.81 | 897.644 | <0.0001 |
| mmu-miR-212 | <0.0001 | 8.663 | 405.203 | <0.0001 |
| mmu-miR-328 | <0.0001 | 10.788 | 1767.507 | <0.0001 |
| mmu-miR-127* | <0.0001 | 7.935 | 244.722 | <0.0001 |
| mmu-let-7c | <0.0001 | 5.385 | 41.788 | <0.0001 |
| mmu-miR-145 | <0.0001 | 5.928 | 60.863 | <0.0001 |
| mmu-let-7e | <0.0001 | 6.23 | 75.061 | <0.0001 |
| mmu-miR-302c | <0.0001 | 7.583 | 191.673 | <0.0001 |
| mmu-miR-706 | <0.0001 | 8.04 | 263.197 | <0.0001 |
| mmu-miR-29a | <0.0001 | 9.32 | 639.145 | <0.0001 |
| mmu-miR-204 | <0.0001 | 6.178 | 72.379 | <0.0001 |
| mmu-miR-199a-5p | <0.0001 | 5.448 | 43.638 | <0.0001 |
| mmu-miR-20a | <0.0001 | 8.748 | 429.794 | <0.0001 |
| mmu-miR-24 | <0.0001 | 5.415 | 42.666 | <0.0001 |
| mmu-miR-133a | <0.0001 | 8.955 | 496.276 | <0.0001 |
| mmu-miR-222 | <0.0001 | 5.745 | 53.631 | <0.0001 |
| mmu-miR-129-5p | <0.0001 | 6.663 | 101.301 | <0.0001 |
| mmu-miR-297a | <0.0001 | 8.133 | 280.625 | <0.0001 |
| mmu-miR-188-3p | <0.0001 | 5.545 | 46.689 | <0.0001 |
| mmu-miR-100 | <0.0001 | 7.02 | 129.787 | <0.0001 |
| mmu-miR-101a | <0.0001 | 6.763 | 108.571 | <0.0001 |
| mmu-miR-205 | <0.0001 | 5.593 | 48.251 | <0.0001 |
| mmu-miR-214 | <0.0001 | 6.425 | 85.925 | <0.0001 |
| mmu-miR-27a | <0.0001 | 5.635 | 49.694 | <0.0001 |
| mmu-miR-195 | <0.0001 | 5.048 | 33.071 | <0.0001 |
| mmu-miR-335-3p | <0.0001 | 6.485 | 89.573 | <0.0001 |
| mmu-miR-106a | <0.0001 | 8.263 | 307.086 | <0.0001 |
| mmu-miR-16 | <0.0001 | 4.778 | 27.427 | <0.0001 |
| mmu-miR-93 | <0.0001 | 7.25 | 152.219 | <0.0001 |
| mmu-miR-188-5p | <0.0001 | 6.01 | 64.445 | <0.0001 |
| mmu-miR-20b | <0.0001 | 5.775 | 54.758 | <0.0001 |
| mmu-miR-148b | <0.0001 | 6.29 | 78.249 | <0.0001 |
| mmu-miR-148a | <0.0001 | 4.905 | 29.961 | <0.0001 |
| mmu-miR-128 | <0.0001 | 5.03 | 32.672 | <0.0001 |
| mmu-miR-99a | <0.0001 | 4.945 | 30.803 | <0.0001 |
| mmu-miR-493 | <0.0001 | 4.478 | 22.277 | <0.0001 |
| mmu-miR-146a | <0.0001 | 7.005 | 128.444 | <0.0001 |
| mmu-miR-181d | <0.0001 | 6.085 | 67.884 | <0.0001 |
| mmu-miR-197 | <0.0001 | 5.325 | 40.085 | <0.0001 |
| mmu-miR-191 | <0.0001 | 4.685 | 25.723 | <0.0001 |
| mmu-miR-130a | <0.0001 | 5.968 | 62.574 | <0.0001 |

TABLE 7-continued

Serum exosomal miRNA signatures after fat transplantation

| | | | | |
|---|---|---|---|---|
| mmu-miR-30d | <0.0001 | 4.318 | 19.939 | <0.0001 |
| mmu-miR-30b | <0.0001 | 6.72 | 105.42 | <0.0001 |
| mmu-miR-129-3p | <0.0001 | 7.378 | 166.283 | <0.0001 |
| mmu-miR-125b-5p | <0.0001 | 5.153 | 35.568 | <0.0001 |
| mmu-miR-338-5p | <0.0001 | 6.528 | 92.251 | <0.0001 |
| mmu-miR-31* | <0.0001 | 5.915 | 60.338 | <0.0001 |
| mmu-miR-139-5p | <0.0001 | 6.245 | 75.846 | <0.0001 |
| mmu-miR-200a | <0.0001 | 6.36 | 82.139 | 0.001 |
| mmu-miR-467e* | <0.0001 | 5.99 | 63.558 | 0.001 |
| mmu-miR-221 | <0.0001 | 4.498 | 22.588 | 0.001 |
| mmu-miR-127 | <0.0001 | 6.835 | 114.167 | 0.001 |
| mmu-miR-1943 | <0.0001 | 5.318 | 39.877 | 0.001 |
| mmu-miR-1955 | <0.0001 | 5.18 | 36.252 | 0.001 |
| mmu-miR-149 | <0.0001 | 5.888 | 59.199 | 0.001 |
| mmu-miR-320 | <0.0001 | 5.31 | 39.671 | 0.001 |
| mmu-miR-130b* | <0.0001 | 3.748 | 13.431 | 0.001 |
| mmu-miR-669i | <0.0001 | 6.415 | 85.331 | 0.001 |
| mmu-miR-324-5p | <0.0001 | 5.115 | 34.655 | 0.001 |
| mmu-miR-199a-3p | <0.0001 | 5.018 | 32.391 | 0.001 |
| mmu-miR-1952 | <0.0001 | 4.27 | 19.293 | 0.002 |
| mmu-miR-298 | <0.0001 | 4.69 | 25.813 | 0.002 |
| mmu-let-7d | <0.0001 | 8.373 | 331.416 | 0.002 |
| mmu-miR-29c | <0.0001 | 5.86 | 58.081 | 0.002 |
| mmu-miR-770-3p | <0.0001 | 4.405 | 21.185 | 0.002 |
| mmu-miR-339-5p | 0.001 | 5.32 | 39.947 | 0.002 |
| mmu-miR-760 | 0.001 | 4.813 | 28.1 | 0.002 |
| mmu-miR-300 | 0.001 | 7.098 | 136.949 | 0.002 |
| mmu-miR-2140 | 0.001 | 3.013 | 8.07 | 0.003 |
| mmu-miR-1898 | 0.001 | 3.993 | 15.917 | 0.003 |
| mmu-miR-301a | 0.001 | 5.228 | 37.466 | 0.003 |
| mmu-miR-18a | 0.001 | 4.95 | 30.91 | 0.003 |
| mmu-miR-346 | 0.001 | 6.08 | 67.649 | 0.004 |
| mmu-miR-10a | 0.001 | 3.378 | 10.393 | 0.004 |
| mmu-miR-183 | 0.001 | 5.685 | 51.446 | 0.004 |
| mmu-let-7d* | 0.001 | 3.443 | 10.872 | 0.004 |
| mmu-let-7g | 0.001 | 5.295 | 39.26 | 0.005 |
| mmu-miR-324-3p | 0.001 | 7.163 | 143.261 | 0.005 |
| mmu-miR-1196 | 0.001 | 2.668 | 6.353 | 0.005 |
| mmu-miR-1197 | 0.001 | 3.018 | 8.098 | 0.005 |
| mmu-miR-342-3p | 0.002 | 4.708 | 26.128 | 0.006 |
| mmu-miR-1899 | 0.002 | 3.015 | 8.084 | 0.007 |
| mmu-miR-92a* | 0.003 | 5.445 | 43.562 | 0.008 |
| mmu-miR-1 | 0.003 | 4.9 | 29.857 | 0.008 |
| mmu-miR-21 | 0.003 | 2.675 | 6.386 | 0.008 |
| mmu-miR-345-5p | 0.003 | 5.078 | 33.766 | 0.008 |
| mmu-miR-15b | 0.003 | 2.773 | 6.833 | 0.009 |
| mmu-miR-187 | 0.003 | 7.09 | 136.239 | 0.009 |
| mmu-miR-1954 | 0.003 | 3.053 | 8.296 | 0.009 |
| mmu-miR-1983 | 0.003 | 4.488 | 22.432 | 0.009 |
| mmu-miR-181b | 0.003 | 5.498 | 45.176 | 0.009 |
| mmu-miR-27b | 0.003 | 2.86 | 7.26 | 0.009 |
| mmu-let-7b | 0.004 | 3.45 | 10.928 | 0.01 |
| mmu-miR-218 | 0.004 | 4.868 | 29.192 | 0.01 |
| mmu-miR-540-3p | 0.004 | 3.615 | 12.252 | 0.012 |
| mmu-miR-199b | 0.004 | 3.808 | 14.001 | 0.012 |
| mmu-miR-30e* | 0.005 | 4.77 | 27.284 | 0.012 |
| mmu-miR-124 | 0.005 | 4.523 | 22.983 | 0.014 |
| mmu-miR-10b | 0.006 | 4.47 | 22.162 | 0.015 |
| mmu-miR-183* | 0.006 | 5.888 | 59.199 | 0.015 |
| mmu-miR-350 | 0.007 | 5.968 | 62.574 | 0.016 |
| mmu-miR-186 | 0.007 | 4.108 | 17.238 | 0.017 |
| mmu-miR-876-3p | 0.007 | 2.368 | 5.16 | 0.017 |
| mmu-miR-296-3p | 0.007 | 3.12 | 8.694 | 0.017 |
| mmu-miR-99b | 0.008 | 2.428 | 5.38 | 0.019 |
| mmu-miR-125b-3p | 0.008 | 3.62 | 12.295 | 0.019 |
| mmu-miR-711 | 0.009 | 4.868 | 29.192 | 0.02 |
| mmu-miR-196a* | 0.009 | 3.658 | 12.619 | 0.02 |
| mmu-miR-103 | 0.009 | 2.295 | 4.908 | 0.02 |
| mmu-miR-194 | 0.009 | 3.985 | 15.835 | 0.02 |
| mmu-miR-99b* | 0.009 | 1.99 | 3.972 | 0.02 |
| mmu-miR-879* | 0.009 | 3.67 | 12.729 | 0.021 |
| mmu-miR-101b | 0.011 | 4.063 | 16.708 | 0.024 |
| mmu-miR-7a | 0.012 | 2.803 | 6.976 | 0.025 |
| mmu-miR-130b | 0.013 | 3.613 | 12.231 | 0.027 |
| mmu-miR-872* | 0.014 | 3.998 | 15.972 | 0.028 |
| mmu-miR-670 | 0.014 | 3.153 | 8.892 | 0.028 |
| mmu-miR-151-3p | 0.016 | 2.328 | 5.019 | 0.032 |
| mmu-miR-134 | 0.016 | 3.178 | 9.047 | 0.032 |

TABLE 7-continued

Serum exosomal miRNA signatures after fat transplantation

| miRNA | | | | |
|---|---|---|---|---|
| mmu-miR-181a | 0.017 | 4.553 | 23.466 | 0.033 |
| mmu-miR-151-5p | 0.017 | 3.725 | 13.223 | 0.033 |
| mmu-miR-1895 | 0.018 | 3.165 | 8.969 | 0.035 |
| mmu-miR-140 | 0.018 | 3.035 | 8.196 | 0.035 |
| mmu-miR-2133 | 0.019 | 1.713 | 3.277 | 0.037 |
| mmu-miR-135a* | 0.02 | 4.258 | 19.126 | 0.038 |
| mmu-miR-139-3p | 0.024 | 2.658 | 6.309 | 0.044 |
| mmu-miR-669m | 0.024 | 3.083 | 8.471 | 0.045 |
| mmu-miR-155 | 0.029 | 2.26 | 4.79 | 0.053 |
| mmu-miR-152 | 0.031 | 1.978 | 3.938 | 0.056 |
| mmu-miR-32 | 0.04 | 2.583 | 5.99 | 0.07 |
| mmu-miR-296-5p | 0.042 | 3.133 | 8.77 | 0.072 |
| mmu-miR-126-5p | 0.045 | 1.695 | 3.238 | 0.076 |

| miRNA | BATvsSAL p-value | BATvsSAL logFC | BATvsSAL FC | BATvsSAL FDR |
|---|---|---|---|---|
| mmu-miR-22 | <0.0001 | 13.274 | 9906.548 | <0.0001 |
| mmu-miR-19b | <0.0001 | 15.088 | 34816.897 | <0.0001 |
| mmu-miR-19a | <0.0001 | 15.021 | 33244.622 | <0.0001 |
| mmu-miR-323-5p | <0.0001 | 11.954 | 3967.918 | <0.0001 |
| mmu-let-7a | <0.0001 | 11.794 | 3551.387 | <0.0001 |
| mmu-miR-128 | <0.0001 | 11.455 | 2807.363 | <0.0001 |
| mmu-miR-15a | <0.0001 | 11.421 | 2741.659 | <0.0001 |
| mmu-miR-92b | <0.0001 | 9.158 | 571.061 | <0.0001 |
| mmu-miR-103 | <0.0001 | 9.771 | 873.603 | <0.0001 |
| mmu-let-7e | <0.0001 | 10.161 | 1144.763 | <0.0001 |
| mmu-miR-133b | <0.0001 | 12.843 | 7349.006 | <0.0001 |
| mmu-miR-193b | <0.0001 | 8.048 | 264.569 | <0.0001 |
| mmu-miR-291a-5p | <0.0001 | 10.695 | 1657.738 | <0.0001 |
| mmu-miR-207 | <0.0001 | 8.254 | 305.318 | <0.0001 |
| mmu-miR-185 | <0.0001 | 9.101 | 549.065 | <0.0001 |
| mmu-let-7c | <0.0001 | 7.533 | 185.143 | <0.0001 |
| mmu-miR-195 | <0.0001 | 8.286 | 312.093 | <0.0001 |
| mmu-miR-21 | <0.0001 | 7.794 | 221.962 | <0.0001 |
| mmu-miR-27a | <0.0001 | 8.921 | 484.661 | <0.0001 |
| mmu-miR-25 | <0.0001 | 8.173 | 288.681 | <0.0001 |
| mmu-miR-16 | <0.0001 | 7.592 | 192.894 | <0.0001 |
| mmu-miR-24 | <0.0001 | 7.529 | 184.716 | <0.0001 |
| mmu-miR-212 | <0.0001 | 10.267 | 1231.898 | <0.0001 |
| mmu-miR-145 | <0.0001 | 7.298 | 157.314 | <0.0001 |
| mmu-miR-205 | <0.0001 | 7.888 | 236.796 | <0.0001 |
| mmu-miR-204 | <0.0001 | 8.111 | 276.442 | <0.0001 |
| mmu-miR-20b | <0.0001 | 8.658 | 403.801 | <0.0001 |
| mmu-miR-130a | <0.0001 | 9.748 | 860.084 | <0.0001 |
| mmu-miR-188-3p | <0.0001 | 7.549 | 187.295 | <0.0001 |
| mmu-miR-181d | <0.0001 | 9.562 | 755.698 | <0.0001 |
| mmu-miR-148a | <0.0001 | 7.147 | 141.697 | <0.0001 |
| mmu-miR-29a | <0.0001 | 11.388 | 2680.587 | <0.0001 |
| mmu-miR-199a-5p | <0.0001 | 6.828 | 113.575 | <0.0001 |
| mmu-miR-92a | <0.0001 | 7.473 | 177.704 | <0.0001 |
| mmu-miR-20a | <0.0001 | 10.758 | 1732.132 | <0.0001 |
| mmu-miR-197 | <0.0001 | 8.081 | 270.753 | <0.0001 |
| mmu-miR-302c | <0.0001 | 8.544 | 373.294 | <0.0001 |
| mmu-miR-335-3p | <0.0001 | 8.623 | 394.122 | <0.0001 |
| mmu-miR-222 | <0.0001 | 7.038 | 131.447 | <0.0001 |
| mmu-miR-148b | <0.0001 | 8.584 | 383.788 | <0.0001 |
| mmu-miR-328 | <0.0001 | 11.182 | 2322.828 | <0.0001 |
| mmu-miR-1 | <0.0001 | 11.521 | 2938.437 | <0.0001 |
| mmu-miR-29c | <0.0001 | 11.071 | 2151.062 | <0.0001 |
| mmu-miR-17 | <0.0001 | 6.815 | 112.595 | <0.0001 |
| mmu-miR-214 | <0.0001 | 7.918 | 241.771 | <0.0001 |
| mmu-miR-146a | <0.0001 | 9.69 | 826.001 | <0.0001 |
| mmu-miR-133a | <0.0001 | 10.186 | 1164.773 | <0.0001 |
| mmu-miR-324-5p | <0.0001 | 9.038 | 525.787 | <0.0001 |
| mmu-miR-338-5p | <0.0001 | 9.653 | 804.808 | <0.0001 |
| mmu-miR-30d | <0.0001 | 6.135 | 70.278 | <0.0001 |
| mmu-miR-298 | <0.0001 | 8.434 | 345.889 | <0.0001 |
| mmu-miR-99a | <0.0001 | 6.603 | 97.174 | <0.0001 |
| mmu-miR-7a | <0.0001 | 7.931 | 244.016 | <0.0001 |
| mmu-miR-106a | <0.0001 | 10.274 | 1238.318 | <0.0001 |
| mmu-miR-297a | <0.0001 | 9.375 | 663.982 | <0.0001 |
| mmu-miR-10a | <0.0001 | 6.413 | 85.233 | <0.0001 |
| mmu-miR-142-5p | <0.0001 | 5.774 | 54.726 | <0.0001 |
| mmu-miR-100 | <0.0001 | 7.826 | 226.888 | <0.0001 |
| mmu-miR-93 | <0.0001 | 8.618 | 392.986 | <0.0001 |
| mmu-miR-34a | <0.0001 | 6.109 | 69.031 | <0.0001 |
| mmu-miR-140 | <0.0001 | 8.304 | 316.085 | <0.0001 |

TABLE 7-continued

Serum exosomal miRNA signatures after fat transplantation

| | | | | |
|---|---|---|---|---|
| mmu-let-7g | <0.0001 | 9.813 | 899.721 | <0.0001 |
| mmu-miR-200a | <0.0001 | 8.973 | 502.623 | <0.0001 |
| mmu-miR-326 | <0.0001 | 8.408 | 339.555 | <0.0001 |
| mmu-miR-30b | <0.0001 | 8.485 | 358.294 | <0.0001 |
| mmu-miR-107 | <0.0001 | 6.358 | 81.997 | <0.0001 |
| mmu-miR-199a-3p | <0.0001 | 7.763 | 217.268 | <0.0001 |
| mmu-miR-26b | <0.0001 | 7.598 | 193.788 | <0.0001 |
| mmu-miR-188-5p | <0.0001 | 6.634 | 99.331 | <0.0001 |
| mmu-miR-129-5p | <0.0001 | 6.694 | 103.549 | <0.0001 |
| mmu-miR-101a | <0.0001 | 6.884 | 118.125 | <0.0001 |
| mmu-miR-191 | <0.0001 | 5.567 | 47.395 | <0.0001 |
| mmu-miR-200b | <0.0001 | 7.264 | 153.721 | <0.0001 |
| mmu-miR-1196 | <0.0001 | 4.703 | 26.037 | <0.0001 |
| mmu-miR-127* | <0.0001 | 6.961 | 124.572 | <0.0001 |
| mmu-miR-706 | <0.0001 | 7.318 | 159.51 | <0.0001 |
| mmu-miR-320 | <0.0001 | 7.673 | 204.128 | <0.0001 |
| mmu-miR-27b | <0.0001 | 5.569 | 47.477 | <0.0001 |
| mmu-miR-101b | <0.0001 | 9.525 | 736.734 | <0.0001 |
| mmu-miR-125a-3p | <0.0001 | 7.918 | 241.771 | <0.0001 |
| mmu-miR-186 | <0.0001 | 8.834 | 456.404 | <0.0001 |
| mmu-miR-15b | <0.0001 | 5.223 | 37.336 | <0.0001 |
| mmu-let-7d* | <0.0001 | 5.611 | 48.869 | <0.0001 |
| mmu-miR-301a | <0.0001 | 8.194 | 292.88 | <0.0001 |
| mmu-miR-221 | <0.0001 | 5.881 | 58.926 | <0.0001 |
| mmu-miR-770-3p | <0.0001 | 6.421 | 85.677 | <0.0001 |
| mmu-miR-30e | <0.0001 | 7.247 | 151.867 | <0.0001 |
| mmu-miR-125b-5p | <0.0001 | 5.652 | 50.271 | <0.0001 |
| mmu-miR-493 | <0.0001 | 4.44 | 21.706 | <0.0001 |
| mmu-let-7b | <0.0001 | 5.842 | 57.348 | <0.0001 |
| mmu-miR-18a | <0.0001 | 6.978 | 126.019 | <0.0001 |
| mmu-miR-1955 | <0.0001 | 6.139 | 70.481 | <0.0001 |
| mmu-miR-139-5p | <0.0001 | 6.641 | 99.791 | <0.0001 |
| mmu-miR-26a | <0.0001 | 8.317 | 318.835 | <0.0001 |
| mmu-miR-199b | <0.0001 | 6.445 | 87.124 | <0.0001 |
| mmu-miR-1943 | <0.0001 | 6.078 | 67.532 | <0.0001 |
| mmu-miR-130b | <0.0001 | 7.069 | 134.286 | <0.0001 |
| mmu-miR-1952 | <0.0001 | 5.07 | 33.591 | 0.001 |
| mmu-miR-31* | <0.0001 | 5.857 | 57.947 | 0.001 |
| mmu-miR-196a* | <0.0001 | 6.479 | 89.212 | 0.001 |
| mmu-miR-296-3p | <0.0001 | 5.335 | 40.364 | 0.001 |
| mmu-miR-134 | <0.0001 | 6.132 | 70.116 | 0.001 |
| mmu-miR-32 | <0.0001 | 5.974 | 62.864 | 0.001 |
| mmu-miR-339-5p | <0.0001 | 6.295 | 78.521 | 0.001 |
| mmu-miR-598 | <0.0001 | 5.288 | 39.057 | 0.001 |
| mmu-miR-155 | <0.0001 | 4.754 | 26.987 | 0.001 |
| mmu-miR-346 | <0.0001 | 7.599 | 193.9 | 0.001 |
| mmu-miR-126-5p | <0.0001 | 3.887 | 14.791 | 0.001 |
| mmu-miR-194 | <0.0001 | 6.648 | 100.311 | 0.001 |
| mmu-miR-125b-3p | <0.0001 | 5.938 | 61.287 | 0.001 |
| mmu-miR-10b | <0.0001 | 6.892 | 118.74 | 0.001 |
| mmu-miR-149 | <0.0001 | 5.916 | 60.373 | 0.001 |
| mmu-miR-342-3p | <0.0001 | 6.065 | 66.949 | 0.001 |
| mmu-miR-99b | <0.0001 | 3.806 | 13.985 | 0.001 |
| mmu-let-7d | <0.0001 | 8.853 | 462.241 | 0.001 |
| mmu-miR-152 | <0.0001 | 3.953 | 15.491 | 0.001 |
| mmu-miR-184 | <0.0001 | 3.333 | 10.074 | 0.001 |
| mmu-miR-760 | 0.001 | 5.18 | 36.252 | 0.002 |
| mmu-miR-99b* | 0.001 | 3.09 | 8.515 | 0.002 |
| mmu-miR-139-3p | 0.001 | 4.877 | 29.378 | 0.002 |
| mmu-miR-146b | 0.001 | 6.663 | 101.359 | 0.002 |
| mmu-miR-30e* | 0.001 | 6.587 | 96.113 | 0.002 |
| mmu-miR-127 | 0.001 | 6.338 | 80.868 | 0.002 |
| mmu-miR-151-3p | 0.001 | 3.898 | 14.911 | 0.002 |
| mmu-miR-876-3p | 0.001 | 3.425 | 10.741 | 0.002 |
| mmu-miR-1954 | 0.001 | 3.881 | 14.732 | 0.002 |
| mmu-miR-1899 | 0.001 | 3.604 | 12.161 | 0.002 |
| mmu-miR-300 | 0.001 | 7.338 | 161.736 | 0.002 |
| mmu-miR-1197 | 0.001 | 3.396 | 10.526 | 0.003 |
| mmu-miR-33 | 0.001 | 4.741 | 26.738 | 0.003 |
| mmu-miR-540-3p | 0.001 | 4.624 | 24.661 | 0.003 |
| mmu-miR-324-3p | 0.001 | 7.791 | 221.449 | 0.003 |
| mmu-miR-1983 | 0.001 | 5.331 | 40.248 | 0.004 |
| mmu-miR-669i | 0.002 | 5.702 | 52.044 | 0.004 |
| mmu-miR-203 | 0.002 | 3.435 | 10.815 | 0.004 |
| mmu-miR-350 | 0.002 | 7.798 | 222.604 | 0.004 |
| mmu-miR-150 | 0.002 | 5.986 | 63.375 | 0.006 |
| mmu-miR-511 | 0.002 | 5.363 | 41.165 | 0.006 |
| mmu-miR-196a | 0.003 | 4.386 | 20.906 | 0.007 |

TABLE 7-continued

Serum exosomal miRNA signatures after fat transplantation

| | | | | |
|---|---|---|---|---|
| mmu-miR-467e* | 0.003 | 4.537 | 23.21 | 0.008 |
| mmu-miR-92a* | 0.004 | 5.572 | 47.56 | 0.009 |
| mmu-miR-497 | 0.004 | 4.121 | 17.398 | 0.01 |
| mmu-miR-879* | 0.004 | 4.496 | 22.562 | 0.01 |
| mmu-miR-151-5p | 0.004 | 5.022 | 32.484 | 0.01 |
| mmu-miR-130b* | 0.004 | 2.903 | 7.482 | 0.01 |
| mmu-miR-301b | 0.005 | 4.893 | 29.702 | 0.011 |
| mmu-miR-183 | 0.005 | 4.991 | 31.797 | 0.011 |
| mmu-miR-129-3p | 0.005 | 4.658 | 25.238 | 0.011 |
| mmu-miR-711 | 0.006 | 5.613 | 48.953 | 0.012 |
| mmu-miR-670 | 0.006 | 3.921 | 15.146 | 0.012 |
| mmu-miR-872* | 0.006 | 4.961 | 31.143 | 0.012 |
| mmu-miR-669m | 0.007 | 4.141 | 17.641 | 0.015 |
| mmu-miR-218 | 0.008 | 4.682 | 25.664 | 0.017 |
| mmu-miR-1895 | 0.009 | 3.852 | 14.437 | 0.018 |
| mmu-miR-181a | 0.009 | 5.473 | 44.4 | 0.018 |
| mmu-miR-322 | 0.009 | 4.448 | 21.819 | 0.019 |
| mmu-miR-296-5p | 0.011 | 4.414 | 21.32 | 0.022 |
| mmu-miR-1898 | 0.011 | 2.952 | 7.736 | 0.022 |
| mmu-miR-345-5p | 0.012 | 4.375 | 20.749 | 0.024 |
| mmu-miR-135a* | 0.013 | 4.998 | 31.945 | 0.025 |
| mmu-miR-2133 | 0.013 | 1.968 | 3.911 | 0.026 |
| mmu-miR-210 | 0.014 | 4.519 | 22.93 | 0.026 |
| mmu-miR-20b* | 0.017 | 2.751 | 6.731 | 0.031 |
| mmu-miR-2140 | 0.033 | 1.807 | 3.498 | 0.056 |
| mmu-miR-187 | 0.043 | 4.797 | 27.793 | 0.071 |
| mmu-miR-183* | 0.049 | 4.261 | 19.171 | 0.079 |

FDR = false discovery rate, "*" indicates star species miRNA, in which the 3'-5' fragment induces the repression.

Indeed, of the 177 exosomal miRNAs that were detectable in wild-type and significantly decreased in ADicerKO serum, fat transplantation restored the levels of the majority of these at least 50% of the way to normal indicating that adipose tissue is a major source of circulating exosomal miRNAs and that different depots contribute differentially to circulating miRNAs, with BAT being the dominant depot.

Figure 2D:
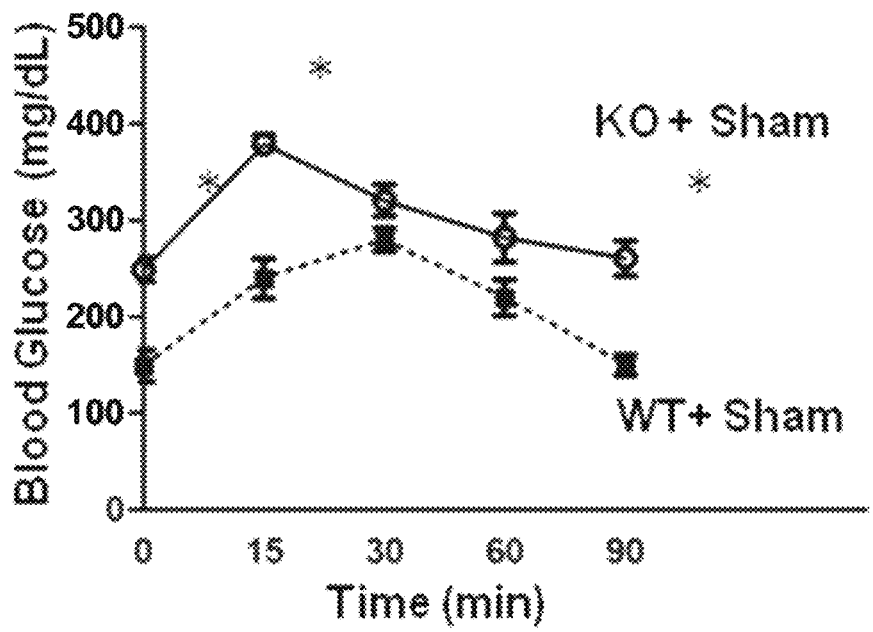
Figure 2E:
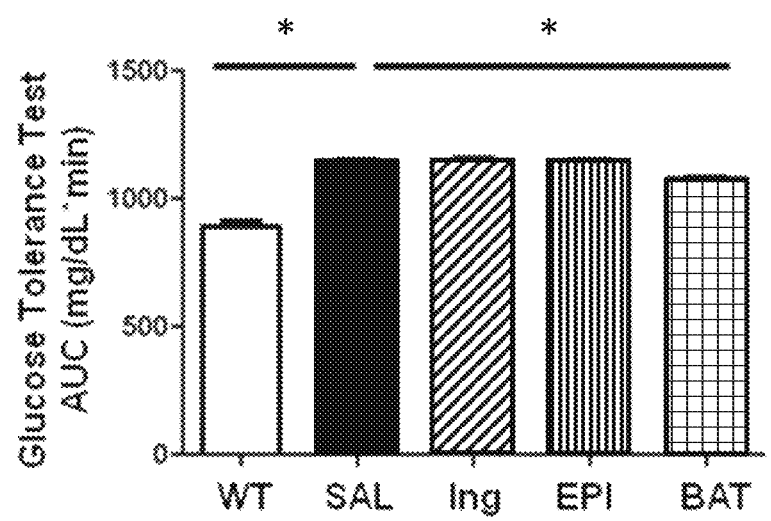
Figures 7E, 8A:
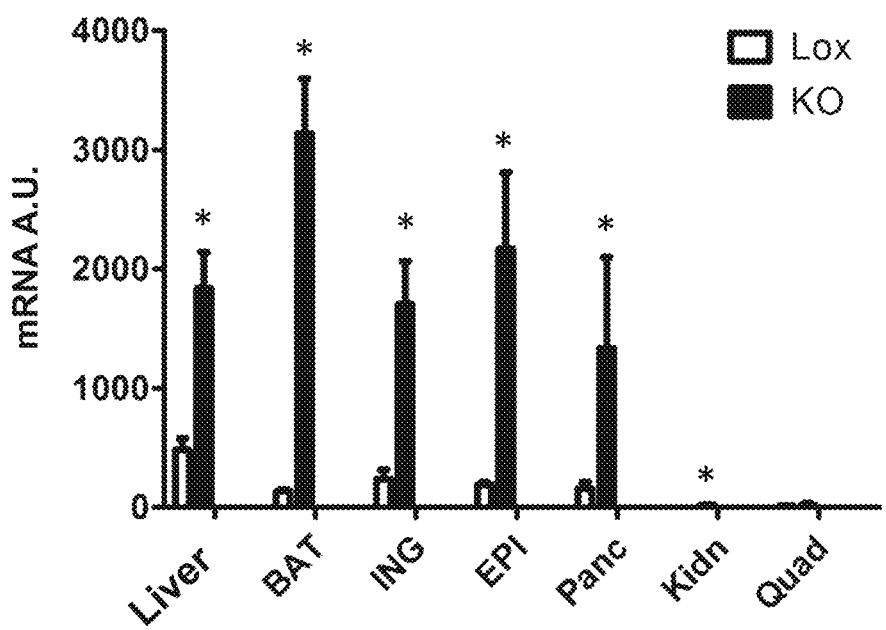

Physiologically, ADicerKO mice had markedly impaired glucose tolerance tests (GTTs) compared to controls with about a 50% increase in area under the curve (FIGS. 2d and 2e). This did not significantly change after sham surgery and showed only small, non-significant changes after transplantation of Ing-WAT or Epi-WAT. However, GTT results were significantly improved in the ADicerKO mice that had received a BAT transplant (FIG. 2e). ADicerKO mice also exhibit marked insulin resistance, as indicated by increased circulating insulin levels; this was also reduced in the group receiving the BAT transplant, but did not quite reach statistical significance (FIG. 7e). Serum interleukin 6 (IL-6), leptin and adiponectin levels were all lower in ADicerKO compared to control and were not restored by transplantation (FIG. 7e).

These data support the conclusion that BAT transplant into ADicerKO mice improved the metabolic parameters of these mice. BAT and Ing-WAT transplants also showed remarkable restoration of circulating exosomal miRNAs in ADicerKO mice. In addition, ADicerKO mice receiving a BAT transplant had reduced circulating and hepatic FGF21 levels.

Figure 3A:
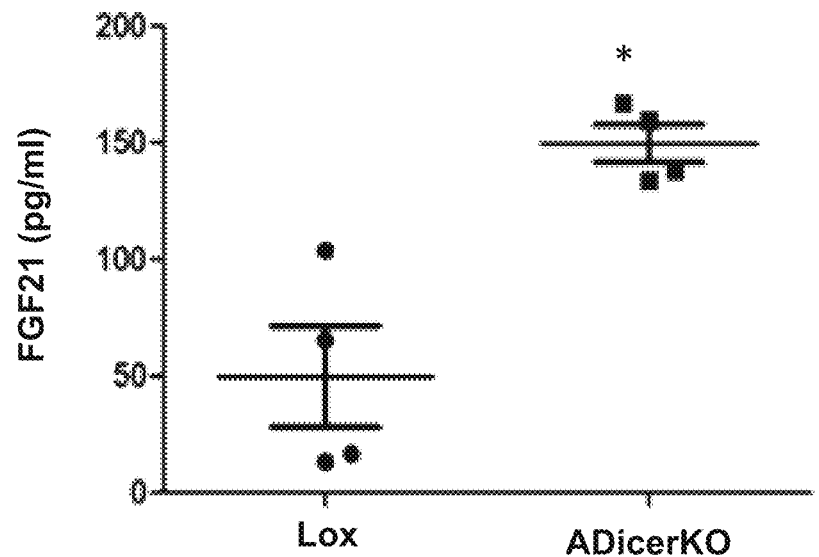
Figure 3B:
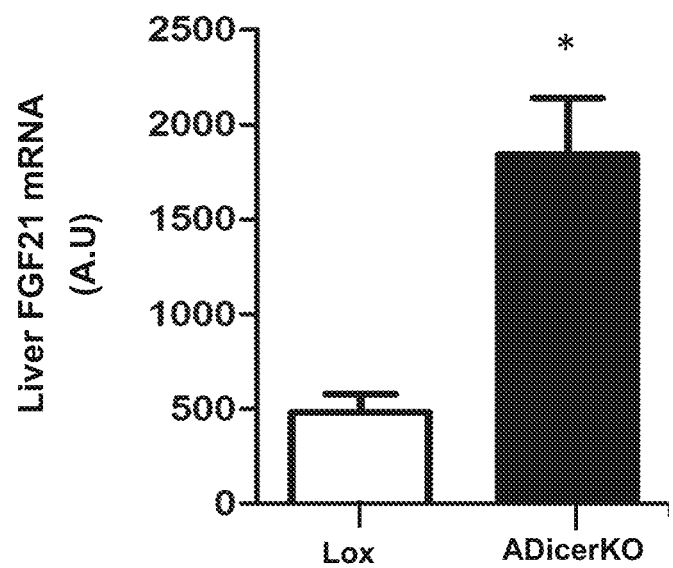
Figure 3C:
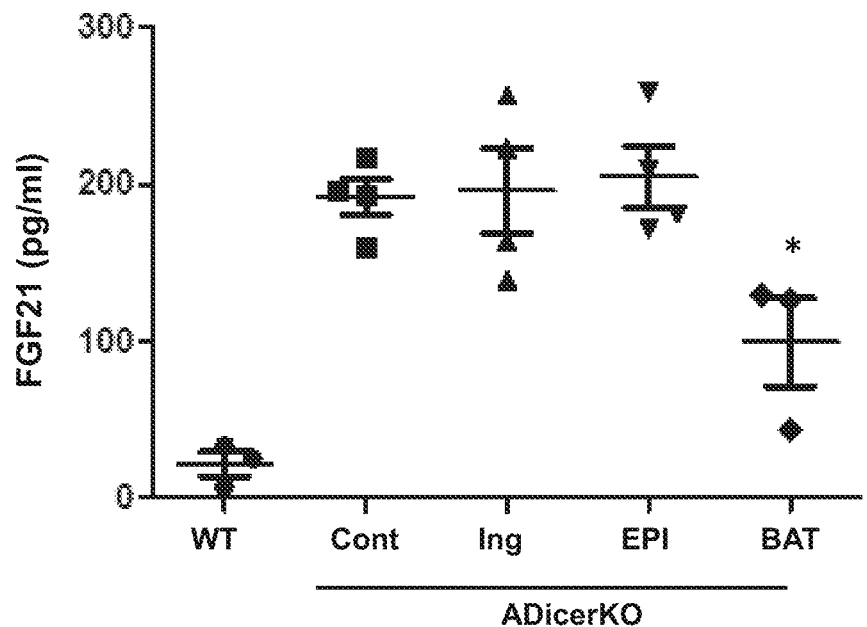
Figure 3D:
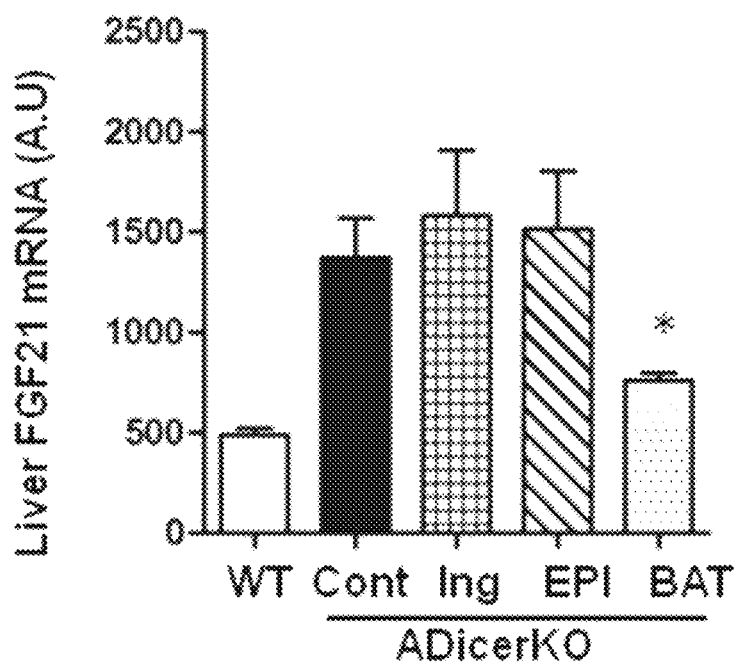

Example 3. Identification of FGF-21 as a Potential Target of Regulation by Circulating Exosomal miRNAs FGF21 is a member of the fibroblast growth factor family, which is produced in the liver and other tissues, released into the circulation and exerts effects on multiple tissues in the control of metabolism[23]. ADicerKO mice had a ~3-fold increase in circulating FGF21, associated with increased levels of FGF21 mRNA in liver, as well as muscle, fat and pancreas (FIGS. 3a and 3b, FIG. 8a). After sham surgery or transplantation of Ing-WAT or Epi-WAT, serum FGF21 levels and liver FGF21 mRNA remained unchanged in the ADicerKO mice (FIGS. 3c and 3d). However, ADicerKO mice that received BAT fat transplants showed an ~50% reduction in the increased FGF21 mRNA in liver (FIG. 3d). This was paralleled by a reduction of circulating FGF21 levels to near control levels (FIG. 3c), indicating that BAT transplantation provided some factor(s) that directly or indirectly regulated FGF21 expression in liver of the ADicerKO mice. Considering that one of these factors could be a circulating miRNA, miRDB analysis was performed using the online resource http://mirdb.org to identify miRNAs that might target the 3'-UTR of murine FGF21 mRNA[24]. Four miRNA candidates were identified (miR-99a, miR-99b, miR-100, and miR-466i) using miRDB analysis and incorporated into exosomes via electroporation.

For exosome loading, exosome preparations were isolated and diluted with PBS to final volume of 100 µl. Exosome preparations were mixed with 200 µl phosphate-buffered sucrose: 272 mM sucrose/7 mM $K_2HPO_4$ along with 10 nM of a miRNA mimic, and the mixture was pulsed at 500 mV and 250 µF resistance using a Biorad Gene Pulser (Biorad, Hercules, Calif.). Electroporated exosomes were further diluted with PBS and added to the target cells.

Figure 8B:
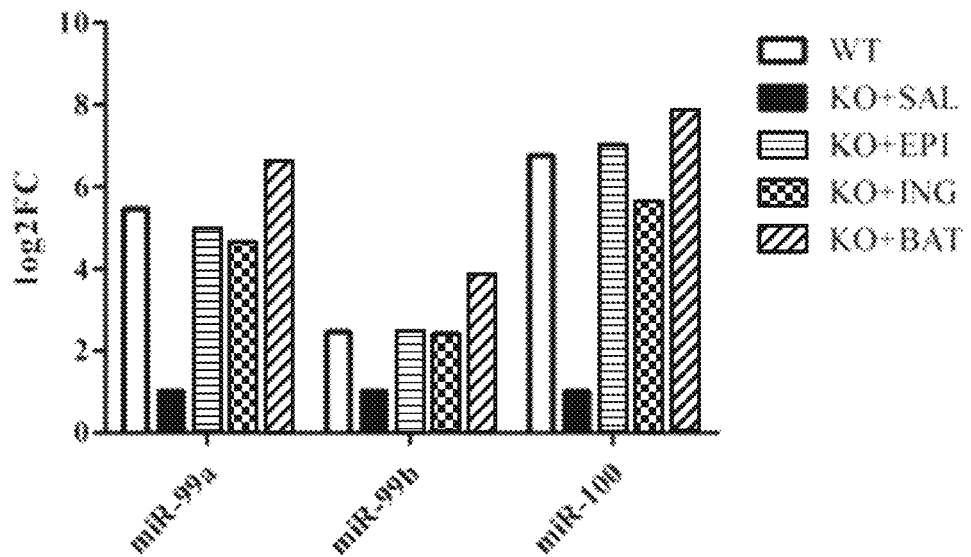
Figure 8C:
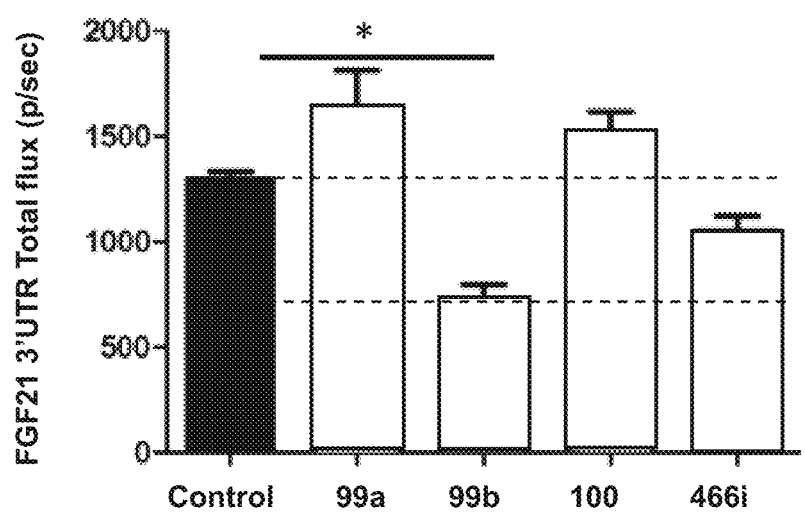

Three of the candidate miRNAs of these (miR-99a, -99b, and -100) were decreased by 75-80% in the serum of ADicerKO mice treated with saline (Sal) compared to control WT mice (FIG. 8b). This was consistent with the fact that these three miRNAs were all also highly expressed in BAT and Ing-WAT (Tables 7 and 8), and after BAT or Ing-WAT transplantation, there was a ~50% recovery of these three miRNAs in the serum of ADicerKO mice compared to treatment with saline (FIG. 8b).

TABLE 8 miRNAs restored in ADicerKO transplant groups more than 50% of the difference to WT and overlapping restored miRNAs

| BAT | EPI | ING |
|---|---|---|
| mmu-miR-17 | none | mmu-miR-183 |
| mmu-miR-103 | | mmu-miR-598 |
| mmu-miR-200b | | mmu-let-7d* |
| mmu-miR-128 | | mmu-miR-32 |
| mmu-miR-34a | | mmu-miR-33 |
| mmu-miR-21 | | mmu-miR-345-5p |
| mmu-miR-1 | | mmu-miR-135a* |
| mmu-miR-107 | | mmu-miR-669m |
| mmu-miR-140 | | mmu-miR-337-3p |
| mmu-miR-30e | | |
| mmu-miR-203 | | |
| mmu-miR-26a | | |
| mmu-miR-18a | | |
| mmu-miR-196a* | | |
| mmu-miR-540-3p | | |
| mmu-miR-146b | | |
| mmu-miR-497 | | |
| mmu-miR-150 | | |
| mmu-miR-511 | | |
| mmu-miR-322 | | |
| mmu-miR-20b* | | |
| mmu-miR-296-5p | | |

| BAT-EPI common | BAT-ING common | EPI-ING common | ALL common |
|---|---|---|---|
| mmu-miR-302c | mmu-miR-204 | mmu-miR-124 | mmu-miR-22 |
| mmu-miR-214 | mmu-let-7e | mmu-miR-129-3p | mmu-miR-19b |
| mmu-miR-29c | mmu-miR-199a-5p | mmu-miR-467e* | mmu-miR-19a |
| mmu-miR-324-5p | mmu-miR-188-3p | mmu-miR-181b | mmu-miR-323-5p |
| mmu-miR-10a | mmu-miR-7a | mmu-miR-183* | mmu-miR-92b |
| mmu-miR-1943 | mmu-miR-197 | | mmu-let-7a |
| mmu-miR-15b | mmu-let-7g | | mmu-miR-193b |
| mmu-miR-669i | mmu-miR-188-5p | | mmu-miR-15a |
| mmu-miR-99b* | mmu-miR-298 | | mmu-miR-133b |
| mmu-miR-199b | mmu-miR-101b | | mmu-miR-185 |
| mmu-miR-126-5p | mmu-miR-301a | | mmu-miR-291a-5p |
| mmu-miR-300 | mmu-miR-26b | | mmu-miR-207 |
| mmu-miR-2140 | mmu-miR-186 | | mmu-miR-212 |
| mmu-miR-1895 | mmu-miR-770-3p | | mmu-let-7c |
| mmu-miR-151-3p | mmu-miR-130b | | mmu-miR-25 |
| mmu-miR-1197 | mmu-miR-184 | | mmu-miR-195 |
| mmu-miR-876-3p | mmu-miR-1952 | | mmu-miR-92a |
| mmu-miR-10b | mmu-miR-296-3p | | mmu-miR-27a |
| mmu-miR-1899 | mmu-miR-30e* | | mmu-miR-16 |
| mmu-miR-1898 | mmu-miR-301b | | mmu-miR-24 |
| mmu-miR-711 | mmu-miR-210 | | mmu-miR-29a |
| mmu-miR-92a* | mmu-miR-872* | | mmu-miR-130a |
| mmu-miR-350 | mmu-miR-134 | | mmu-miR-145 |
| mmu-miR-181a | | | mmu-miR-205 |
| mmu-miR-151-5p | | | mmu-miR-101a |
| mmu-miR-2133 | | | mmu-miR-20b |
| | | | mmu-miR-328 |
| | | | mmu-miR-20a |
| | | | mmu-miR-326 |
| | | | mmu-miR-148a |
| | | | mmu-miR-222 |
| | | | mmu-miR-181d |
| | | | mmu-miR-133a |
| | | | mmu-miR-148b |
| | | | mmu-miR-106a |
| | | | mmu-miR-335-3p |
| | | | mmu-miR-127* |
| | | | mmu-miR-125a-3p |
| | | | mmu-miR-706 |
| | | | mmu-miR-146a |
| | | | mmu-miR-30d |
| | | | mmu-miR-93 |
| | | | mmu-miR-297a |
| | | | mmu-miR-99a |
| | | | mmu-miR-100 |
| | | | mmu-miR-338-5p |
| | | | mmu-miR-129-5p |
| | | | mmu-miR-30b |
| | | | mmu-miR-200a |
| | | | mmu-miR-1955 |
| | | | mmu-miR-199a-3p |
| | | | mmu-miR-191 |
| | | | mmu-miR-320 |
| | | | mmu-miR-31* |
| | | | mmu-let-7b |
| | | | mmu-miR-149 |
| | | | mmu-miR-339-5p |
| | | | mmu-miR-324-3p |
| | | | mmu-let-7d |
| | | | mmu-miR-346 |
| | | | mmu-miR-760 |
| | | | mmu-miR-342-3p |
| | | | mmu-miR-194 |
| | | | mmu-miR-218 |
| | | | mmu-miR-130b* |
| | | | mmu-miR-152 |
| | | | mmu-miR-99b |
| | | | mmu-miR-1954 |
| | | | mmu-miR-139-3p |
| | | | mmu-miR-1983 |
| | | | mmu-miR-187 |
| | | | mmu-miR-879* |

"*" indicates star species miRNA, in which the 3'-5' fragment induces the repression.

Figure 8D:
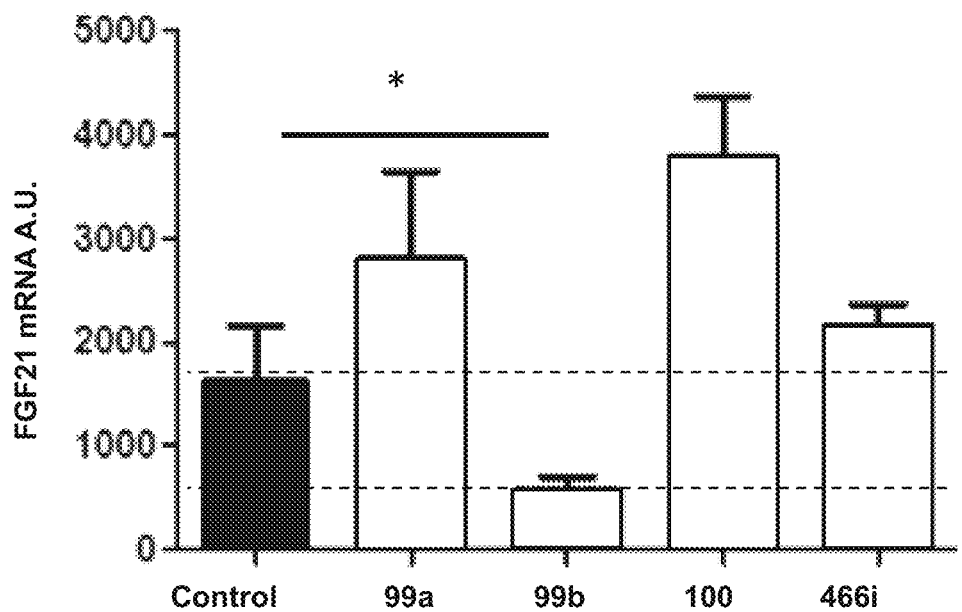

To determine which of these candidate miRNAs might regulate FGF21, AML-12 liver cells were transfected with an adenoviral pacAd5-FGF21 3'-UTR luciferase reporter (SEQ ID No: 4) and then with 10 nM of the candidate miRNA (miR-99a, Accession No: MIMAT0000131; miR-99b, Accession No: MIMAT0000132; mir-100, Accession No: MIMAT0000655; mir-466i, Accession No: MIMAT0017325) or a control miRNA mimetic (Thermo Fisher Cat. Number AM17110). Of these, only miR-99b resulted in a robust reduction of FGF21 luciferase activity (FIG. 8c), and this correlated with a reduction in FGF21 mRNA level by 65% (FIG. 8d).

Figure 3E:
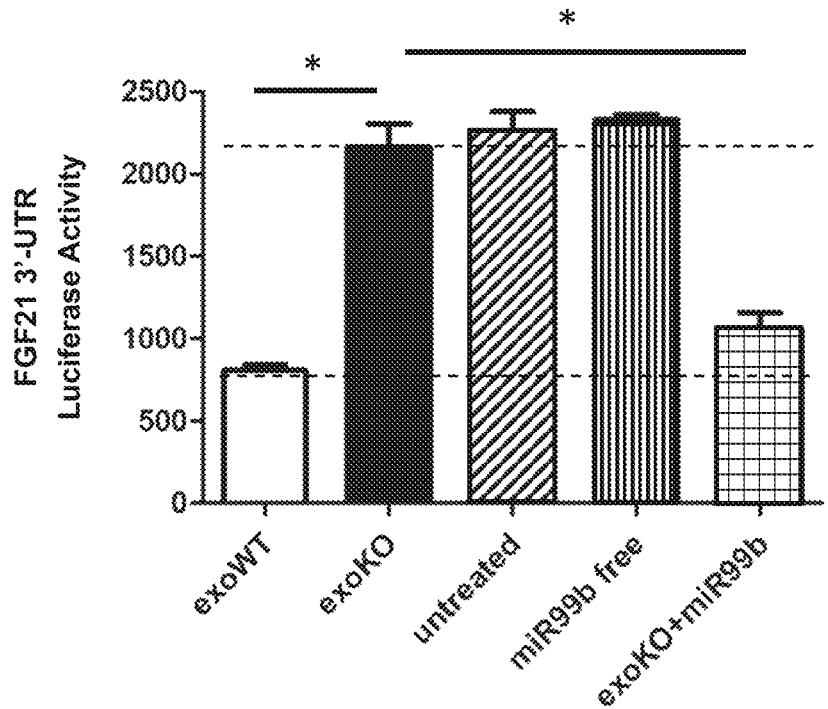
Figure 3F:
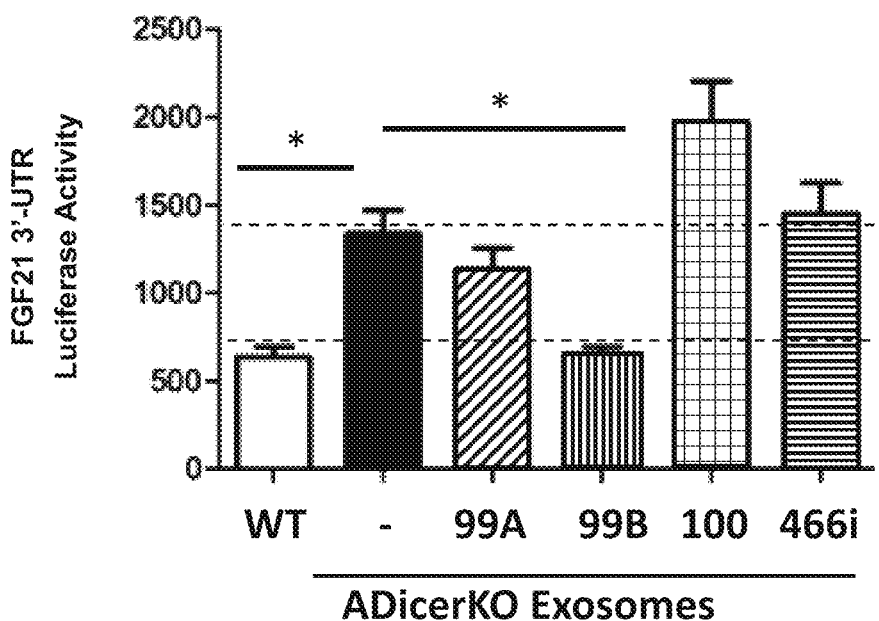
Figure 8E:
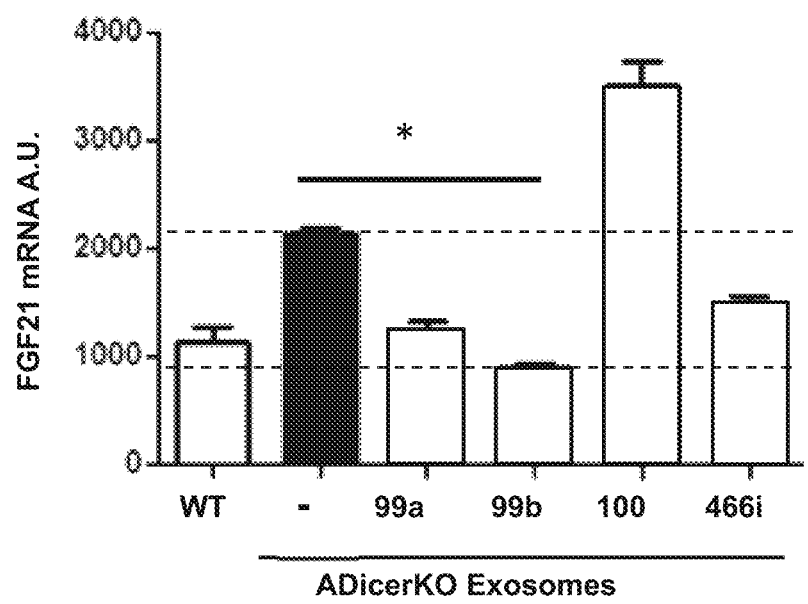

To test directly if these miRNAs could regulate FGF21 when present in exosomes, AML-12 cells expressing the FGF21-3'UTR luciferase reporter (SEQ ID No: 4) were exposed to exosomes from control or ADicerKO mice or ADicerKO exosomes which had been electroporated with either miR-99a, miR-99b, miR-100, miR-466i or a control mimic. In vitro the isolated exosomes from control mice were able to suppress FGF21-3'UTR luciferase activity in the AML-12 cells by 60%, while the exosomes from the ADicerKO (untreated) had no effect (FIG. 3e, left 3 bars). Furthermore, while ADicerKO exosomes reconstituted with miR-99a, miR-100 or miR-466i had minimal effects (data not shown), ADicerKO exosomes bearing miR-99b resulted in a 55% suppression of the FGF21 luciferase activity (FIG. 3f), and again this was paralleled by an almost equal reduction in FGF21 mRNA levels, mimicking the effect of wild type exosomes (FIG. 8e). This in vitro regulation of FGF21 was dependent on exosomal delivery and was not recapitulated with when naked miRNA was incubated with these cells ("miR99b free"), indicating the potency of exosomes as a miRNA delivery system (FIG. 3e, right 2 bars).

Figure 4A:
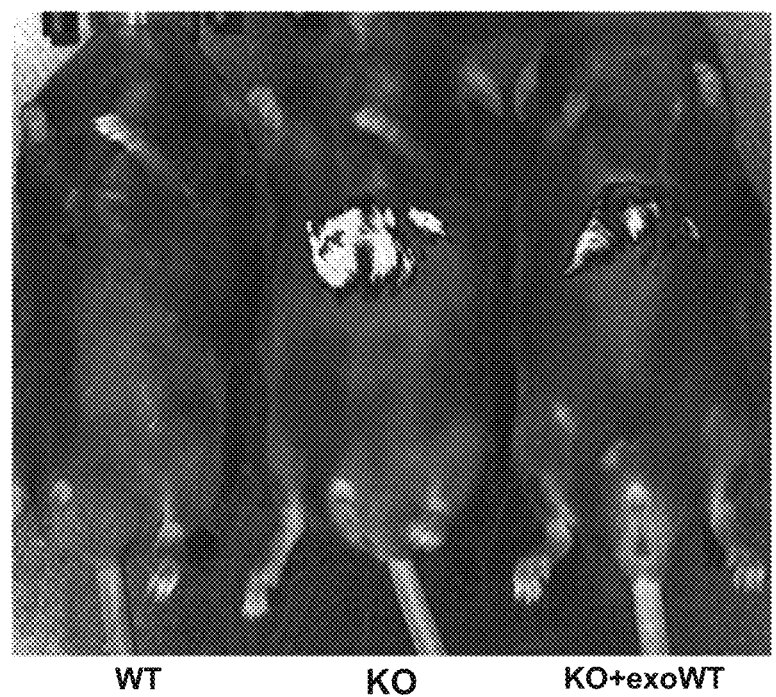
Figure 4B:
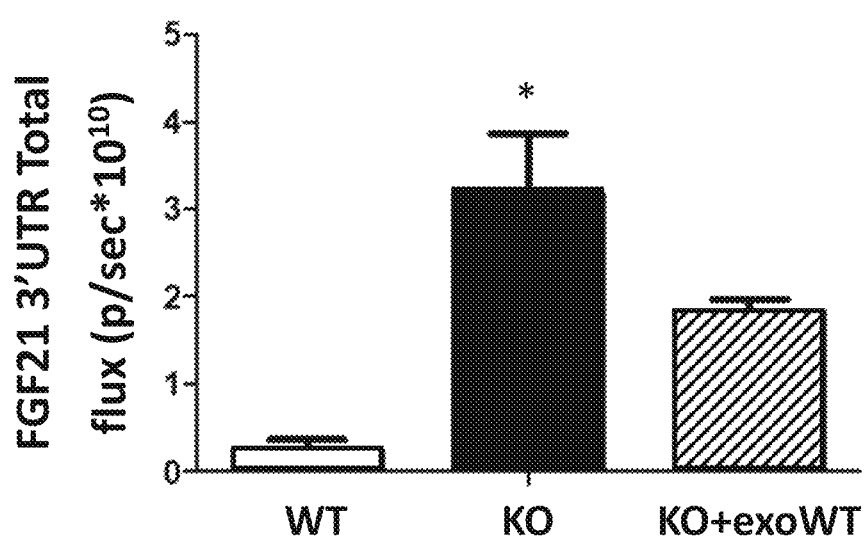
Figure 4C:
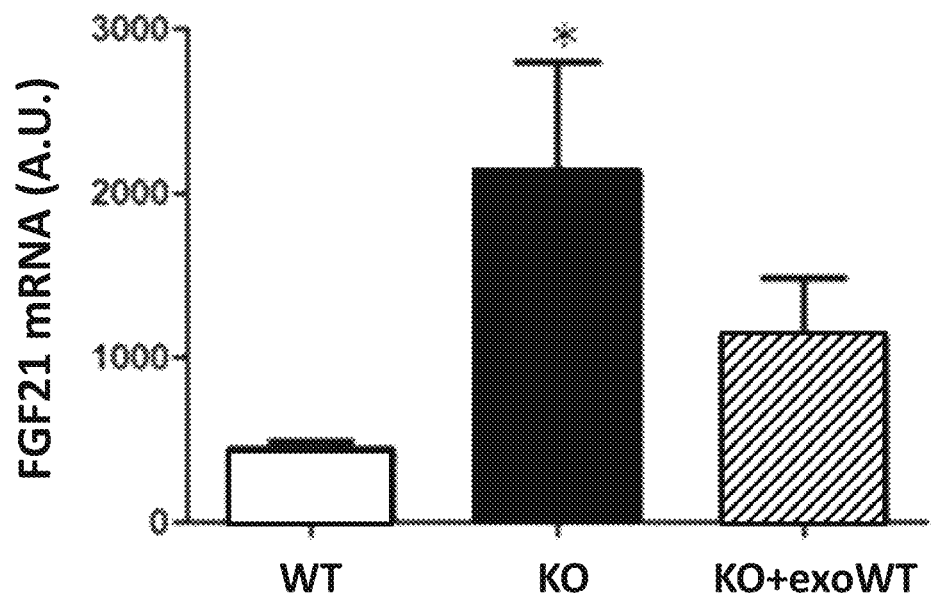
Figure 4D:
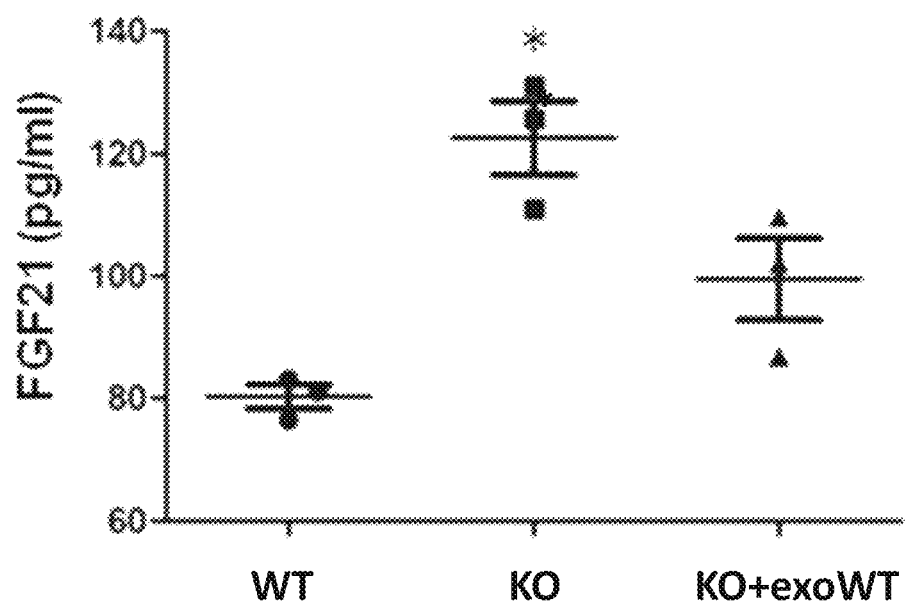

In order to address possible regulation of FGF21 by exosomal miRNAs in vivo, ADicerKO and WT mice were transduced with a pacAd5-FGF21 3'-UTR luciferase reporter (SEQ ID No: 4), injected with exosomes from ADicerKO mice (i.e., exosomes with low miRNA content), and hepatic FGF21 suppression was measured using the IVIS in vivo imaging system. Consistent with the in vitro study, FGF21 3'-UTR activity was 5-fold higher in ADicerKO mice than WT mice, reflecting the absence of repressive miRNAs in the circulation of the ADicerKO mice (FIGS. 4a and 4b). Injection of WT-exosomes in the AdicerKO re-induced suppression of the elevated FGF21 3'-UTR reporter activity by 59% of the excess above controls. qPCR from liver samples from the WT, KO, and KO+exoWT mice showed reduced hepatic FGF21 message by 30% of the way toward normal compared to KO mice only and also reduced circulating FGF21 by 25% compared to KO mice only (FIGS. 4c and 4d).

Figure 4E:
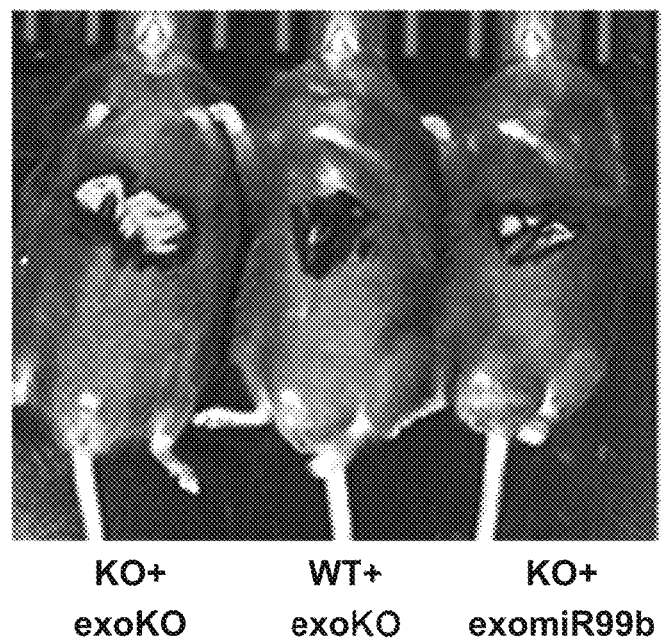
Figure 4F:
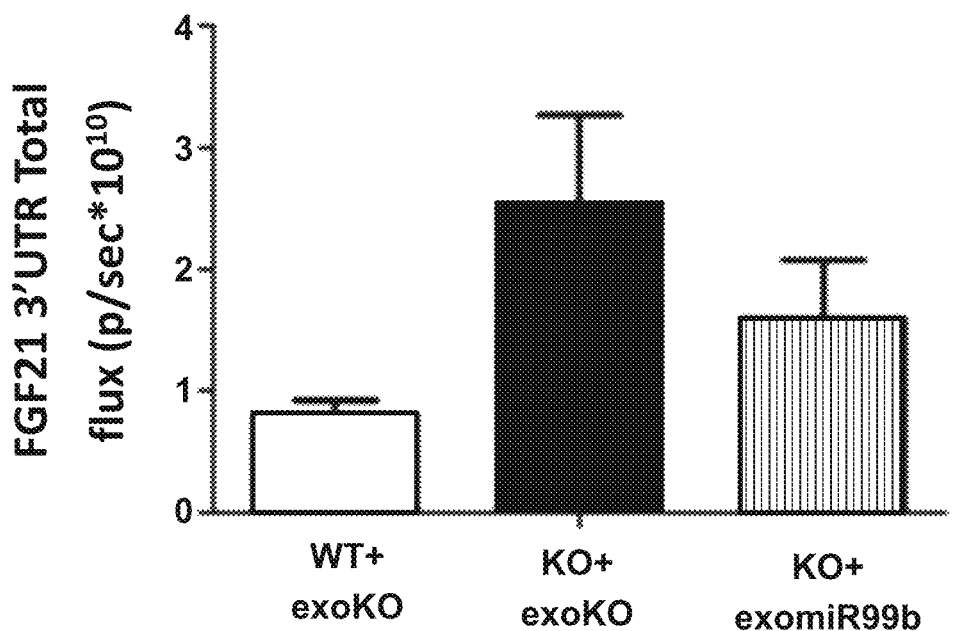
Figure 4G:
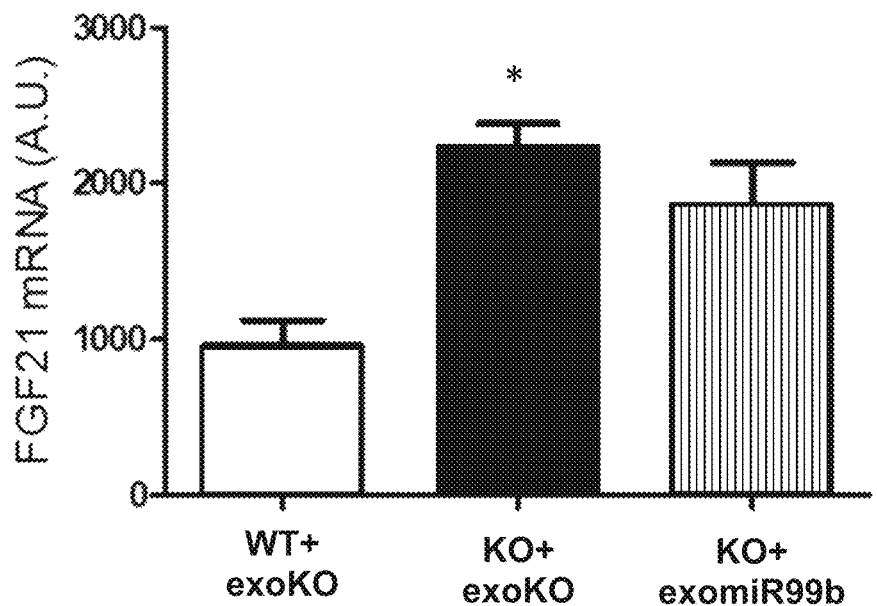
Figure 4H:
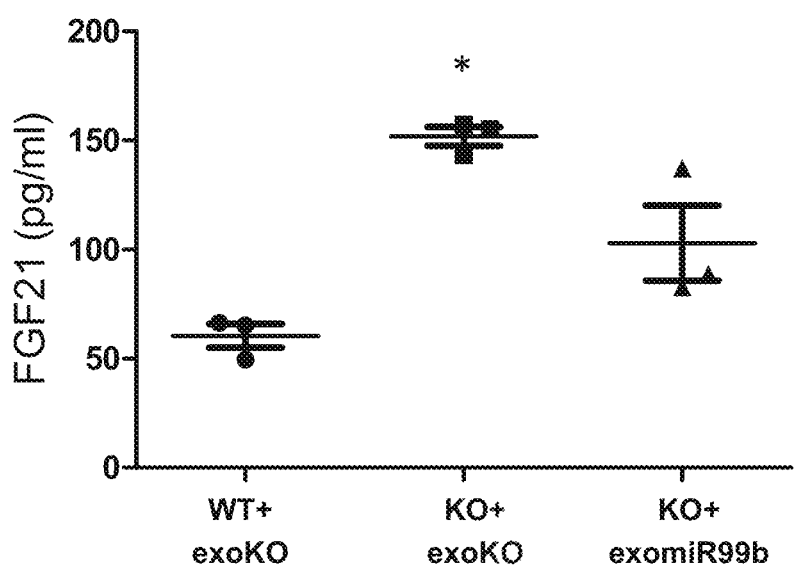

In a separate experiment the contribution of miR-99b in the regulation of FGF21 in vivo was also assessed by injecting WT and KO mice with KO exosomes with or without reconstitution of miR-99b (FIG. 4e). Again KO mice showed 2.5-fold higher luciferase activity than WT mice, even when both were given exosomes from KO mice. Administration of KO exosomes reconstituted with miR-99b (exomiR99b) in the AdicerKO re-induced suppression of the FGF21 3'-UTR reporter mice by 45% compared to normal (FIG. 4f). qPCR from liver samples from the WT, KO, and KO+exo-miR-99b mice showed a parallel reduction in hepatic FGF21 message (FIG. 4g). This effect was further paralleled by reduced circulating FGF21 in the KO mice (FIG. 4h).

These data indicate that fat-derived exosomes are a highly efficient means of delivering exosomes.

Example 4. Demonstration of Regulation of Liver Gene Expression by an Adipose Tissue Produced Circulating Exosomal miRNA Regulation of FGF21 both at the mRNA and circulating levels is a complex process, which almost certainly involves more than regulation by circulating miRNAs. However, consistent with the liver effect being secondary to BAT produced miRNAs based on transplant experiments, in our transplantation study miRNAs including miR-16, miR-201 and miR-222, which are relatively fat-specific, were significantly decreased in livers of ADicerKO mice and restored toward normal by BAT transplant (FIG. 9a), whereas the pre-miRNA-16 species in the liver were not changed in ADicerKO mice with or without BAT transplantation (FIG. 9b). To better define the potential of adipose-derived circulating miRNAs in vivo, a more specific reporter system was developed. To this end, experiments took advantage of the human miRNA hsa_miR-302f and its 3'UTR reporter[25] (SEQ ID No: 3), since this miRNA is human specific and does not have a mouse homolog. We then performed two types of experiments. In Protocol 1 (FIG. 5a), an adenovirus bearing pre-hsa_miR-302f or its LacZ control was injected directly into BAT, using an approach that has been shown to get BAT specific expression of the transduced gene[26]. Three days later, the same mice were injected intravenously (i.v.) with an adenovirus bearing the 3'-UTR luciferase reporter for hsa_miR-302f (SEQ ID No: 3) to induce its expression in liver. Only if there was communication between the miRNA expressed in BAT and the reporter expressed in liver would suppression of the reporter be observed.

Figure 5A:
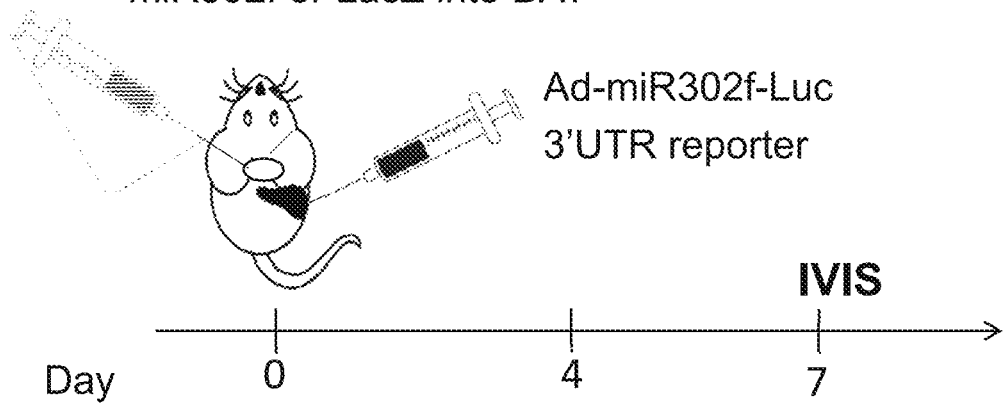
Figure 5B:
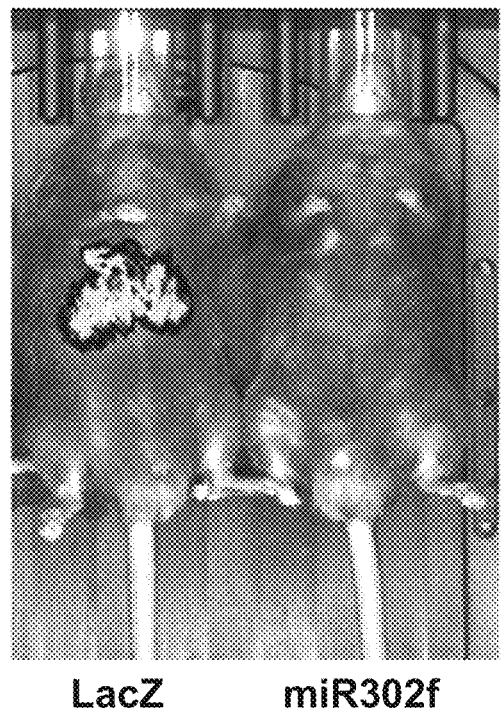
Figure 5C:
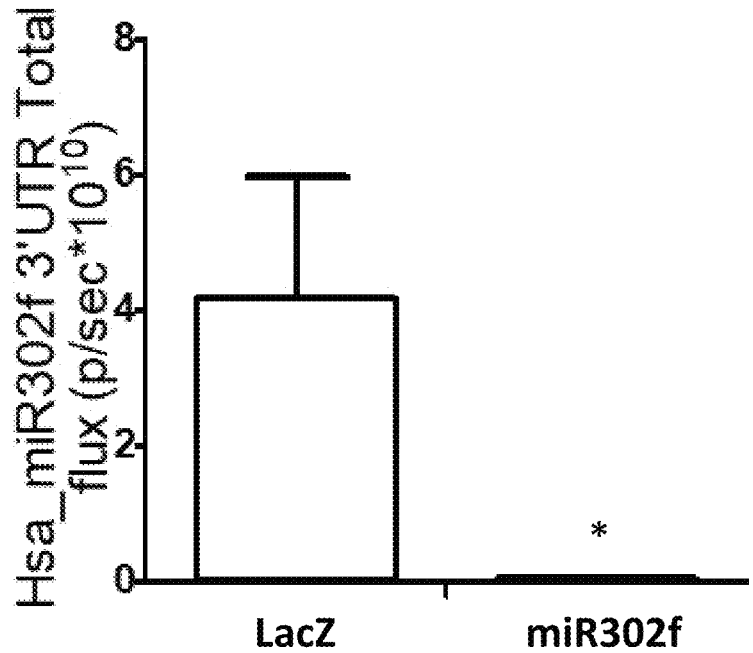
Figure 5D:
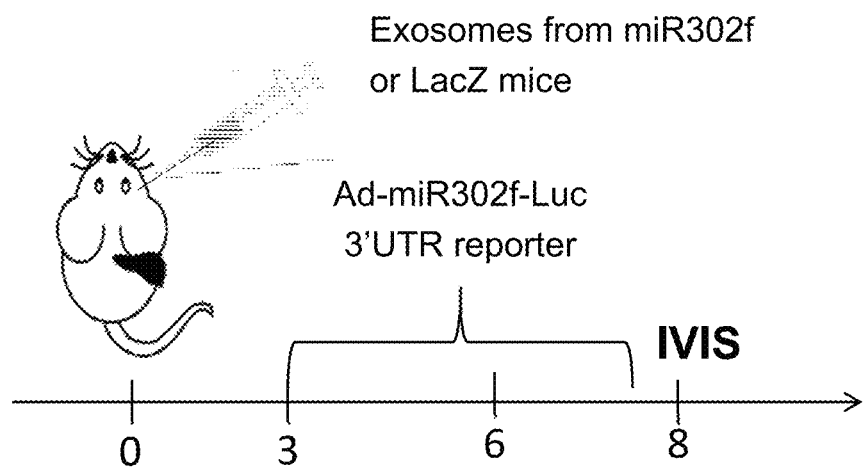
Figure 5E:
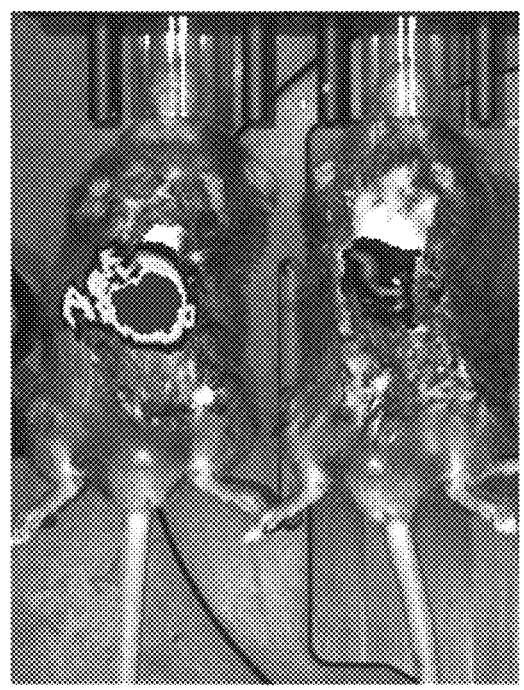
Figure 5F:
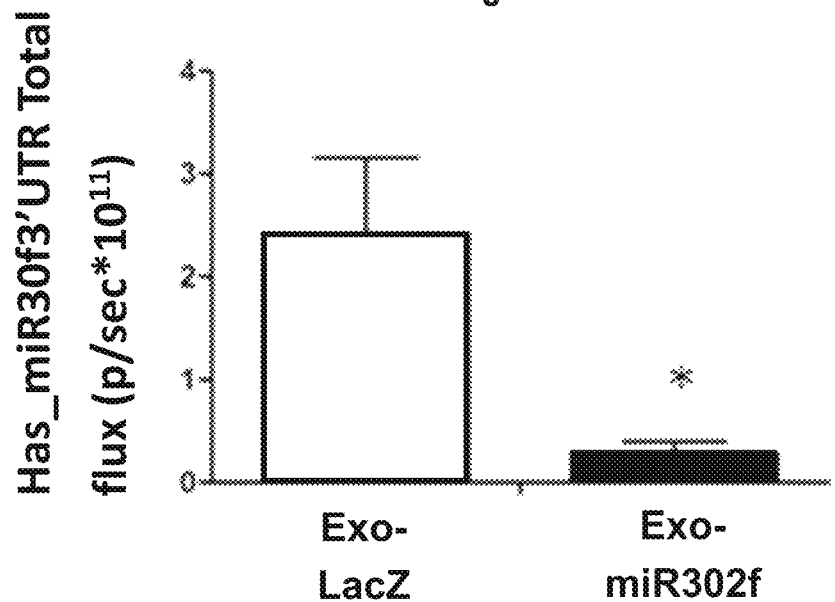
Figure 5G:
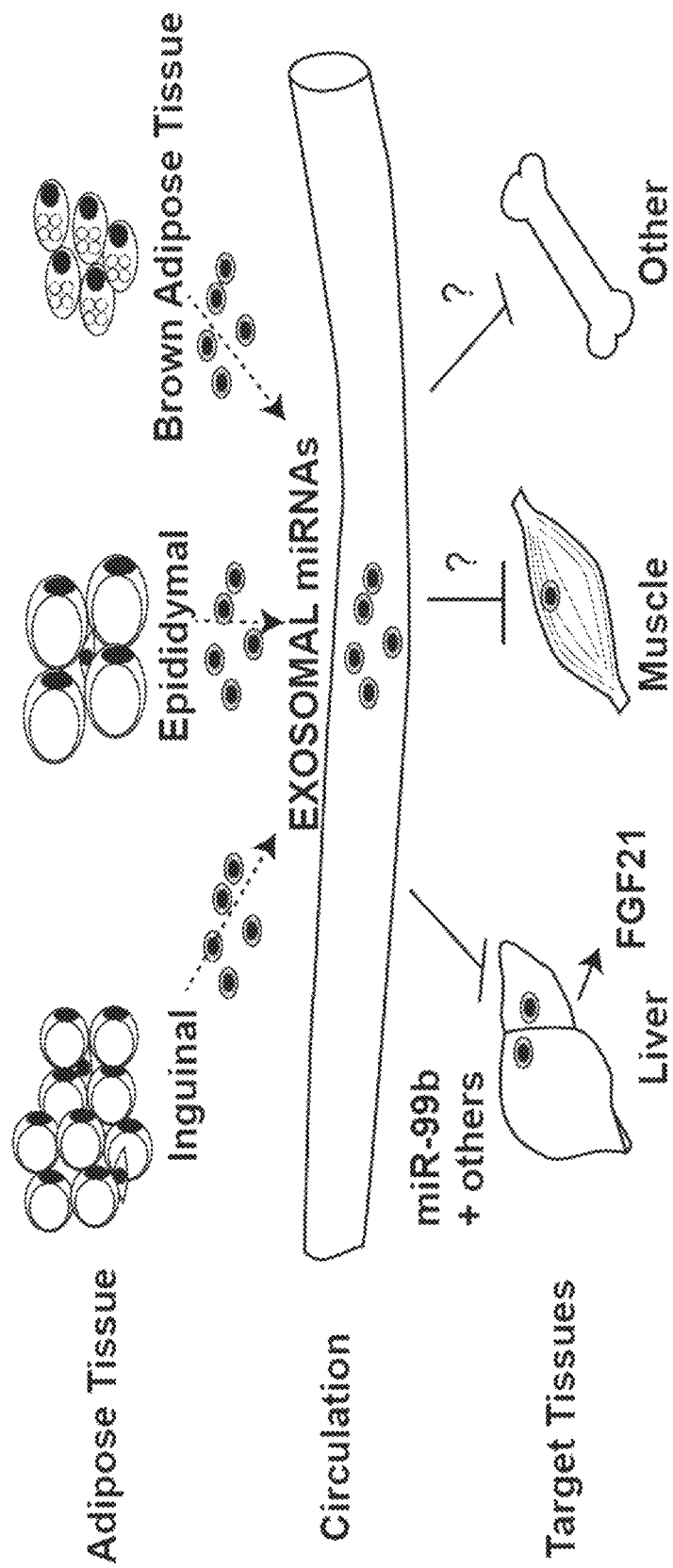

Indeed, IVIS analysis 5 days after transfection revealed that in mice with Ad-hsa_miR-302f transduced in BAT there was a >95% reduction of luciferase activity in the liver when compared to mice in which the LacZ control was transduced into BAT (FIGS. 5b and 5c). In protocol 2 (FIG. 5d), in order to definitively address whether this hsa_miR-302f suppression of luciferase in the liver was contingent upon exosomal delivery or not, two separate cohorts of C57Bl/6 mice were used. One cohort was transduced with the adenovirus bearing pre-hsa_miR-302f (SEQ ID No: 1) or the control LacZ adenovirus (SEQ ID No: 2) directly into BAT. A second, separate cohort of mice (the acceptor) was transduced in the liver by i.v. injection of the adenovirus bearing the 3'-UTR of hsa_miR-302f in-frame with a luciferase reporter (SEQ ID No: 3). Serum was then isolated from the donor cohorts three times over the following 8 days, exosomes were isolated, and the purified exosomes were injected intravenously into the acceptor mice, after which IVIS analysis of the hsa_miR-302f reporter in the acceptor mice was performed. To prepare serum exosomes, serum was centrifuged at 1000×g for 5 min and then at 10,000×g for 10 min to remove whole cells, cell debris and aggregates. The serum was subjected to 0.1 µm filtration and ultracentrifuged at 100,000×g for 1 h. Pelleted vesicles were suspended in PBS and ultracentrifuged again at 100,000×g for washing. Pelleted vesicles were finally resuspended in 100 ul sterile 1×PBS.

Compared to the mice receiving exosomes from the control Ad-LacZ BAT transduced mice, the acceptor mice injected with exosomes originating from Ad-hsa_miR-302f BAT transduced mice showed a remarkable 95% reduction of luciferase activity in the liver (FIGS. 5e and 5f), thus demonstrating the direct regulation of this adipose-produced circulating miRNA on gene expression in the liver of the recipient mice.

In order to show that miR302f expression is BAT specific and does not leak into the liver following adenoviral injection, viral DNA isolation was performed from livers of the animals used in the experimental protocols 1 and 2 and the viral DNA was analyzed by qPCR detecting miR-302f or LacZ. The same procedure was performed for BAT samples from experimental protocol 1. As is evident in FIG. 9C, no adenoviral miR-302f or LacZ can be detected via qPCR in the liver, contrary to BAT.

Taken together, these data show that adipose tissue is a major source of circulating exosomal miRNAs in both mice and humans. This is demonstrated by the fact that both AdicerKO mice, which lack miRNA processing in adipose tissue, and humans with congenital or HIV-related lipodystrophy, who have severely reduced adipose mass or a defect in Dicer expression in fat, have dramatically reduced levels of one-third to one-half of the circulating exosomal miRNAs. Furthermore, in the ADicerKO mice many of the decreased miRNAs are restored to near normal levels following transplantation of adipose tissue from normal mice, with the pattern of serum miRNAs reflecting the pattern observed in the fat depot used for transplantation. Thus, although many tissues can secrete exosomes, our data show that adipose tissue is a major source of circulating exosomal miRNAs and that different adipose depots contribute different sets of miRNAs with subcutaneous WAT and BAT being the greatest contributors, at least in the mouse.

These data also demonstrate that the circulating exosomal miRNAs derived from fat may act as regulators of whole body metabolism and mRNA translation in other tissues. Thus, adipose tissue transplantation, especially BAT transplantation, improves glucose tolerance and lowers circulating insulin and FGF21 levels, as well as hepatic FGF21 mRNA in the recipient mouse. The latter appears to be due to a direct effect of the circulating miRNAs on FGF21 translation in liver, as incubation of serum exosomes from control mice with liver cells in vitro can lower FGF21 mRNA levels and repress activity of a FGF21 3'-UTR reporter. This does not occur with exosomes isolated from serum of ADicerKO mice, but can be reconstituted in vitro, at least in part, by introduction of miR-99b, a predicted regulator of murine FGF21, into these exosomes. miR-99b is also one of the miRNAs that is highly reduced in circulating exosomes of ADicerKO mice, and one whose level is largely restored by BAT transplantation. Transplantation with Ing-WAT also significantly restored the level of miR-99b in the circulation, but only the BAT transplantation reduced hepatic FGF21 mRNA. This suggests that BAT-derived exosomes may preferentially target the liver compared to Ing-WAT exosomes. Such tissue targeting has been suggested by in vitro studies[18,27] showing that pancreatic exosomes preferentially target peritoneal macrophages as compared to granulocytes or T-lymphocytes[28], implying that inter-organ exosomal delivery has tissue specificity[29]. The generalizability of this type of cross-talk between adipose tissue and liver mRNA regulation, is made ever clearer by the use of a miRNA and miRNA reporter system which is human specific. Hence, when the BAT of mice is transduced with an adenovirus producing the human-specific miRNA hsa_miR-302f, exosomes present in the circulation of that mouse can target an hsa_miR-302f 3'-UTR reporter in the liver of the same mouse or even a different mouse given isolated exosomes from this donor.

Since adipose tissue is a major source of circulating miRNAs, the effect of the loss of adipose-derived miRNAs in lipodystrophy and their restoration by fat transplantation may involve many targets and tissues in addition to hepatic FGF21. miRDB analysis of the miRNAs that are restored with BAT transplantation group also includes miR-325 and miR-743b (predicted to target UCP-1) and miR-98 (predicted to target PGC1α), suggesting that adipose tissue-derived secreted miRNAs may have both paracrine and endocrine actions and be contributors to multiple aspects of the lipodystrophy phenotype of the ADicerKO mouse, including enlargement and "whitening" of the interscapular BAT fat pad[14]. Regulation of metabolism and mRNA expression in lipodystrophy could also involve other miRNAs or exosomal factors contributed to the circulation by BAT, as well as a whole range of non-exosomal mechanisms, including conventional adipokines and cytokines, such as leptin, adiponectin, and IL6, as well as metabolic intermediates and other hormones[30]. What is clear from the present study is that in addition to serving as markers of disease, exosomal miRNAs may have increased potential for transfer of miRNAs between tissues and serve a regulatory role[31,32]. In vitro, endothelial exosomes that carry miR-126 have been shown to target vascular cells inducing protection from apoptosis[33]. Likewise, exosomes isolated from mast cells in vitro can trigger other mast cells, enhancing their antigen presenting potential[29], and Ismail et al. have shown that exosomes secreted by macrophages and platelets can be taken up by naive monocytes, which then differentiate into macrophages[32]. Exosomal miRNA transfer has been also reported in glioblastoma cancers, which secrete exosomes with specific miRNAs (let-7a, miR-16, miR-320) besides EGFR receptors[15,34]. Another example of transfer of miRNAs through exosomes has been reported to occur between embryonic stem cells and mouse embryonic fibroblasts[35].

In summary, these data show that a major source of circulating exosomal miRNAs is adipose tissue and that different adipose depots contribute different exosomal miRNAs into the circulation. The data also show that these adipose-derived circulating miRNAs can have far-reaching systemic effects, including regulation of mRNA expression and translation. As a product of different adipose depots, these exosomal miRNAs could also change in level in diseases with altered fat mass, such as lipodystrophy and obesity, altered adipose distribution, and altered adipose tissue function. Thus, adipose-derived exosomal miRNAs constitute a novel class of adipokines that can be secreted by fat and act as regulators of metabolism in distant tissues providing a new mechanism of cell-cell crosstalk.

REFERENCES

[1] Krol, J., Loedige, I., and Filipowicz, W., *Nat Rev Genet* 11 (9), 597.
[2] Sun, L. et al., *Nat Cell Biol* 13 (8), 958; Bartel, D. P., *Cell* 136 (2), 215 (2009); Ameres, S. L. and Zamore, P. D., *Nat Rev Mol Cell Biol* 14 (8), 475.
[3] Trajkovski, M. et al., *Nature* 474 (7353), 649.
[4] Arroyo, J. D. et al., *Proc Natl Acad Sci USA* 108 (12), 5003.
[5] Thery, C., Amigorena, S., Raposo, G., and Clayton, A., *Curr Protoc Cell Biol* Chapter 3, Unit 3 22 (2006).
[6] Gyorgy, B. et al., *Cell Mol Life Sci* 68 (16), 2667.
[7] Hata, A. and Lieberman, J., *Sci Signal* 8 (368), re3.
[8] Dumortier, O., Hinault, C., and Van Obberghen, E., *Cell Metab* 18 (3), 312.
[9] Arner, E. et al., *Diabetes* 61 (8), 1986.
[10] Capobianco, V. et al., *J Proteome Res* 11 (6), 3358.
[11] Caroli, A., Cardillo, M. T., Galea, R., and Biasucci, L. M., *J Cardiol* 61 (5), 315.
[12] Guay, C. et al., *Transl Res* 157 (4), 253.
[13] Mori, M. A. et al., *Cell Metab* 16 (3), 336.
[14] Mori, M. A. et al., *J Clin Invest* 124 (8), 3339.
[15] Skog, J. et al., *Nat Cell Biol* 10 (12), 1470 (2008).
[16] Taylor, D. D., Zacharias, W., and Gercel-Taylor, C., *Methods Mol Biol* 728, 235.
[17] Escola, J. M. et al., *J Biol Chem* 273 (32), 20121 (1998).
[18] Fevrier, B. and Raposo, G., *Curr Opin Cell Biol* 16 (4), 415 (2004).
[19] Ortega, F. J. et al., *PLoS One* 5 (2), e9022; Oger, F. et al., *J Clin Endocrinol Metab* 99 (8), 2821.
[20] Chou, W. W. et al., *Cell Physiol Biochem* 32 (1), 127.
[21] Keller, P. et al., *BMC Endocr Disord* 11, 7.
[22] McGregor, R. A. and Choi, M. S., *Curr Mol Med* 11 (4), 304.
[23] Potthoff, M. J., Kliewer, S. A., and Mangelsdorf, D. J., *Genes Dev* 26 (4), 312; Badman, M. K. et al., *Cell Metab* 5 (6), 426 (2007).
[24] Wong, N. and Wang, X., *Nucleic Acids Res* 43 (Database issue), D146.
[25] Yao, Y. et al., *Mol Med Rep* 2 (6), 963 (2009).
[26] Uhrig-Schmidt, S. et al., *PLoS One* 9 (12), e116288.
[27] Atai, N. A. et al., *J Neurooncol* 115 (3), 343.
[28] Zech, D., Rana, S., Buchler, M. W., and Zoller, M., *Cell Commun Signal* 10 (1), 37.

29 Valadi, H. et al., *Nat Cell Biol* 9 (6), 654 (2007).
30 Bluher, M., *Mol Metab* 3 (3), 230.
31 Thery, C., Ostrowski, M., and Segura, E., *Nat Rev Immunol* 9 (8), 581 (2009); Bang, C. et al., *J Clin Invest* 124 (5), 2136; Hergenreider, E. et al., *Nat Cell Biol* 14 (3), 249; Mittelbrunn, M. et al., *Nat Commun* 2, 282.
32 Ismail, N. et al., *Blood* 121 (6), 984.
33 Zernecke, A. et al., *Sci Signal* 2 (100), ra81 (2009).
34 van der Vos, K. E. et al., *Neuro Oncol* 18 (1), 58.
35 Yuan, A. et al., *PLoS One* 4 (3), e4722 (2009).
36 Gallo, A., Tandon, M., Alevizos, I., and Illei, G. G., *PLoS One* 7 (3), e30679.
37 Turchinovich, A., Weiz, L., Langheinz, A., and Burwinkel, B., *Nucleic Acids Res* 39 (16), 7223.
38 Vickers, K. C. et al., *Nat Cell Biol* 13 (4), 423.

We claim:

1. A liver-specific delivery system, comprising: an exosome derived from an adipocyte or preadipocyte isolated from brown or beige adipose tissue, a targeting moiety that is not naturally expressed on the exosome, and a recombinant nucleic acid that is not naturally found within the exosome ranging in size from about 10 to several thousand nucleotides.

2. The delivery system of claim 1, wherein the recombinant nucleic acid is short hairpin RNA (shRNA), small nucleolar RNA (snoRNA), long non-coding RNA (LncRNA), micro RNA (miRNA), DNA, or RNA.

3. The delivery system of claim 1, wherein the recombinant nucleic acid is about 10, 50, 100, 500, 1000, 2000, or 3000 nucleotides.

4. The delivery system of claim 1, wherein the exosome is derived from a human.

5. The delivery system of claim 1, wherein the targeting moiety functions to regulate uptake of the exosome by tissues within a subject.

6. The delivery system of claim 1, further comprising a recombinant protein, wherein the recombinant protein is part of the CRISPR-Cas ribonucleoprotein complex.

7. The delivery system of claim 1, wherein the targeting moiety is conjugated to the exosome, wherein the targeting moiety is conjugated to the exosome by expressing the targeting moiety as a fusion protein together with an exosomal transmembrane protein.

8. The delivery system of claim 1, wherein the targeting moiety is one or more of Asialoglycoprotein Receptor (ASGPR), Toll-Like Receptor 4 ligand (TLR-4 ligand), Notch, CGS-21680, Parathyroid hormone receptor 1 (PTHR1), and Fractalkine receptor (CX3CR1).

9. A method for producing a liver-specific adipose-derived exosome delivery system comprising an exosome derived from an adipocyte or preadipocyte isolated from brown or beige adipose tissue, wherein the method comprises:
a. isolating brown or beige adipose tissue from a subject;
b. isolating adipocytes or preadipocytes from the brown or beige adipose tissue; and
c. contacting the isolated adipocytes or preadipocytes with a nucleic acid vector comprising nucleic acids capable of expressing one or more RNA, thereby producing a liver-specific delivery system comprising an exosome derived from an adipocyte or preadipocyte isolated from brown or beige adipose tissue.

10. The method of claim 9, wherein the subject is human.

11. The method of claim 9, wherein the nucleic acids are a small interfering RNA (siRNA), short hairpin RNA (shRNA), a small nucleolar RNA (snoRNA), a long non-coding RNA (LncRNA), and/or a micro RNA (miRNA).

12. The method of claim 9, wherein the nucleic acids are about 3000, 2000, 1000, 500, 100, 50, 40, 30, 20, 15, or 10 nucleotides.

13. The method of claim 9, further comprising a step (d), wherein step (d) comprises contacting the isolated adipocytes or preadipocytes with a nucleic acid vector comprising nucleic acids encoding a targeting moiety.

14. The method of claim 13, wherein the targeting moiety is expressed on the surface of the exosome, or within the membrane of the exosome.

15. The method of claim 13, wherein the nucleic acids encoding the targeting moiety comprise a fusion protein, wherein the fusion protein comprises an exosomal transmembrane protein and a targeting moiety.

16. The method of claim 13, wherein the targeting moiety is one or more of Asialoglycoprotein Receptor (ASGPR), Toll-Like Receptor 4 ligand (TLR-4 ligand), Notch, CGS-21680, Parathyroid hormone receptor 1 (PTHR1), and Fractalkine receptor (CX3CR1).

* * * * *

UNITED STATES PATENT AND TRADEMARK OFFICE
CERTIFICATE OF CORRECTION

PATENT NO. : 11,519,008 B2  
APPLICATION NO. : 16/410311  
DATED : December 6, 2022  
INVENTOR(S) : C. Ronald Kahn and Thomas Thomou Page 1 of 1

It is certified that error appears in the above-identified patent and that said Letters Patent is hereby corrected as shown below:

On the Title Page

Under (72) Inventors: delete "C. Ronald Kahn, Falls Church, VA (US); Thomas Thomou, Boston, MA (US)" and insert -- C. Ronald Kahn, Boston, MA (US); Thomas Thomou, Falls Church, VA (US) --.

Signed and Sealed this  
Seventh Day of March, 2023

Katherine Kelly Vidal  
*Director of the United States Patent and Trademark Office*

SEQUENCE LISTING

```
<160> NUMBER OF SEQ ID NOS: 4

<210> SEQ ID NO 1
<211> LENGTH: 191
<212> TYPE: DNA
<213> ORGANISM: Artificial Sequence
<220> FEATURE:
<223> OTHER INFORMATION: Ad-pre-hsa_miR-302f

<400> SEQUENCE: 1
gatttaaatc ggactgaatt cctgggttcc ttggggagga ggggccggg ggcccggact      60 cctgggtcct ggcacccacc cgtagaaccg accttgcggg gccttcgccg cacacaagct    120
cgtgtctgtg ggtccgtgtc gggggctcac catcgcggct gggacctccc cggccctccc    180 caccctcga g                                                         191

<210> SEQ ID NO 2
<211> LENGTH: 3081
<212> TYPE: DNA
<213> ORGANISM: Artificial Sequence
<220> FEATURE:
<223> OTHER INFORMATION: Ad-LacZ

<400> SEQUENCE: 2
accatgatta cggattcact ggccgtcgtt ttacaacgtc gtgactggga aaaccctggc     60
gttacccaac ttaatcgcct tgcagcacat cccccttcg ccagctggcg taatagcgaa    120
gaggcccgca ccgatcgccc ttcccaacag ttgcgcagcc tgaatggcga atggcgcttt   180
gcctggtttc cggcaccaga agcggtgccg gaaagctggc tggagtgcga tcttcctgag    240
gccgatactg tcgtcgtccc ctcaaactgg cagatgcacg gttacgatgc gcccatctac    300
accaacgtaa cctatcccat tacggtcaat ccgccgtttg ttcccacgga gaatccgacg    360
ggttgttact cgctcacatt taatgttgat gaaagctggc tacaggaagg ccagacgcga    420
attatttttg atggcgttaa ctcggcgttt catctgtggt gcaacgggcg ctgggtcggt    480
tacggccagg acagtcgttt gccgtctgaa tttgacctga gcgcattttt acgcgccgga    540
gaaaaccgcc tcgcggtgat ggtgctgcgt tggagtgacg gcagttatct ggaagatcag    600
gatatgtggc ggatgagcgg cattttccgt gacgtctcgt tgctgcataa accgactaca    660
caaatcagcg atttccatgt tgccactcgc tttaatgatg atttcagccg cgctgtactg    720
gaggctgaag ttcagatgtg cggcgagttg cgtgactacc tacgggtaac agtttcttta    780
tggcagggtg aaacgcaggt cgccagcggc accgcgcctt cggcggtga aattatcgat    840 gagcgtggtg gttatgccga tcgcgtcaca ctacgtctga acgtcgaaaa cccgaaactg    900
tggagcgccg aaatcccgaa tctctatcgt gcggtggttg aactgcacac cgccgacggc    960
acgctgattg aagcagaagc ctgcgatgtc ggtttccgcg aggtgcggat tgaaaatggt   1020
ctgtgctgct gaacggcaag ccgttgctga ttcgaggcgt taaccgtcac gagcatcatc   1080
ctctgcatgg tcaggtcatg gatgagcaga cgatggtgca ggatatcctg ctgatgaagc   1140
```

```
agaacaactt taacgccgtg cgctgttcgc attatccgaa ccatccgctg tggtacacgc   1200
tgtgcgaccg ctacgcctg tatgtggtgg atgaagccaa tattgaaacc cacggcatgg    1260
tgccaatgaa tcgtctgacc gatgatccgc gctggctacc ggcgatgagc gaacgcgtaa   1320
cgcgaatggt gcagcgcgat cgtaatcacc cgagtgtgat catctggtcg ctggggaatg   1380
aatcaggcca cggcgctaat cacgacgcgc tgtatcgctg atcaaatct gtcgatcctt    1440 cccgcccggt gcagtatgaa ggcggcgag ccgacaccac ggccaccgat attatttgcc    1500
cgatgtacgc gcgcgtggat aagaccagc ccttcccggc tgtgccgaaa tggtccatca    1560
aaaaatggct ttcgctacct ggagagacgc gcccgctgat cctttgcgaa tacgcccacg   1620
cgatgggtaa cagtcttggc ggtttcgcta atactggca ggcgtttcgt cagtatcccc    1680
gtttacaggg cggcttcgtc tgggactggg tggatcagtc gctgattaaa tatgatgaaa   1740
acggcaaccc gtggtcggct tacggcggtg attttggcga tacgccgaac gatcgccagt   1800
tctgtatgaa cggtctggtc tttgccgacc gcacgccgca tccagcgctg acggaagcaa   1860
aacaccagca gcagtttttc cagttccgtt tatccgggca aaccatcgaa gtgaccagcg   1920
aatacctgtt ccgtcatagc gataacgagc tcctgcactg gatggtggcg ctggatggta   1980
agccgctggc aagcggtgaa gtgcctctgg atgtcgctcc acaaggtaaa cagttgattg   2040
aactgctgaa ctaccgcagc cggagagcgc cgggcaactc tggctcacag tacgcgtagt   2100
gcaaccgaac gcgaccgcat ggtcagaagc cgggcacatc agcgcctggc agcagtggcg   2160
tctggcggaa aacctcagtg tgacgctccc cgccgcgtcc cacgccatcc cgcatctgac   2220
caccagcgaa atggatttt gcatcgagct gggtaataag cgttggcaat ttaaccgcca    2280
gtcaggcttt ctttcacaga tgtggattgg cgataaaaaa caactgctga cgccgctgcg   2340
cgatcagttc acccgtgcac cgctggataa cgacattggc gtaagtgaag cgacccgcat   2400
tgaccctaac gcctgggtcg aacgctggaa ggcggcgggc cattaccagg ccgaagcagc   2460
gttgttgcag tgcacggcag atacacttgc tgatgcggtg ctgattacga ccgctcacgc   2520
gtggcagcat caggggaaaa ccttatttat cagccggaaa acctaccgga ttgatggtag   2580
tggtcaaatg gcgattaccg ttgatgttga agtggcgagc gatacaccgc atccggcgcg   2640
gattggcctg aactgccagc tggcgcaggt agcagagcgg gtaaactggc tcggattagg   2700
gccgcaagaa aactatcccg accgccttac tgccgcctgt tttgaccgct gggatctgcc   2760
attgtcagac atgtataccc cgtacgtctt cccgagcgaa aacggtctgc gctgcgggac   2820
gcgcgaattg aattatggcc cacaccagtg gcgcggcgac ttccagttca acatcagccg   2880
ctacagtcaa cagcaactga tggaaaccag ccatcgccat ctgctgcacg cggaagaagg   2940
cacatggctg aatatcgacg gtttccatat ggggattggt ggcgacgact cctggagccc   3000
gtcagtatcg gcggaattcc agctgagcgc cggtcgctac cattaccagt ttctggtgtc   3060
aaaaataata acggctgccg t                                             3081
```

<210> SEQ ID NO 3
<211> LENGTH: 1992
<212> TYPE: DNA
<213> ORGANISM: Artificial Sequence
<220> FEATURE:
<223> OTHER INFORMATION: Ad-Luc-miR-302f-3'UTR

<400> SEQUENCE: 3

```
gatttaaatc atggaagacg ccaaaaacat aaagaaaggc ccggcgccat tctatccgct    60
ggaagatgga accgctggag agcaactgca taaggctatg aagagatacg ccctggttcc   120
```

```
tggaacaatt gcttttacag atgcacatat cgaggtggac atcacttacg ctgagtactt    180
cgaaatgtcc gttcggttgg cagaagctat gaaacgatat gggctgaata caaatcacag    240
aatcgtcgta tgcagtgaaa actctcttca attctttatg ccggtgttgg gcgcgttatt    300
tatcggagtt gcagttgcgc ccgcgaacga catttataat gaacgtgaat tgctcaacag    360
tatgggcatt tcgcagccta ccgtggtgtt cgtttccaaa aaggggttgc aaaaaatttt    420
gaacgtgcaa aaaagctcc caatcatcca aaaaattatt atcatggatt ctaaaacgga     480
ttaccaggga tttcagtcga tgtacacgtt cgtcacatct catctacctc ccggttttaa    540
tgaatacgat tttgtgccag agtccttcga tagggacaag acaattgcac tgatcatgaa    600
ctcctctgga tctactggtc tgcctaaagg tgtcgctctg cctcatagaa ctgcctgcgt    660
gagattctcg catgccagag atcctatttt tggcaatcaa atcattccgg atactgcgat    720
tttaagtgtt gttccattcc atcacggttt tggaatgttt actacactcg atatttgat    780 atgtggattt cgagtcgtct taatgtatag atttgaagaa gagctgtttc tgaggagcct    840
tcaggattac aagattcaaa gtgcgctgct ggtgccaacc ctattctcct tcttcgccaa    900
aagcactctg attgacaaat acgatttatc taatttacac gaaattgctt ctggtggcgc    960 tccccctctct aaggaagtcg gggaagcggt tgccaagagg ttccatctgc caggtatcag  1020
gcaaggatat gggctcactg agactacatc agctattctg attacacccg agggggatga   1080
taaaccgggc gcggtcggta agttgttcc attttttgaa gcgaaggttg tggatctgga    1140
taccgggaaa acgctgggcg ttaatcaaag aggcgaactg tgtgtgagag gtcctatgat   1200
tatgtccggt tatgtaaaca atccggaagc gaccaacgcc ttgattgaca aggatggatg   1260
gctacattct ggagacatag cttactggga cgaagacgaa cacttcttca tcgttgaccg   1320
cctgaagtct ctgattaagt acaaaggcta tcaggtggct cccgctgaat ggaatccat   1380 cttgctccaa cacccaaca tcttcgacgc aggtgtcgca ggtcttcccg acgatgacgc    1440
cggtgaactt cccgccgccg ttgttgtttt ggagcacgga aagacgatga cggaaaaaga   1500
gatcgtggat tacgtcgcca gtcaagtaac aaccgcgaaa aagttgcgcg gaggagttgt   1560
gtttgtggac gaagtaccga aaggtcttac cggaaaactc gacgcaagaa aaatcagaga   1620
gatcctcata aaggccaaga agggcggaaa gatcgccgtg taattctaaa acatggaagc    1680
aattaatcga aacatggaag caattagagg gccctattct atagtgtcac ctaaatgcta    1740
gagctcgctg atcagcctcg actgtgcctt ctagttgcca gccatctgtt gtttgcccct    1800
cccccgtgcc ttccttgacc ctggaaggtg ccactcccac tgtcctttcc taataaaatg    1860
aggaaattgc atcgcattgt ctgagtaggt gtcattctat tctggggggt ggggtggggc    1920
aggacagcaa gggggaggat tgggaagaca atagcaggca tgctggggat gcggtgggct    1980
ctatggctcg ag                                                       1992
```

<210> SEQ ID NO 4
<211> LENGTH: 1771
<212> TYPE: DNA
<213> ORGANISM: Artificial Sequence
<220> FEATURE:
<223> OTHER INFORMATION: Ad-Luc-FGF21-3'UTR

<400> SEQUENCE: 4

```
atggaagacg ccaaaaacat aaagaaaggc ccggcgccat tctatccgct ggaagatgga    60
accgctggag agcaactgca taaggctatg aagagatacg ccctggttcc tggaacaatt   120
```

```
gcttttacag atgcacatat cgaggtggac atcacttacg ctgagtactt cgaaatgtcc      180
gttcggttgg cagaagctat gaaacgatat gggctgaata caaatcacag aatcgtcgta      240
tgcagtgaaa actctcttca attctttatg ccggtgttgg gcgcgttatt tatcggagtt      300
gcagttgcgc ccgcgaacga catttataat gaacgtgaat tgctcaacag tatgggcatt      360
tcgcagccta ccgtggtgtt cgtttccaaa aagggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt    720
gttccattcc atcacggttt tggaatgttt actacactcg atatttgat atgtggattt     780 cgagtcgtct taatgtatag atttgaagaa gagctgtttc tgaggagcct tcaggattac    840
aagattcaaa gtgcgctgct ggtgccaacc ctattctcct tcttcgccaa aagcactctg    900
attgacaaat acgatttatc taatttacac gaaattgctt ctggtggcgc tcccctctct    960
aaggaagtcg gggaagcggt tgccaagagg ttccatctgc caggtatcag gcaaggatat   1020
gggctcactg agactacatc agctattctg attacacccg aggggggatga taaaccgggc   1080 gcggtcggta aagttgttcc atttttgaa gcgaaggttg tggatctgga taccgggaaa    1140
acgctgggcg ttaatcaaag aggcgaactg tgtgtgagag gtcctatgat tatgtccggt   1200
tatgtaaaca atccggaagc gaccaacgcc ttgattgaca aggatggatg gctacattct   1260
ggagacatag cttactggga cgaagacgaa cacttcttca tcgttgaccg cctgaagtct   1320
ctgattaagt acaaaggcta tcaggtggct cccgctgaat tggaatccat cttgctccaa   1380 cacccccaaca tcttcgacgc aggtgtcgca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aaggtcttac cggaaaactc gacgcaagaa aaatcagaga gatcctcata   1620
aaggccaaga agggcggaaa gatcgccgtg taattctact cttcctgaat ctagggctgt   1680 ttcttttttgg gtttccactt atttattacg ggtatttatc ttatttattt attttagttt   1740 tttttttctta cttggaataa taaagagtct g                                 1771
```